US012751953B2

(12) United States Patent
Müller et al.

(10) Patent No.: US 12,751,953 B2
(45) Date of Patent: Oct. 6, 2026

(54) MRGX RECEPTOR ANTAGONISTS

(71) Applicants: Rheinische-Friedrich-Wilhelms-Universität Bonn, Bonn (DE); Katholieke Universiteit Leuven, Leuven (BE)

(72) Inventors: Christa Müller, Bonn (DE); Mohamad Wessam Alnouri, Niederau (DE); Yvonne Riedel, Bonn (DE); Dominik Thimm, Bonn (DE); Daniel Marx, Linz am Rhein (DE); Vigneshwaran Namasivayam, Bonn (DE); Susanne Gattner, Bonn (DE); Piet Herdewyn, Heverlee (BE); Steven De Jonghe, Tervuren (BE); Piotr Leonczak, Leuven (BE); Sven Verdonck, Diest (BE)

(73) Assignees: Rheinische-Friedrich-Wilhelms-Universitat Bonn, Bonn (DE); Katholieke Universiteit Leuven KU Leuven Research & Development, Leuven (BE)

( * ) Notice: Subject to any disclaimer, the term of this patent is extended or adjusted under 35 U.S.C. 154(b) by 191 days.

(21) Appl. No.: 16/670,149

(22) Filed: Oct. 31, 2019

(65) Prior Publication Data

US 2021/0128561 A1 May 6, 2021

(51) Int. Cl.

| | |
|---|---|
| ***A61K 31/519*** | (2006.01) |
| ***A61K 31/542*** | (2006.01) |
| *A61K 9/20* | (2006.01) |
| *A61K 9/48* | (2006.01) |

(52) U.S. Cl.

CPC .......... *A61K 31/519* (2013.01); *A61K 31/542* (2013.01); *A61K 9/20* (2013.01); *A61K 9/48* (2013.01)

(58) Field of Classification Search

CPC ............................ A61K 31/519; A61K 31/542

USPC .............................. 514/224.5, 267, 393, 394

See application file for complete search history.

(56) References Cited

FOREIGN PATENT DOCUMENTS

WO WO-2017168137 A1 * 10/2017 .......... A61K 31/519

OTHER PUBLICATIONS

Chen, M., M. Takano-Maruyama, O. Pereira-Smith, G. Gaufo and K. Tominaga, "MRG15, a component of HAT and HDAC complexes, is essential for proliferation and differentiation of neural precursor cells", J Neurosci Res., May 15, 2009; 87(7): pp. 1522-1531. (Year: 2009).*

Paul, Subhankar, "Dysfunction of the ubiquitin-proteasome system in multiple disease conditions: therapeutic approaches", BioEssays (2008), 30: pp. 1172-1184. (Year: 2008).*

Tominaga, K., E. Tominaga, M. Ausserlechner and O. Pereira-Smith, "The cell senescence inducing gene product MORF4 is regulated by degradation via the ubiquitin/proteasome pathway", Experimental Cell Research (2010), 316(1), pp. 92-102. (Year: 2009).*

ClevelandClinic, Psoriasis, https://my.clevelandclinic.org/health/diseases/6866-psoriasis, Available online: Sep. 15, 2022. (Year: 2022).*

Borsook, "Neurological diseases and pain", Brain (2012), 135: pp. 320-344. (Year: 2012).*

Akuzawa et al., Journal of Cell and Animal Biology, Jan. 2007, "Morphine is an Exogenous Ligand for MrgX2, a G protein-coupled Receptor for Cortistatin".

Fujisawa, D.; Kashiwakura, J.; Kita, H.; Kikukawa, Y.; Fujitani, Y.; Sasaki-Sakamoto, T.; Kuroda, K.; Nunomura, S.; Hayama, K.; Terui, T.; Ra, C.; Okayama, Y. Expression of Mas-related gene X2 on mast cells is upregulated in the skin of patients with severe chronic urticaria. *J. Allergy. Clin. Immunol.* 2014, 3, 622-633.

Hou, Y.; Che, D.; Ma, P.; Zhao, T .; Zeng, Y.; Wang, N. *Anti-pseudo-allergy effect of isoliquiritigenin is MrgX2-dependent. Immunol. Lett. 2018*, 198, 52-59.

Johnson, T.; Siegel, D. Complanadine A, a selective agonist for the Mas-related G protein-coupled receptor X2. *Bioorg. Med. Chem. Lett.* 2014, 15, 3512-5.

Kamohara, M.; Matsuo, A.; Takasaki, J.; Kohda, M.; Matsumoto, M.; Matsumoto, S.; Soga, T.; Hiyama, H.; Kobori, M.; Katou, M. Identification of MrgX2 as a human G protein-coupled receptor for proadrenomedullin N-terminal peptides. *Biochem. Biophys. Res. Commun. 2005*, 4, 1146-52).

H.; Kashem, S.W.; Collington, S.J.; Qu, H.; Lambris, J.D.; Ali, H. PMX-53 as a dual CD88 antagonist and an agonist for Mas-related gene 2 (MrgX2) in human mast cells. *Mol. Pharmacol.* 2011, 6, 1005-13.

Malik, L.; Kelly, N.M.; Ma, J.N.; Currier, E.A.; Burstein, ES.; Olsson, R. Discovery of non-peptidergic MrgX1 and MrgX2 receptor agonists and exploration of an initial SAR using solid-phase synthesis. *Bioorg. Med. Chem. Lett.* 2009, 6, 1729-32.

Ogasawara, H.; Furuno, M.; Edamura, K.; Noguchi, M. Novel MrgX2 antagonists inhibit IgE-independent activation of human umbilical cord blood-derived mast cells. J. Leukoc. Biol., 2019, 106(5), 1069-77.

Okayama, Y.; Saito, H.; Ra, C. Targeting human mast cells expressing G protein-coupled receptors in allergic diseases. *Allergol. Int.* 2008, 3, 197-203.

Roy, S.; Ganguly, A.; Haque, M.; Ali, H. *J. Immunol.* 2019, 202(4), 1229-38.

Solinski, H.J.; Gudermann, T.; Breit, A. Pharmacology and signaling of MAS-related G protein-coupled receptors. *Pharmacol. Rev.* 2014, 3, 570-97; Robas, N.; Mead, E.; Fidock, M. MrgX2 is a high potency cortistatin receptor expressed in dorsal root ganglion. *J. Biol. Chem.* 2003, 45, 44400-4).

(Continued)

*Primary Examiner* — Kamal A Saeed

*Assistant Examiner* — Sagar Patel

(74) *Attorney, Agent, or Firm* — The Dobrusin Law Firm, P.C.

(57) ABSTRACT

The invention relates to a method for preventing or treating a disease or disorder that is associated with the MrgX2 receptor. The invention also relates to MrgX2 antagonists and physiologically acceptable salts thereof. The invention also relates to pharmaceutical compositions and dosage forms comprising an MrgX2 antagonist.

7 Claims, No Drawings

(56) References Cited

OTHER PUBLICATIONS

Southern, C.; Cook, J.M.; Neetoo-Isseljee, Z.; Taylor, D.L.; Kettleborough, C.A.; Merritt, A.; Bassoni, D.L.; Raab, W.J.; Quinn, E.; Wehrman, T.S.; Davenport, A.P.; Brown, A.J.; Green, A.; Wigglesworth, M.J.; Rees, S. Screening β-arrestin recruitment for the identification of natural ligands for orphan G protein-coupled receptors. J. Biomol. Screen. 2013, 18, 599-609.
Subramanian, H.; Gupta, K.; Guo, Q.; Price, R.; Ali, H. Mas-related gene X2 (MrgX2) is a novel G protein-coupled receptor for the antimicrobial peptide LL-37 in human mast cells: resistance to receptor phosphorylation, desensitization, and internalization. *J. Biol. Chem.* 2011, 52, 44739-49.
Subramanian, H.; Gupta, K.; Lee, D.; Bayir, A.K.; Ahn, H.; Ali, H. β-Defensins activate human mast cells via Mas-related gene X2. *J. Immunol.* 2013, 1, 345-52.
Subramanian et al., Molecular Pharmacol, 2011, PMX-53 as a Dual CD88 Antagonist and an Agonist for Mas-Related Gene 2 (MrgX2) in Human Mast Cells.
Tatemoto, K.; Nozaki, Y.; Tsuda, R.; Konno, S.; Tomura, K.; Furuno, M.; Ogasawara, H.; Edamura, K.; Takagi, H.; Iwamura, H.; Noguchi, M.; Naito, T. Immunoglobulin E-independent activation of mast cell is mediated by Mrg receptors. *Biochem. Biophys. Res. Commun.* 2006, 4, 1322-8.
Wang, N.; Che, D.; Zhang, T.; Liu, R.; Cao, J.; Wang, J.; Zhao, T.; Ma, P.; Dong, X.; He, L. Saikosaponin A inhibits compound 48/80-induced pseudo allergy via the Mrgprx2 pathway in vitro and in vivo. *Biochem. Pharmacol.* 2018, 148, 147-54.

* cited by examiner

MRGX RECEPTOR ANTAGONISTS

The invention relates to MrgX receptor ligands useful for treating, alleviating and/or preventing diseases and disorders related to MrgX receptor function as well as pharmaceutical compositions comprising such compounds and methods for preparing such compounds. The invention is further directed to the use of these compounds, alone or in combination with other therapeutic agents, for alleviating, preventing and/or treating diseases and disorders, especially the use as antinociceptive, anti-inflammatory or antipruritic drugs.

Mas-related genes (Mrgs) belong to a large family of G protein-coupled receptor genes found in rodents. Human MrgX receptors are G protein-coupled 7-transmembrane receptors sharing 41-52% amino acid identity with each other, but have probably no direct orthologs in rodents. MrgX2 (in the literature also referred to as "mas-related G protein-coupled receptor X2", MRGX2, MrgprX2, MRGPR-X2, and the like), is a member of the MrgX family (in the literature also referred to as "mas-related G protein-coupled receptor X", MRGX, MrgprX, Mrgpr-X, and the like). MrgX2 is, for example, expressed in the small diameter neurons of sensory ganglia and mast cells. It can be activated by several compounds, such as substance P, vasoactive intestinal peptide, cortistatin (CST), proadrenomedullin N-terminal peptide (PAMP), LL-37, PMX-53 and β-defensins. MrgX2 activation is related to nociception, adrenal gland secretion and mast cell degranulation.

One putative physiological agonist for MrgX2 is CST-14. CST-14 showed an $EC_{50}$ value of 25 nM in calcium mobilization assays in recombinant HEK cells (Solinski, H. J.; Gudermann, T.; Breit, A. Pharmacology and signaling of MAS-related G protein-coupled receptors. *Pharmacol. Rev.* 2014, 3, 570-97; Robas, N.; Mead, E.; Fidock, M. MrgX2 is a high potency cortistatin receptor expressed in dorsal root ganglion. *J. Biol. Chem.* 2003, 45, 44400-4).

MrgX2 can be activated by proadrenomedullin N-terminal 20 peptide (PAMP-20) and its truncated form PAMP-9-20/PAMP-12 (Kamohara, M.; Matsuo, A.; Takasaki, J.; Kohda, M.; Matsumoto, M.; Matsumoto, S.; Soga, T.; Hiyama, H.; Kobori, M.; Katou, M. Identification of MrgX2 as a human G protein-coupled receptor for proadrenomedullin N-terminal peptides. Biochem. *Biophys. Res. Commun.* 2005, 4, 1146-52).

MrgX2 could be activated in calcium assays by morphine ($EC_{50}$ value 4.5 μM), dextrorphan ($EC_{50}$ 1.4 μM) as well as 3-methoxymorphinan ($EC_{50}$ 4.7 μM). (Akuzawa, N.; Obinata, H.; Izumi, T.; Takeda, S. Morphine is an exogenous ligand for MrgX2, a G protein-coupled receptor for cortistatin. *J. Cell Anim. Biol.* 2007, 12, 216-221).

TAN-67, a potent δ-opioid agonist, could be identified as an agonist at the MrgX2 receptor with an $EC_{50}$ value of about 1 μM in both β-arrestin and calcium mobilization assays (Southern, C.; Cook, J. M.; Neetoo-Isseljee, Z.; Taylor, D. L.; Kettleborough, C. A.; Merritt, A.; Bassoni, D. L.; Raab, W. J.; Quinn, E.; Wehrman, T. S.; Davenport, A. P.; Brown, A. J.; Green, A.; Wigglesworth, M. J.; Rees, S. Screening β-arrestin recruitment for the identification of natural ligands for orphan G protein-coupled receptors. *J. Biomol. Screen.* 2013, 18, 599-609).

The natural product "Complanadine A" was described as a selective MrgX2 agonist after screening it at 165 G protein-coupled receptors with an $EC_{50}$ value of 5.5 μM in calcium assays (Johnson, T.; Siegel, D. Complanadine A, a selective agonist for the Mas-related G protein-coupled receptor X2. *Bioorg. Med. Chem. Lett.* 2014, 15, 3512-5).

Novel synthetic agonists for MrgX2 were proposed by Malik et al. and have a tetracyclic benzimidazole scaffold (Malik, L.; Kelly, N. M.; Ma, J. N.; Currier, E. A.; Burstein, E S.; Olsson, R. Discovery of non-peptidergic MrgX1 and MrgX2 receptor agonists and exploration of an initial SAR using solid-phase synthesis. *Bioorg. Med. Chem. Lett.* 2009, 6, 1729-32).

MrgX2 receptors are highly expressed on mast cells. Mast cells express, among others, beta-2 adrenergic receptors, adenosine receptors, several chemokine receptors, GPR34, Histamine H4, several nucleotide receptors as well as MrgX1 and MrgX2. The activation of some of these receptors leads to degranulation of the mast cells, which means a potential to treat diseases like asthma and urticaria. MrgX2 is one of these potential target receptors. (Okayama, Y.; Saito, H.; Ra, C. Targeting human mast cells expressing G protein-coupled receptors in allergic diseases. *Allergol. Int.* 2008, 3, 197-203).

Tatemoto et al. have found that basic secretagogues could activate MrgX2 receptors with $EC_{50}$ values between $10^{-4}$ and $10^{-7}$M in calcium assays using recombinant HEK-293 cells. (Tatemoto, K.; Nozaki, Y.; Tsuda, R.; Konno, S.; Tomura, K.; Furuno, M.; Ogasawara, H.; Edamura, K.; Takagi, H.; Iwamura, H.; Noguchi, M.; Naito, T. Immunoglobulin E-independent activation of mast cell is mediated by Mrg receptors. *Biochem. Biophys. Res. Commun.* 2006, 4, 1322-8).

The C5a receptor antagonist PMX-53, a cyclic hexapeptide based on the terminal amino acid sequence of C5a, behaves as an agonist at MrgX2 receptor. PMX-53 could induce mast cell degranulation and a calcium signal via MrgX2 receptors. It was also found that the C3a agonist, E7, could activate MrgX2 receptors in mast cells and induce degranulation, thus behaving as a dual agonist at MrgX2 and C3a receptors. (Subramanian, H.; Kashem, S. W.; Collington, S. J.; Qu, H.; Lambris, J. D.; Ali, H. PMX-53 as a dual CD88 antagonist and an agonist for Mas-related gene 2 (MrgX2) in human mast cells. *Mol. Pharmacol.* 2011, 6, 1005-13; Kashem, S. W.; Subramanian, H.; Collington, S.; Magotti, P.; Lambris, J. D.; Ali, H. G protein-coupled receptor specificity for C3a and compound 48/80-induced degranulation in human mast cells: roles of Mas-related genes MrgX1 and MrgX2. *Eur. J. Pharmacol.* 2011, 1-2, 299-304).

Another component of the immune system, which was reported to act via MrgX2 receptors, is the antimicrobial peptide LL-37. LL-37 was previously reported to induce chemokine production and mast cell degranulation via unknown mechanisms (Subramanian, H.; Gupta, K.; Guo, Q.; Price, R.; Ali, H. Mas-related gene X2 (MrgX2) is a novel G protein-coupled receptor for the antimicrobial peptide LL-37 in human mast cells: resistance to receptor phosphorylation, desensitization, and internalization. *J. Biol. Chem.* 2011, 52, 44739-49).

Other cationic antimicrobial peptides, human #-defensin 2 and 3 (hBD 2, 3), were found to activate MrgX2 and cause mast cell degranulation (Subramanian, H.; Gupta, K.; Lee, D.; Bayir, A. K.; Ahn, H.; Ali, H. #-Defensins activate human mast cells via Mas-related gene X2. *J Immunol.* 2013, 1, 345-52).

In a recent study, MrgX2 receptor expression in skin mast cells of patients with chronic urticaria (CU) was compared with that of a nonatopic control. The study showed that the expression levels of MrgX2 mRNA in skin mast cells are much higher than in lung-derived mast cells and that the number of $MrgX2^{+}$ mast cells was significantly greater in skin tissues from CU patients than in nonatopic controls.

Hence, the blockade of MrgX2 on human skin mast cells might offer a novel approach to the prevention and treatment of severe CU (Fujisawa, D.; Kashiwakura, J.; Kita, H.; Kikukawa, Y.; Fujitani, Y.; Sasaki-Sakamoto, T.; Kuroda, K.; Nunomura, S.; Hayama, K.; Terui, T.; Ra, C.; Okayama, Y. Expression of Mas-related gene X2 on mast cells is upregulated in the skin of patients with severe chronic urticaria. *J. Allergy. Clin. Immunol.* 2014, 3, 622-633).

Roy et al. identified the angiogenic host defense peptide AG-30/5C, which induces angiogenesis and promotes wound healing, as a G protein-biased agonist of MrgX2. AG-30/5C was shown to mediate degranulation of human LAD2 mast cells at a concentration of 0.01 μM (estimated $EC_{50}$ value: less than 0.1 μM) but it was found not to activate #-arrestin-dependent signaling (Roy, S.; Ganguly, A.; Haque, M.; Ali, H. *J. Immunol.* 2019, 202(4), 1229-38).

In 2019, MrgX2 was evaluated as a biomarker for predicting treatment outcomes in allergic asthma in a multicenter cohort study. The G protein-coupled receptor subtype MrgX2 was shown to be overexpressed in the allergic asthma group (in comparison to the non-allergic asthma group).

Furthermore, high MrgX2 serum levels were significantly associated with allergic asthma requiring moderate-to-high inhaled corticosteroid (ICS) doses. Since high levels suggest the use of higher ICS doses, MrgX2 might be a valuable biomarker for the therapy of patients with uncontrolled severe allergic asthma (An, J.; Lee, J. H.; Won, H. K.; Kang, Y.; Song, W. J.; Kwon, H. S.; Cho, Y. S.; Moon, H. B.; Kim, T. B. *Allergy,* 2019, doi: 10.1111/all.14084 (Epub ahead of print)) and MrgX2 antagonists may consequently be useful for the treatment of allergic asthma.

Recently, MrgX2 was demonstrated to be activated by the small chemokine (C-X-C motif) ligand 14 (CXCL14) in a dose-dependent manner using the cellosaurus CHEM1 cell line recombinantly expressing MrgX2. Its determined $EC_{50}$ value was 0.570 μM. In order to confirm the specificity for MrgX2, CXCL14 was tested in calcium assays using CHEM1 cells without MrgX2 overexpression and was shown not to mediate calcium release (Golz S. et al. European patent, EP 3 011 340 B1, Mrg receptor modulation, filed 16 Jun. 2014, issued 22 Nov. 2017).

So far, only very weakly potent MrgX2 antagonists have been described in literature:

- the tripeptide Gln-D-Trp(Formyl-)Phe-benzylester, abbreviated QWF, which is a neurokinin-1 receptor antagonist as well; used concentrations: 1 μM vs. 500 nM substance P in calcium imaging assay and 100 μM vs. 1 μM substance P in human LAD2 mast cell degranulation assay; β-hexosaminidase release of SP alone was: 60% and of SP and QWF together: 20% (Azimi, E.; Reddy, V. B.; Shade, K. C.; Anthony, R. M.; Talbot, S.; Pereira, P. J.; Lerner, E. A. Dual action of neurokinin-1 antagonists on Mas-related GPCRs. *JCI Insight* 2016, 1(16), e89362);
- Saikosaponin A, a triterpenoid glycoside, extracted from the radix of *Bupleurum falcatnum*; used concentration: 0.50 μM vs. 30 μg/mL (≈31.2 μM) compound 48/80 in human LAD2 mast cell degranulation assay: β-hexosaminidase release of substance P alone: 100% and of substance P and saikosaponin A together: 30% (Wang, N.; Che, D.; Zhang, T.; Liu, R.; Cao, J.; Wang, J.; Zhao, T.; Ma, P.; Dong, X.; He, L. Saikosaponin A inhibits compound 48/80-induced pseudo allergy via the Mrgprx2 pathway in vitro and in vivo. *Biochem. Pharmacol.* 2018, 148, 147-54);
- Isoliquiritigenin, a chalcone isolated from the roots and stems of *Glycyrrhiza glabra, G. uralensis* and *G. inflate*; used concentration: 50 μM vs. 30 μg/mL (≈31.2 μM) compound 48/80 in human LAD2 mast cell degranulation assay: β-hexosaminidase release of compound 48/80 alone: 85% and of compound 48/80 and isoliquiritigenin together: 40% (Hou, Y.; Che, D.; Ma, P.; Zhao, T.; Zeng, Y.; Wang, N. Anti-pseudo-allergy effect of isoliquiritigenin is MrgX2-dependent. *Immunol. Lett.* 2018, 198, 52-59);
- Compound 1 (1-(5H-10$\lambda^2$-phenazin-5-yl)ethan-lone) and compound 2 (3-(pyridine-2-ylmethyl)-2-thioxo-2,3-dihydro-4H-1$\lambda^2$-quinazolin-4-one) were tested versus CST-14 in calcium mobilization assays; their $IC_{50}$ values were 1.6 and 2.5 μM, respectively (Ogasawara, H.; Furuno, M.; Edamura, K.; Noguchi, M. Novel MrgX2 antagonists inhibit IgE-independent activation of human umbilical cord blood-derived mast cells. *J. Leukoc. Biol.,* 2019, 106(5), 1069-77).

The human MrgX2 receptor represents a fundamentally new drug target, and the development of potent MrgX2 receptor antagonists to be used for antinociception or neuroprotection or other diseases requires the design of novel drugs targeting the MrgX2 receptor.

It was an object of the invention to provide compounds that have advantages compared to the compounds of the prior art. The compounds should act as potent and selective MrgX receptor antagonists, in particular with a high ability to block the $G_q$ protein-coupled pathway including biased antagonists (preferably or solely blocking the G-protein-coupled pathway in contrast to 3-arrestin recruitment, exhibit bioavailability, and thus may be useful as antinociceptive or antipruritic drugs or for the prevention or treatment of other diseases. Moreover, it was an object of the invention to provide methods for preparing said compounds. It was furthermore an object of the invention to provide compounds and pharmaceutical formulations for the treatment, alleviation and/or prevention of a host of diseases and disorders connected to MrgX2 function. It was a further object of the invention to provide the use of these compounds for alleviating, preventing and/or treating diseases and disorders connected to MrgX function, particularly for, but not limited to the use as antinociceptive or antipruritic agents.

This object has been solved by the subject-matter of the patent claims.

The present invention is directed to certain derivatives which act as MrgX2 receptor antagonists and therefore are useful as antinociceptive or antipruritic drugs.

In a first aspect, the invention is directed to a method for preventing or treating a disease or disorder that is associated with the MrgX2 receptor comprising administering to a subject in need thereof a therapeutically effective amount of an MrgX2 antagonist according to general formula (A)

(A)

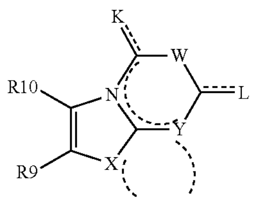

wherein

K means ═O or ═S or ═NH, W means —CR1═, and L means —R2; or

K means —R2, W means —CR1═, and L means ═O; or

K means —R1, W means —N═, and L means —R2; or

K means —R1, W means —CH═, and L means —R2;

X means —N═ and Y means —NR3-; or

X means —NR4- and Y means —N═; or

X means —NR4- and Y means —CR0═; or

X means —N═ and Y means —S—; or

X means —O— and Y means —N═; or

X means —S— and Y means —N═; or

X means —N═ and Y means —N═;

R0, R1, R2, R3, R4 independently of one another mean —H; —$C_{1-6}$-alkyl; —$C_{1-6}$-cycloalkyl; -phenyl; $C_{1-6}$-alkyl-phenyl; -heteroaryl selected from the group consisting of thienyl, furanyl and pyrrolyl; —C(═O)OH; —C(═O)O—$C_{1-6}$-alkyl; —CN; —OH; —O—$C_{1-6}$-alkyl, —$NH_2$, —S—$C_{1-6}$-alkyl; —F, —Cl, —Br, or —I; or R1 and R2, or R0 and R4 together with the atoms to which they are attached form a six membered saturated unsubstituted alicyclic ring;

R9 and R10 independently of one another mean —H, —$C_{1-6}$-alkyl, —CN, —OH, —O—$C_{1-6}$-alkyl, —F, —Cl, —Br, —I; or R9 and R10 together with the carbon atoms to which they are attached form a phenyl ring optionally substituted with R5, R6, R7 and R8;

wherein R5, R6, R7 and R8 independently of one another mean —H, —$C_{1-6}$-alkyl, —CN, —OH, —O—$C_{1-6}$-alkyl, —F, —Cl, —Br, —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(═O)OH, —C(═O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "$C_{1-6}$-cycloalkyl" may be linear or branched, saturated or unsaturated, unsubstituted or monosubstituted with a substituent selected from —CN, —C(═O)OH, —C(═O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "phenyl" may be unsubstituted, mono- or disubstituted with a substituent independently selected from —CN, —C(═O)OH, —C(═O)—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "heteroaryl" may be linear or branched, saturated or unsaturated, unsubstituted or monosubstituted with a substituent selected from —CN, —C(═O)OH, —C(═O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

or a physiologically acceptable salt thereof.

In a preferred embodiment of the method according to the invention, the disease or disorder that is associated to the MrgX2 receptor is selected from the group consisting of pain, especially acute, nociceptive, neuropathic or chronic pain, inflammatory pain or itch. In another preferred embodiment of the method according to the invention, the disease or disorder that is associated to the MrgX2 receptor is selected from the group consisting of anxiety, stress and stress-associated syndromes, depression, epilepsy, Alzheimer's disease, senile dementia, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhoea, cachexia, urinary incontinence or as a muscle relaxant, anticonvulsive or anaesthetic or for co-administration in the case of treatment with an opioid analgesic or with an anaesthetic, for diuresis or antinatriuresis, anxiolysis, for modulation of motor activity, for modulation of neurotransmitter secretion and treatment of neurodegenerative diseases associated therewith, for the treatment of withdrawal symptoms and/or for reducing the addictive potential of opioids. In yet another preferred embodiment of the method according to the invention, the disease or disorder that is associated to the MrgX2 receptor is selected from the group consisting of asthma, urticaria, skin inflammation, dry skin, atopic eczema, psoriasis, urticaria, scabies, non-allergic hypersensitivity reactions, fibrosis and itch.

In a preferred embodiment of the method according to the invention, the MrgX2 antagonist is according to general formula (B)

(B)

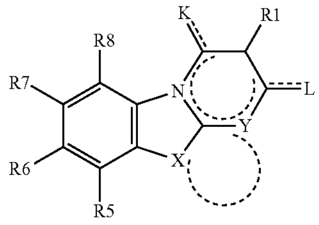

wherein

K means ═O or ═S, and L means —R2; or

K means —R2 and L means ═O; and

X means —N═ and Y means —NR3-; or

X means —NR4- and Y means —N═; or

X means —NR4- and Y means —CR0═; or

X means —N═ and Y means S; or

X means —O— and Y means —N═; or

X means —S— and Y means —N═; or

X means —N═ and Y means —N═.

In another preferred embodiment of the method according to the invention, the MrgX2 antagonist is according to general formula (C)

(C)

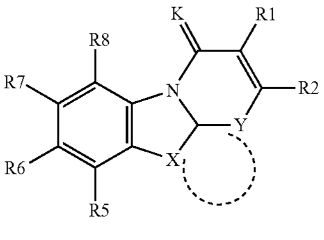

wherein

K means ═O or ═S; and

X means —N═ and Y means —NR3-; or

X means —NR4- and Y means —N═; or

X means —NR4- and Y means —CR0═; or

X means —N═ and Y means S; or

X means —O— and Y means —N=; or

X means —S— and Y means —N=; or

X means —N= and Y means —N=.

In a preferred embodiment of the method according to the invention, the MrgX2 antagonist is selected from the group consisting of compounds according to general formula (I), (II), (III), (IV), (V), (VI), (VII), (VIII), (IX), (X), (XI), and (XII):

(I)

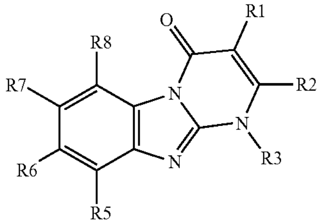

(II)

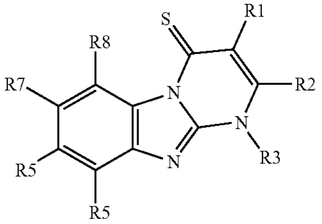

(III)

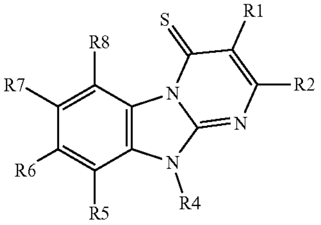

(IV)

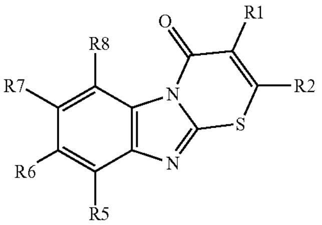

(V)

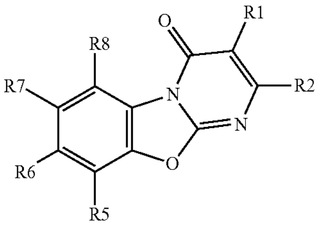

(VI)

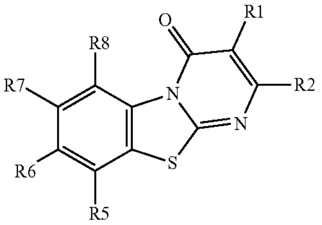

-continued (VII)

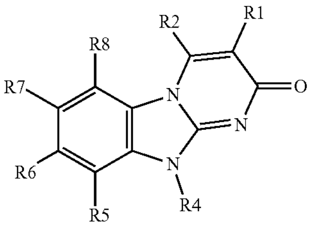

(VIII)

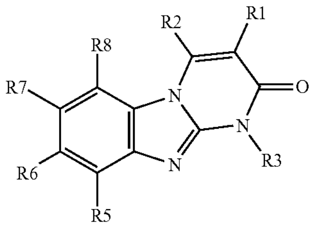

(IX)

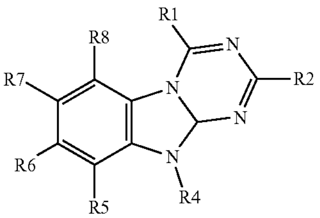

(X)

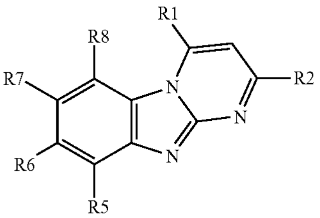

(XI)

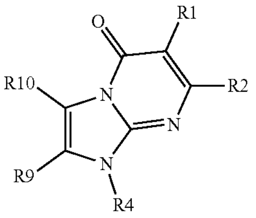

(XII)

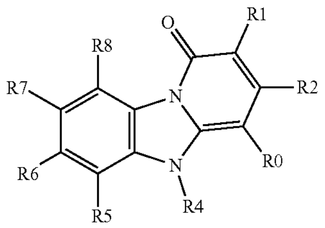

According to a preferred embodiment of the method according to the invention, in general formula (A), R0 means —H or —CN;

R1 means —H, $—CH_3$, $—CH_2CH_3$, $—CH_2CH_2CH_3$, $—CH_2CH_2CH_2CH_3$, $—CH_2CH_2CH(CH_3)_2$, $—CH_2CH_2C(=O)OCH_2CH_3$, $—CH_2CH_2—CN$, $—CH_2CH_2—Cl$, $—CH_2CH_2—OH$, $—CH_2CH_2—OCH_3$, $—CH_2CH_2—N_3$, $—CH_2CH_2—NHCH_3$, $—C(=O)OH$, $—C(=O)OCH_3$, $—C(=O)OCH_2CH_3$, —$CH_2$-phenyl with phenyl being unsubstituted, —$CH_2CH_2$-phenyl with phenyl being unsubstituted, —S—$CH_3$ or —$NH_2$;

and/or

R2 means —H, —$CH_3$, —$CH_2CH_2CH_3$, —$CH(CH_3)_2$, —$CH_2CH(CH_3)_2$, —$C(CH_3)_3$, -cyclopropyl, -phenyl with phenyl being unsubstituted, -para-methoxyphenyl, -2-thienyl, —$CH_2C(=O)OH$, —$C(=O)OCH_3$, —$CH_2C(=O)OCH_3$, —$CH_2C(=O)OCH_2CH_3$, —$C(CH_3)_2(OH)$, —$CH_2OCH_3$, —$SCH_3$, —$NH_2$ or —OH;

or

R1 and R2 together with the atoms to which they are attached form a cyclohexyl ring and mean —$CH_2CH_2CH_2CH_2$—;

and/or

R3 means —H, —$CH_3$, —$CH_2CH_2CH_3$, —$CH_2$-phenyl, —$CH_2$-p-chlorophenyl or —$CH_2$—CN;

and/or

R4 means —H, —$CH_3$ or —$CH_2$-phenyl with phenyl being unsubstituted;

and/or

R9 means —H; and/or R10 means —H; or R9 and R10 together with the carbon atoms to which they are attached form a phenyl ring optionally substituted with R5, R6, R7 and R8;

wherein

R5, R6, R7 and R8 independently of one another mean —H, —$CH_3$, —OH, —$OCH_3$, —F, —Cl, —Br or —CN, and preferably R5 means —H or —$CH_3$; and/or R6 means —H, —$CH_3$, —OH, —$OCH_3$, —F, —Cl, —Br or —CN; and/or R7 means —H, —$CH_3$, —F, —Cl, —Br, —CN, —$OCH_3$ or —OH; and/or R8 means —H;

or

R6 and R7 together with the carbon atoms to which they are attached form an unsubstituted phenyl ring.

In a preferred embodiment of the method according to the invention, the MrgX2 antagonist is selected from compounds (I) A-1 to A-30 and the physiologically acceptable salts thereof:

A-1

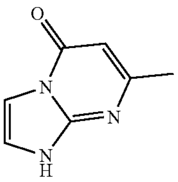

A-2

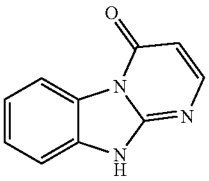

-continued

A-3

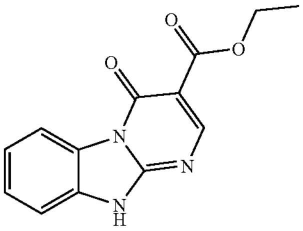

A-4

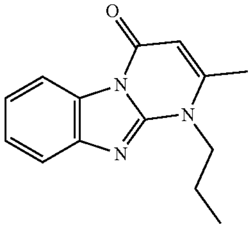

A-5

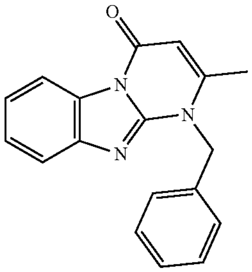

A-6

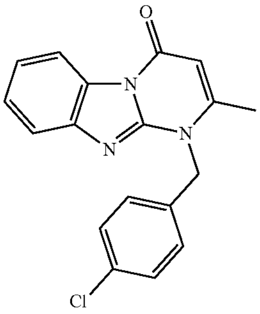

A-7

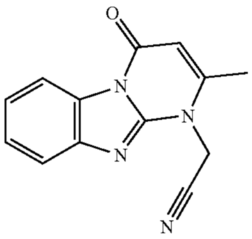

A-8

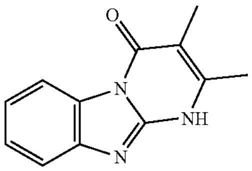

-continued
A-9
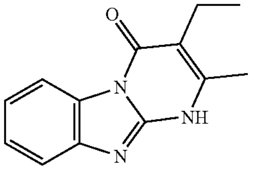
A-10
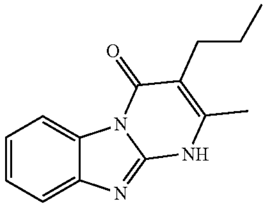
A-11
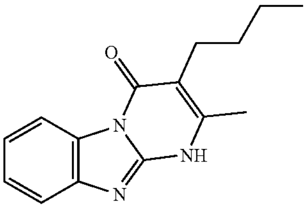
A-12
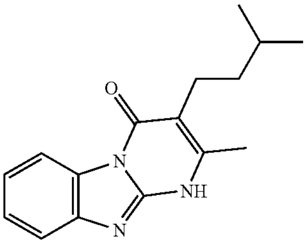
A-13
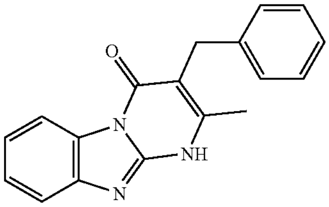
A-14
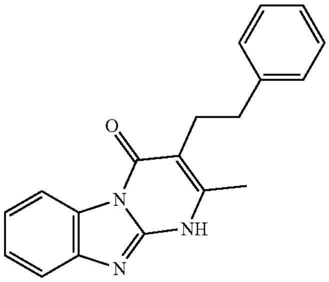
A-15
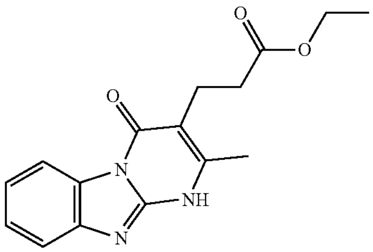
-continued
A-16
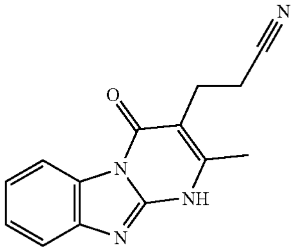
A-17
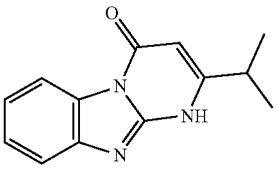
A-18
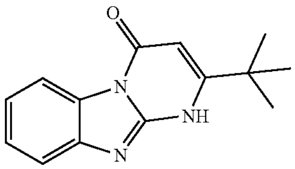
A-19
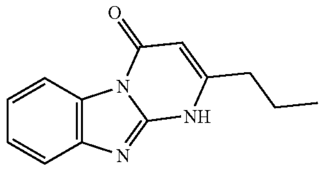
A-20
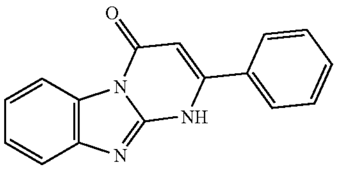
A-21
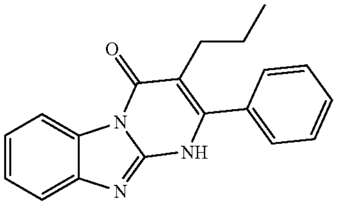
A-22
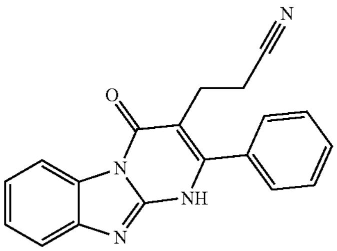
A-23
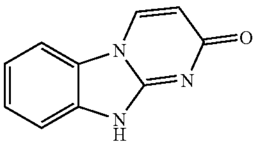

-continued
A-24
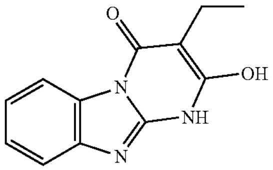
A-25
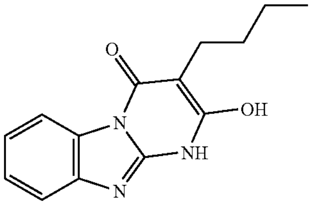
A-26
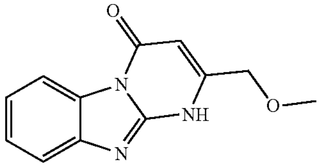
A-27
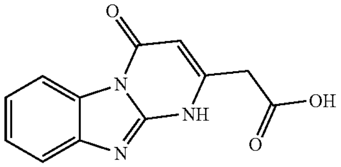
A-28
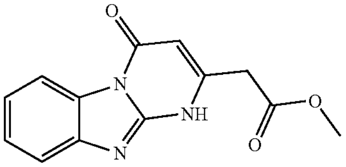
A-29
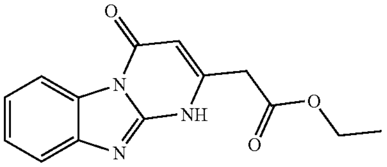
A-30
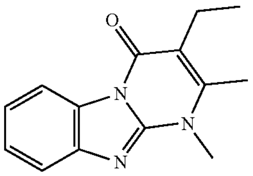
and
(II) B-31 to B-66 and the physiologically acceptable salts thereof:
B-31
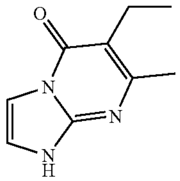
-continued
B-32
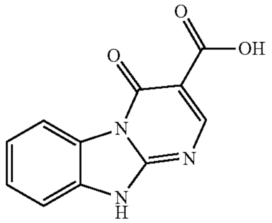
B-33
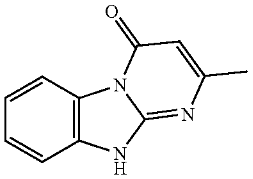
B-34
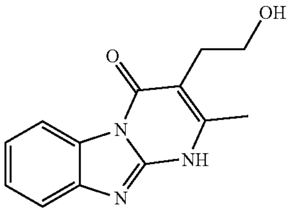
B-35
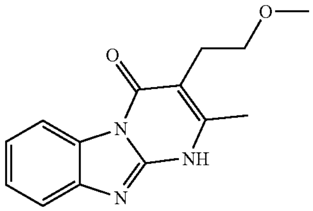
B-36
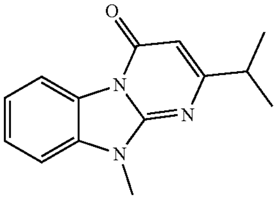
B-37
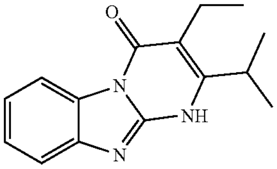
B-38
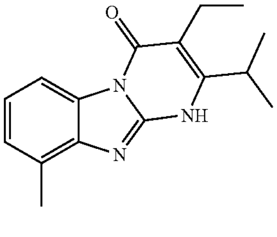

-continued
B-39
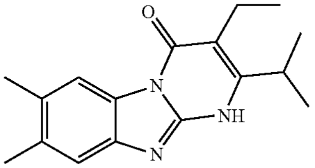
B-40
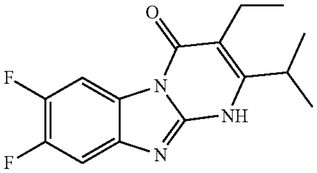
B-41
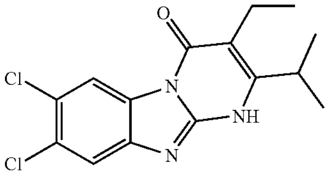
B-42
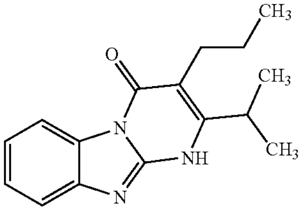
B-43
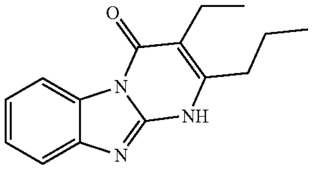
B-44
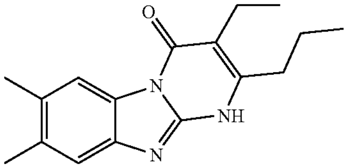
B-45
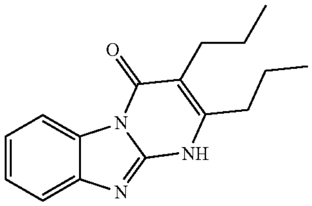
B-46
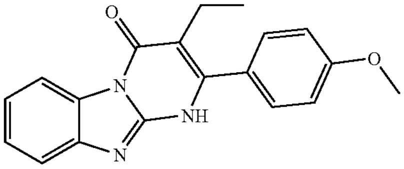
-continued
B-47
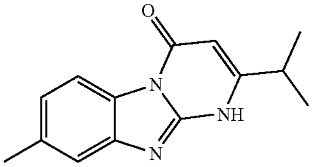
+
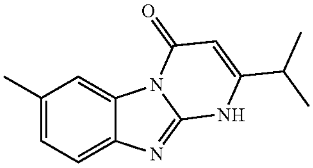
B-48
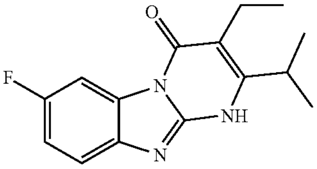
+
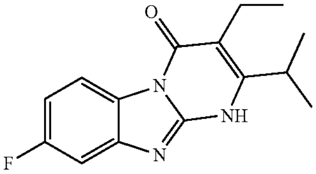
preferably
ca. 1:2
B-49
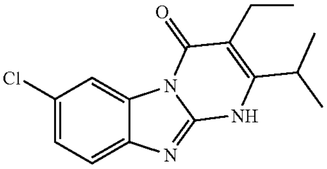
+
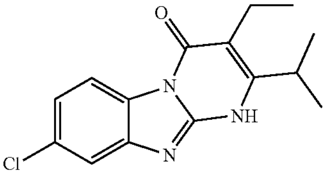
preferably
ca. 1:1
B-50
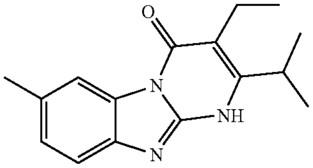
+
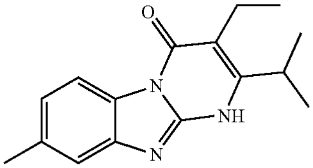

-continued
B-51
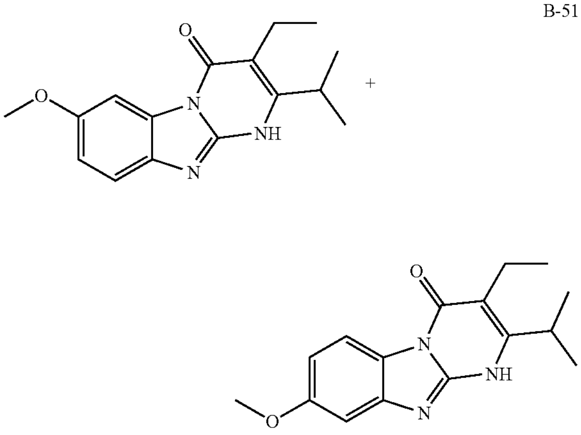
+
preferably
ca. 1:1.5
B-52
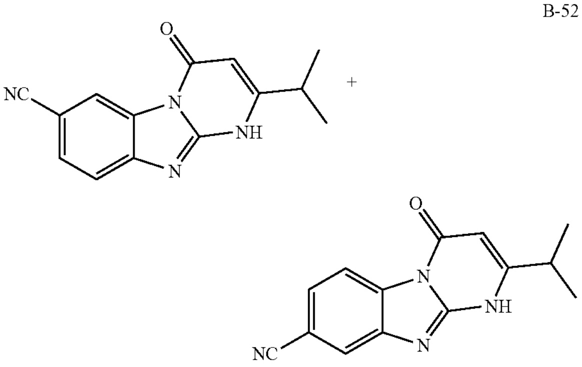
+
B-53
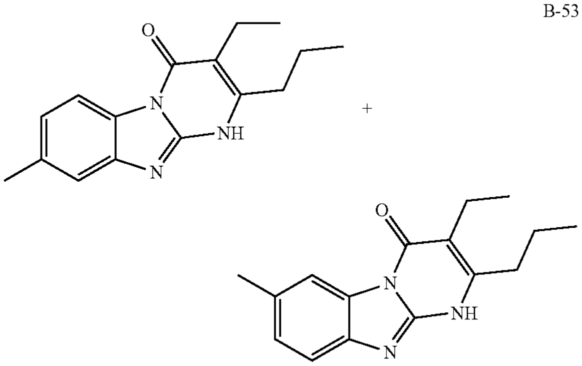
+
B-54
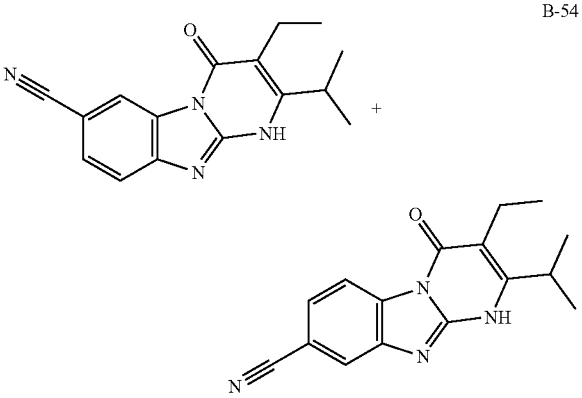
+
preferably
ca. 1.5:1
-continued
B-55
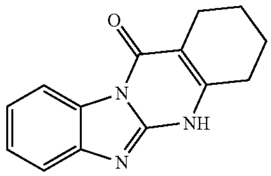
B-56
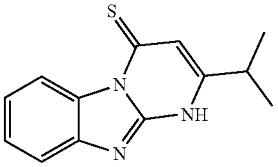
B-57
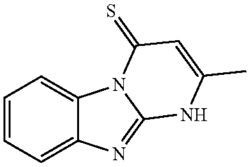
B-58
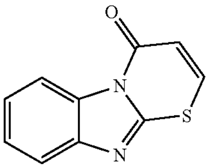
B-59
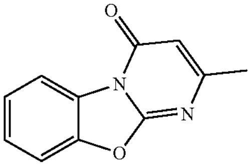
B-60
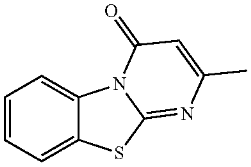
B-61
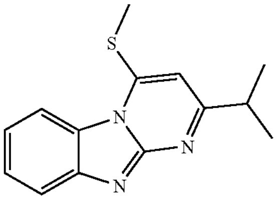
B-62
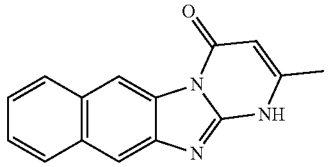

-continued
B-63
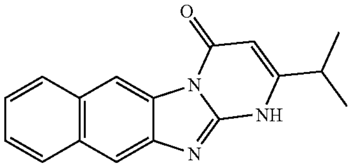
B-64
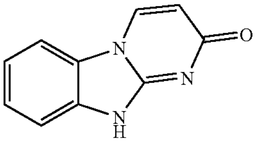
B-65
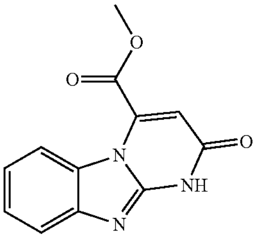
B-66
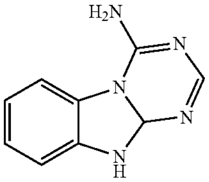
and
(III) C-67 to C-87 and the physiologically acceptable salts thereof:
C-67
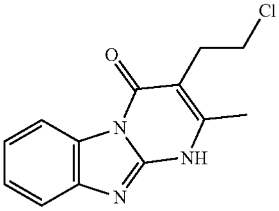
C-68
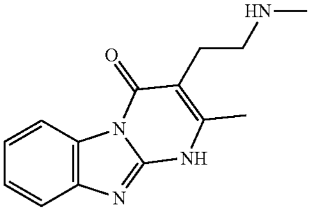
C-69
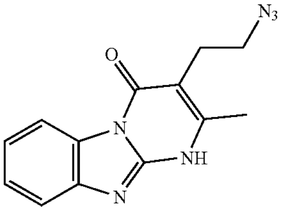
-continued
C-70
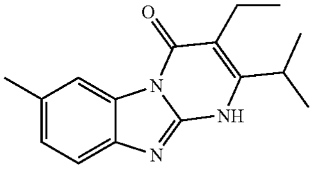
C-71
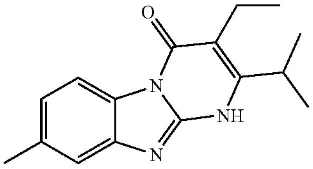
C-72
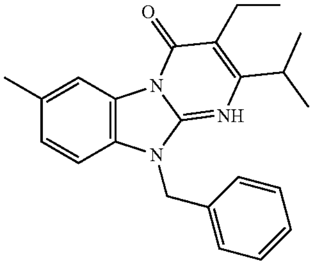
C-73
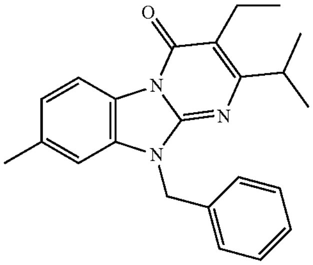
C-74
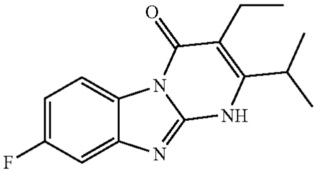
C-75
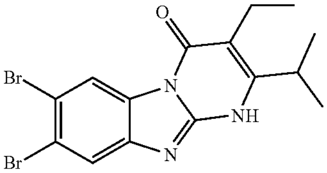
C-76
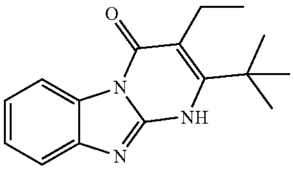
C-77
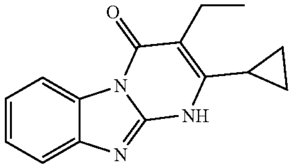

-continued
C-78
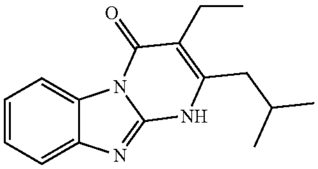
C-79
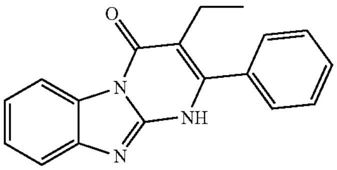
C-80
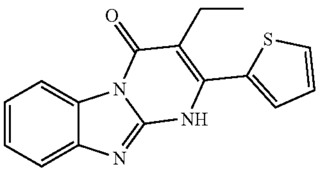
C-81
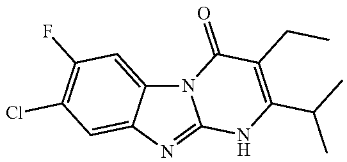
+
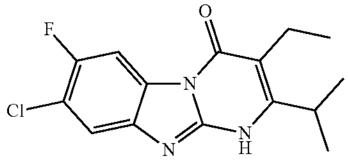
C-82
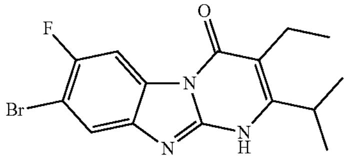
+
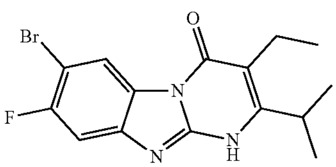
C-83
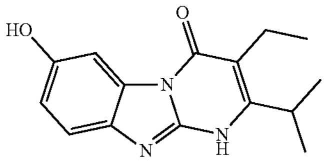
+
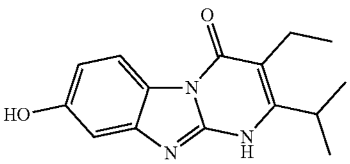
-continued
C-84
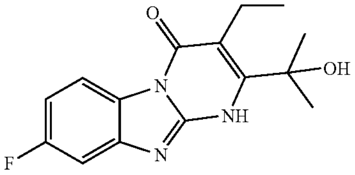
C-84*
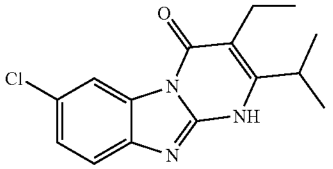
or
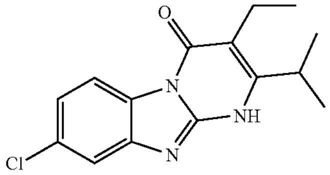
C-85
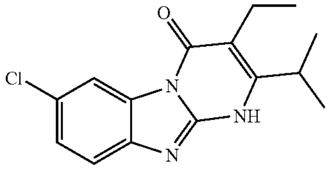
or
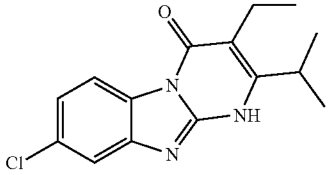
C-86
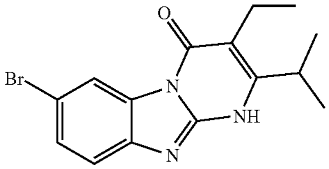
or
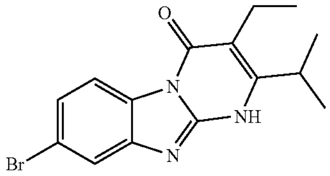
C-87
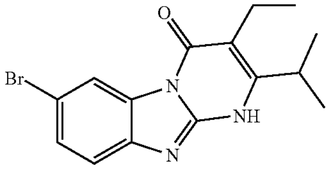
or
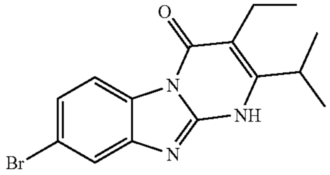

-continued

C-88

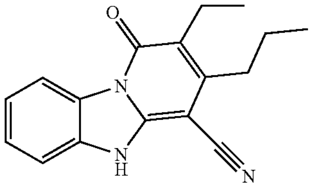

Preferably, the MrgX2 antagonist is administered orally.

Preferably, the MrgX2 antagonist is administered once daily, twice daily or thrice daily.

Another aspect of the invention relates to MrgX2 antagonist according to general formula (B)

(B)

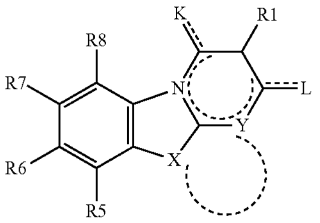

wherein

K means =O or =S, and L means —R2; or

K means —R2 and L means =O; and

X means —N= and Y means —NR3-; or

X means —NR4- and Y means —N=; or

X means —N= and Y means S; or

X means —O— and Y means —N=; or

X means —S— and Y means —N=; or

X means —N= and Y means —N=.

R1, R2, R3, R4 independently of one another mean —H; —$C_{1-6}$-alkyl; —$C_{1-6}$-cycloalkyl; -phenyl; —$C_{1-6}$-alkyl-phenyl; -heteroaryl selected from the group consisting of thienyl, furanyl and pyrrolyl; —C(=O)OH; —C(=O)O—$C_{1-6}$-alkyl; —CN; —OH; —O—$C_{1-6}$-alkyl; —F, —Cl, —Br, or —I; or R1 and R2 together with the atoms to which they are attached form a six membered saturated unsubstituted alicyclic ring;

wherein R5, R6, R7 and R8 independently of one another mean —H, —$C_{1-6}$-alkyl, —CN, —OH, —O—$C_{1-6}$-alkyl, —F, —Cl, —Br, —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "$C_{1-6}$-cycloalkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "phenyl" may be unsubstituted, mono- or disubstituted with a substituent independently selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "heteroaryl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

with the proviso that at least one of R5, R6, R7 and R8 does not mean —H; and/or at least three of R1, R2, R3, R4, R5, R6, R7 and R8 do not mean —H; and/or A-1, A-2, A-3, A-4, A-5, A-6, A-7, A-8, A-9, A-0, A-11, A-12, A-13, A-14, A-15, A-16, A-17, A-18, A-19, A-20, A-2, A-22, A-23, A-24, A-25, A-26, A-27, A-28, A-29 and/or A-30 are not included;

or a physiologically acceptable salt thereof.

A further aspect of the invention relates to an MrgX2 antagonist selected from compounds (II) B-31 to B-66 and the physiologically acceptable salts thereof:

B-31

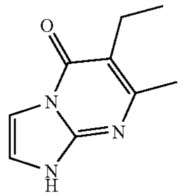

B-32

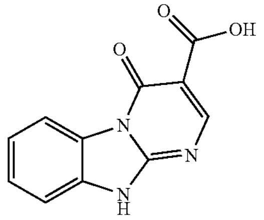

B-33

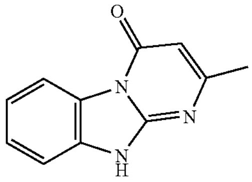

B-34

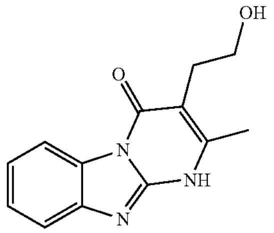

B-35

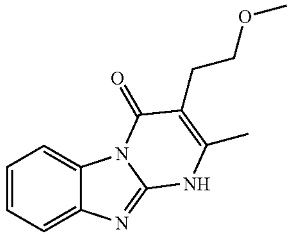

-continued
B-36
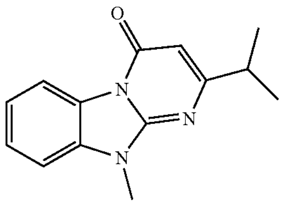
B-37
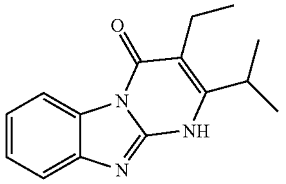
B-38
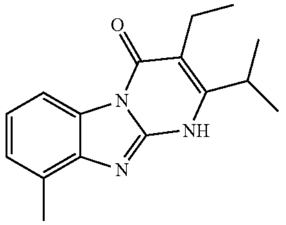
B-39
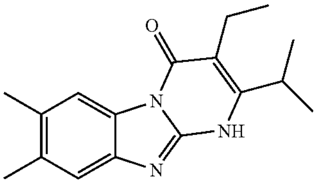
B-40
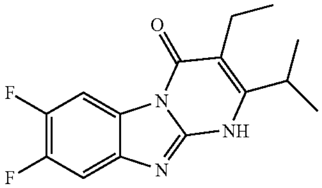
B-41
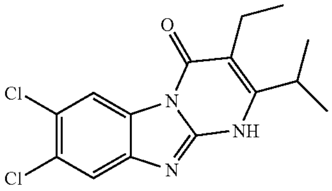
B-42
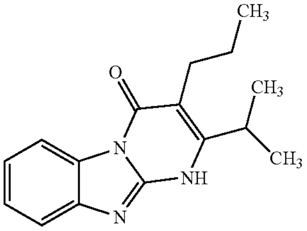
-continued
B-43
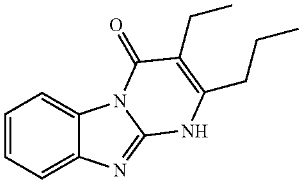
B-44
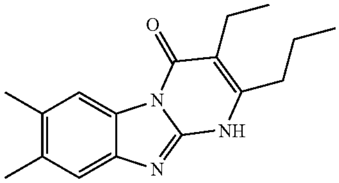
B-45
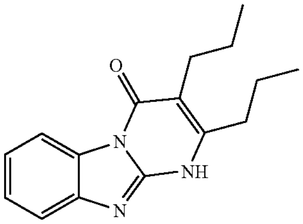
B-46
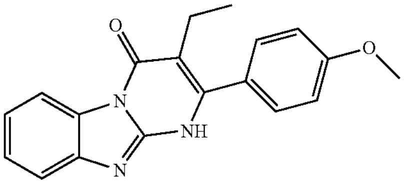
B-47
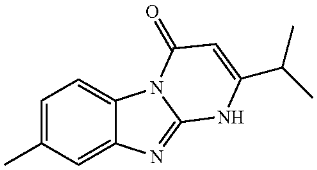
+
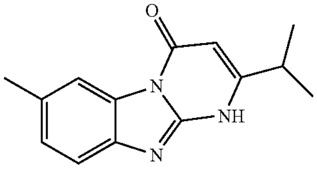
B-48
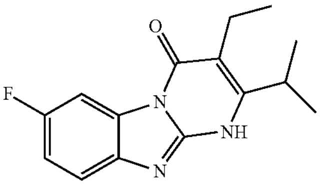
+
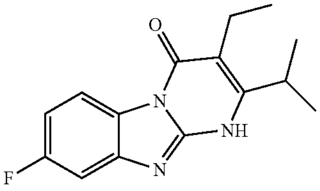
preferably ca.
1:2

-continued
B-49
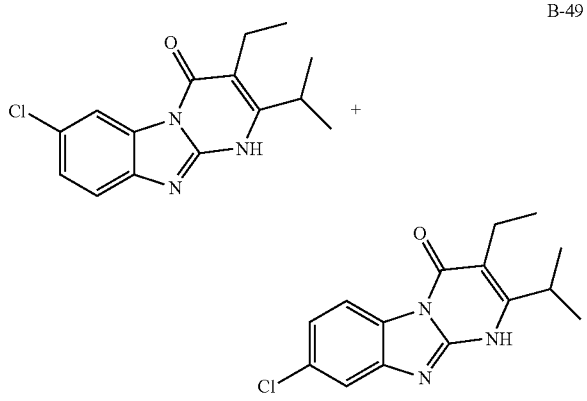
preferably ca.
1:1
B-50
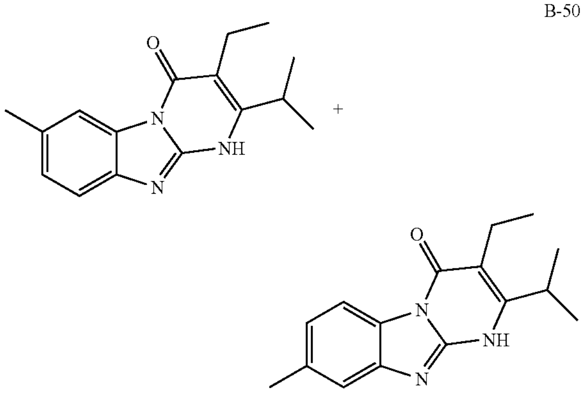
B-51
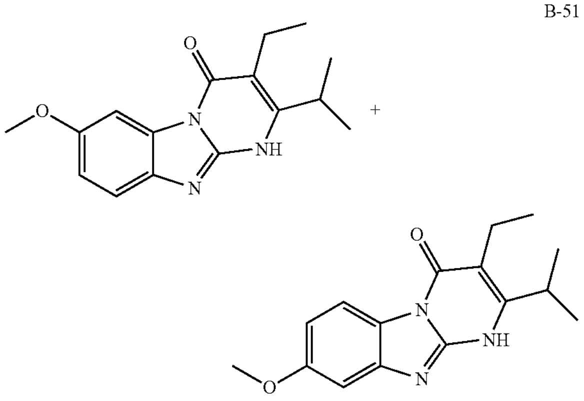
preferably ca.
1:1.5
B-52
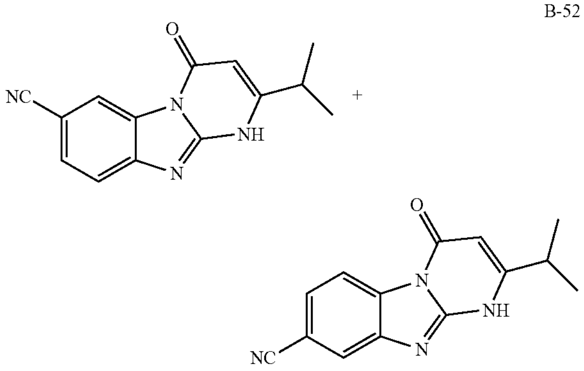
-continued
B-53
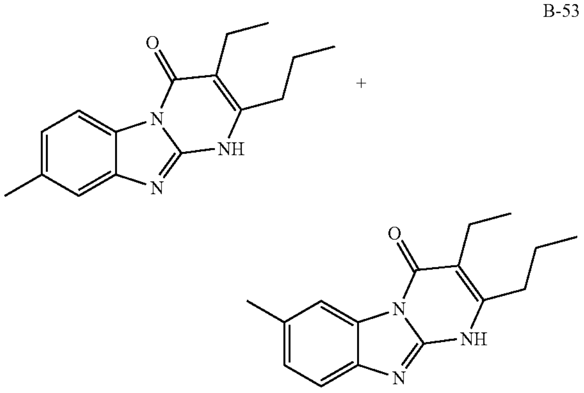
B-54
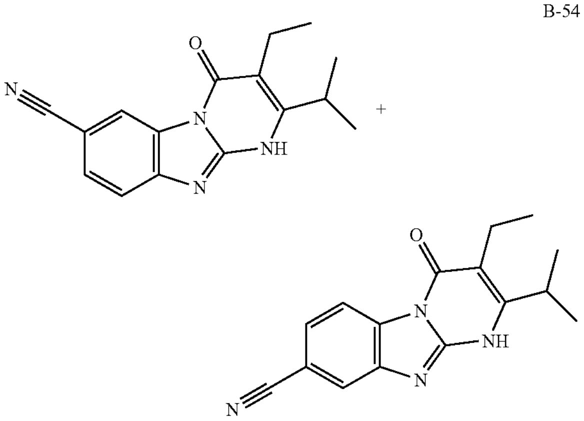
preferably ca.
1.5:1
B-55
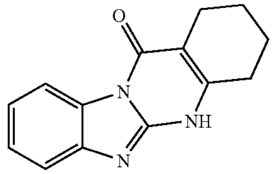
B-56
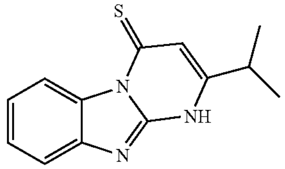
B-57
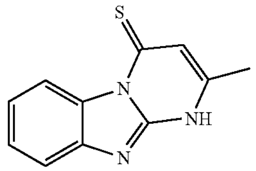
B-58
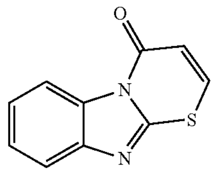

-continued
B-59
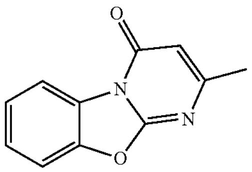
B-60
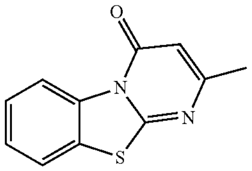
B-61
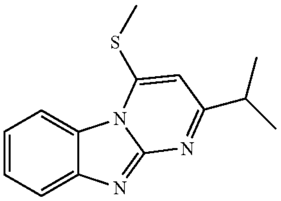
B-62
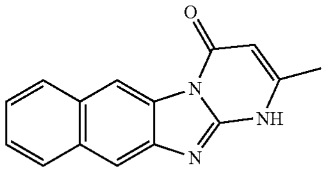
B-63
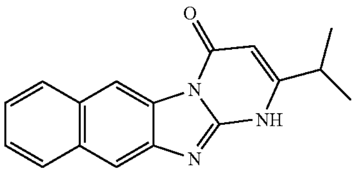
B-64
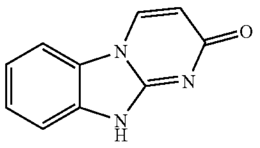
B-65
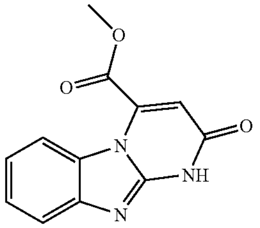
B-66
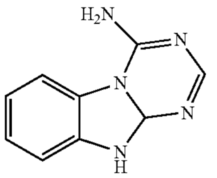
and
(III) C-67 to C-87 and the physiologically acceptable salts thereof:
C-67
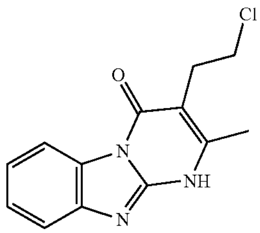
C-68
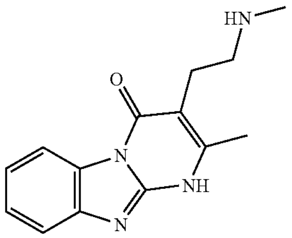
C-69
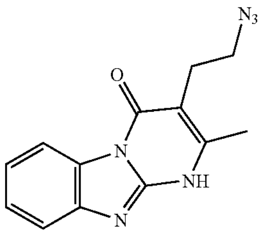
C-70
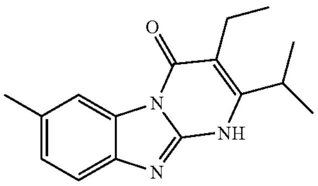
C-71
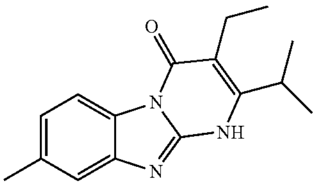
C-72
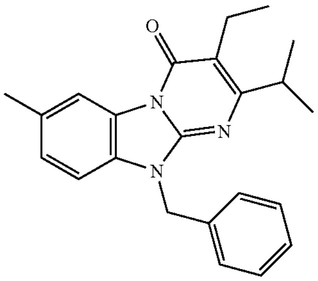

-continued
C-73
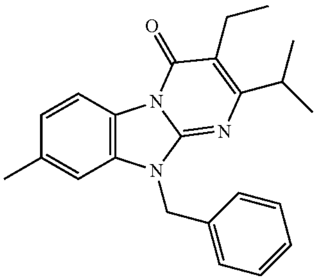
C-74
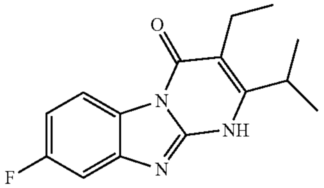
C-75
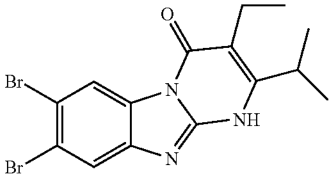
C-76
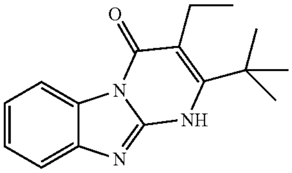
C-77
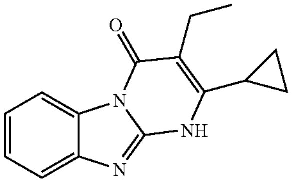
C-78
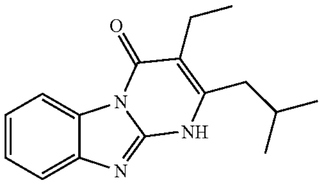
C-79
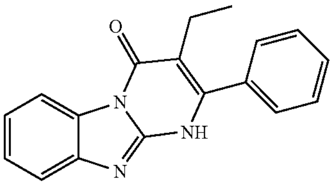
C-80
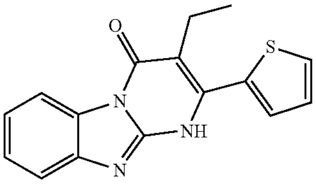
-continued
C-81
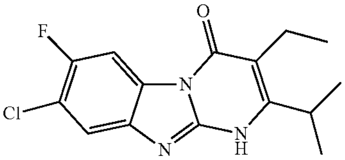
+
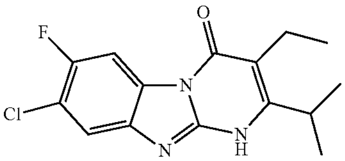
C-82
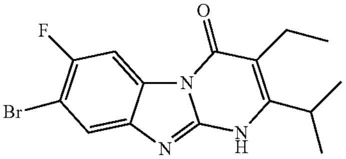
+
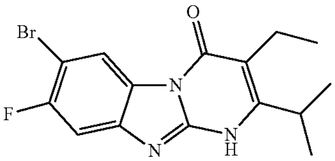
C-83
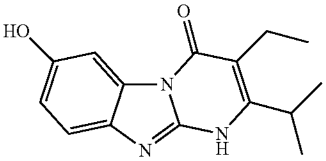
+
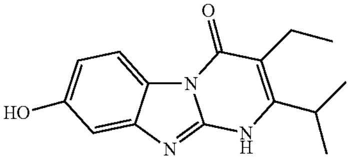
C-84
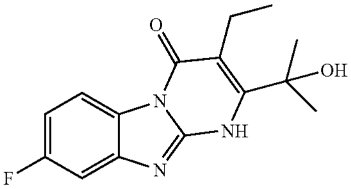
C-84*
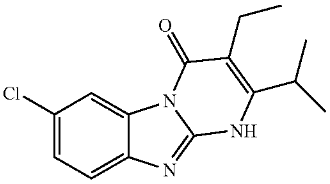
or
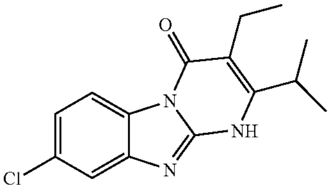

-continued

C-85

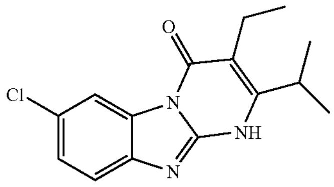

or

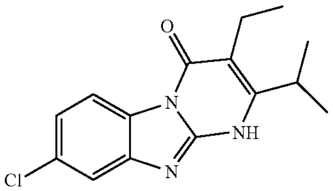

C-86

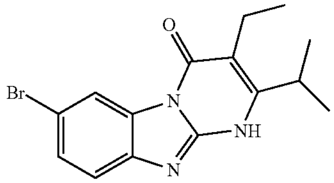

or

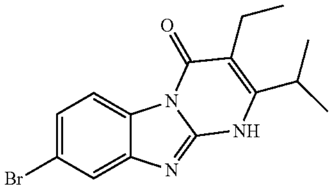

C-87

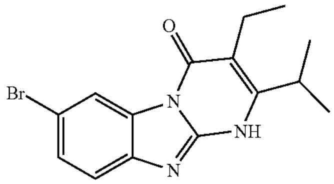

or

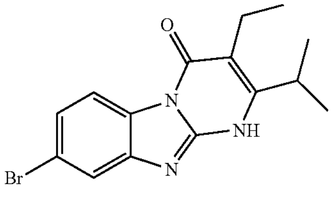

C-88

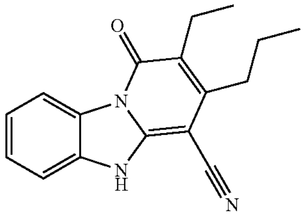

Another aspect of the invention relates to a pharmaceutical composition comprising (i) an MrgX2 antagonist according to general formula (B)

(B)

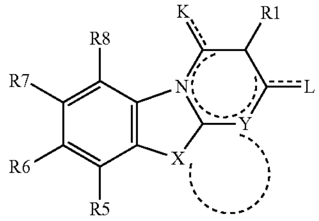

wherein

K means =O or =S, and L means —R2; or

K means —R2 and L means =O; and

X means —N= and Y means —NR3-; or

X means —NR4- and Y means —N=; or

X means —N= and Y means S; or

X means —O— and Y means —N=; or

X means —S— and Y means —N=; or

X means —N= and Y means —N=.

R1, R2, R3, R4 independently of one another mean —H; —$C_{1-6}$-alkyl; —$C_{1-6}$-cycloalkyl; -phenyl; —$C_{1-6}$-alkyl-phenyl; -heteroaryl selected from the group consisting of thienyl, furanyl and pyrrolyl; —C(=O)OH; —C(=O)O—$C_{1-6}$-alkyl; —CN; —OH; —O—$C_{1-6}$-alkyl; —F, —Cl, —Br, or —I; or R1 and R2 together with the atoms to which they are attached form a six membered saturated unsubstituted alicyclic ring;

wherein R5, R6, R7 and R8 independently of one another mean —H, —$C_{1-6}$-alkyl, —CN, —OH, —O—$C_{1-6}$-alkyl, —F, —Cl, —Br, —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "$C_{1-6}$-cycloalkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "phenyl" may be unsubstituted, mono- or disubstituted with a substituent independently selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "heteroaryl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

with the proviso that at least one of R5, R6, R7 and R8 does not mean —H; and/or at least three of R1, R2, R3, R4, R5, R6, R7 and R8 do not mean —H; and/or A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29 and/or A-30 are not included;

or a physiologically acceptable salt thereof; or (ii) an MrgX2 antagonist which is selected from any one of compounds (II) B-31 to B-66 and the physiologically acceptable salts thereof, or selected from any one of compounds (III) C-67 to C-87 and the physiologically acceptable salts thereof;

and a physiologically acceptable excipient.

Yet another aspect of the invention relates to a pharmaceutical dosage form comprising (i) an MrgX2 antagonist according to general formula (B)

(B)

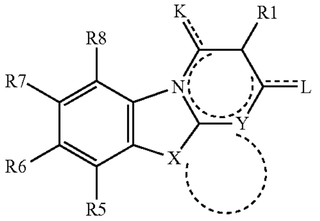

wherein

K means =O or =S, and L means —R2; or

K means —R2 and L means =O; and

X means —N= and Y means —NR3-; or

X means —NR4- and Y means —N=; or

X means —N= and Y means S; or

X means —O— and Y means —N=; or

X means —S— and Y means —N=; or

X means —N= and Y means —N=.

R1, R2, R3, R4 independently of one another mean —H; —$C_{1-6}$-alkyl; —$C_{1-6}$-cycloalkyl; -phenyl; —$C_{1-6}$-alkyl-phenyl; -heteroaryl selected from the group consisting of thienyl, furanyl and pyrrolyl;

—C(=O)OH; —C(=O)O—$C_{1-6}$-alkyl; —CN; —OH; —O—$C_{1-6}$-alkyl; —F, —Cl, —Br, or —I; or R1 and R2 together with the atoms to which they are attached form a six membered saturated unsubstituted alicyclic ring;

wherein R5, R6, R7 and R8 independently of one another mean —H, —$C_{1-6}$-alkyl, —CN, —OH, —O—$C_{1-6}$-alkyl, —F, —Cl, —Br, —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(=O)OH, —C(=O)O—$C_1$. 6-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "$C_{1-6}$-cycloalkyl" may be linear or branched, saturated or unsaturated, unsubstituted or monosubstituted with a substituent selected from —CN, —C(=O)OH, —C(=O)O—$C_1$. 6-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "phenyl" may be unsubstituted, mono- or disubstituted with a substituent independently selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "heteroaryl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

with the proviso that at least one of R5, R6, R7 and R8 does not mean —H; and/or at least three of R1, R2, R3, R4, R5, R6, R7 and R8 do not mean —H; and/or A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29 and/or A-30 are not included;

or a physiologically acceptable salt thereof; or (ii) an MrgX2 antagonist which is selected from anyone of compounds (II) B-31 to B-66 and the physiologically acceptable salts thereof; or selected from any one of compounds (III) C-67 to C-87 and the physiologically acceptable salts thereof;

or (iii) an MrgX2 antagonist according to general formula (B)

(B)

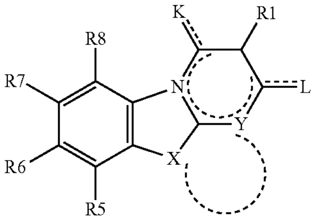

wherein

K means =O or =S, and L means —R2; or

K means —R2 and L means =O; and

X means —N= and Y means —NR3-; or

X means —NR4- and Y means —N=; or

X means —N= and Y means S; or

X means —O— and Y means —N=; or

X means —S— and Y means —N=; or

X means —N= and Y means —N=.

R1, R2, R3, R4 independently of one another mean —H; —$C_{1-6}$-alkyl; —$C_{1-6}$-cycloalkyl; -phenyl; —$C_{1-6}$-alkyl-phenyl; -heteroaryl selected from the group consisting of thienyl, furanyl and pyrrolyl;

—C(=O)OH; —C(=O)O—$C_{1-6}$-alkyl; —CN; —OH; —O—$C_{1-6}$-alkyl; —F, —Cl, —Br, or —I; or R1 and R2 together with the atoms to which they are attached form a six membered saturated unsubstituted alicyclic ring;

wherein R5, R6, R7 and R8 independently of one another mean —H, —$C_{1-6}$-alkyl, —CN, —OH, —O—$C_{1-6}$-alkyl, —F, —Cl, —Br, —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "$C_{1-6}$-cycloalkyl" may be linear or branched, saturated or unsaturated, unsubstituted or monosubstituted with a substituent selected from —CN, —C(=O)OH, —C(=O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "phenyl" may be unsubstituted, mono- or disubstituted with a substituent independently selected from —CN, —C(═O)OH, —C(═O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

wherein in each case the "heteroaryl" may be linear or branched, saturated or unsaturated, unsubstituted or monosubstituted with a substituent selected from —CN, —C(═O)OH, —C(═O)O—$C_{1-6}$-alkyl, —OH, —O—$C_{1-6}$-alkyl, —$NH_2$, —NH—$C_{1-6}$-alkyl, —N($C_{1-6}$-alkyl)$_2$, —$N_3$, —F, —Cl, —Br, —I;

with the proviso that at least one of R5, R6, R7 and R8 does not mean —H; and/or at least three of R1, R2, R3, R4, R5, R6, R7 and R8 do not mean —H; and/or A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29 and/or A-30 are not included;

or a physiologically acceptable salt thereof and further comprising a physiologically acceptable excipient; or (iv) an MrgX2 antagonist which is selected from any one of compounds (II) B-31 to B-66 and the physiologically acceptable salts thereof, or selected from any one of compounds (III) C-67 to C-87 and the physiologically acceptable salts thereof, and further comprising a physiologically acceptable excipient.

Preferably, the pharmaceutical dosage form is selected from tablets and capsules.

As used herein, the terms "physiologically acceptable salt" refer to those salts which retain the biological effectiveness and properties of the compound according to general formula (A), (B) and (C).

Such salts include, but are not restricted to: (1) an acid addition salt which is obtained by reaction of the free base of the compound according to general formula (A), (B) and (C) with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the compound according to general formula (A), (B) and (C) either is replaced by a metal ion, e.g., an alkali metal ion, such as sodium or potassium, an alkaline earth ion, such as magnesium or calcium, or an aluminum ion; or coordinates with an organic base such as ethanolamine, diethanolamine, triethanolamine, tromethamine, N-methylglucamine, and the like.

The compound of general formula (A), (B) and (C) may also act as a prodrug. A "prodrug" preferably refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial. A prodrug may be converted into the parent drug by various mechanisms, including enzymatic processes and metabolic hydrolysis.

A further example of a prodrug might be a short polypeptide, for example, without limitation, a 2-10 amino acid polypeptide, bonded through a terminal amino group to a carboxy group of a compound of this invention wherein the polypeptide is hydrolyzed or metabolized in vivo to release the active molecule. The prodrugs of compounds of general formula (A), (B) and (C) are within the scope of this invention.

Additionally, it is contemplated that compounds of general formula (A), (B) and (C) would be metabolized by enzymes in the body of the organism such as a human being to generate a metabolite that can modulate the activity of the MrgX2 receptor. Such metabolites are within the scope of the present invention.

Preferably, unless otherwise stated, the following terms used in the specification and claims have the following meanings:

Unless expressly stated otherwise, "alkyl" preferably refers to an aliphatic hydrocarbon including straight chain, or branched chain groups. Preferably, the alkyl group has 1 to 10 carbon atoms ($C_1$-$C_{10}$ alkyl), more preferably 1 to 6 carbon atoms ($C_1$-$C_6$ alkyl) and most preferably 1 to 4 carbon atoms ($C_1$-$C_4$ alkyl), e.g., methyl, ethyl, n-propyl, isopropyl, n-butyl, iso-butyl, sec-butyl, tert-butyl and the like. The aliphatic hydrocarbon may be saturated or unsaturated. When it is unsaturated, it may contain one or more unsaturations, i.e., —C═C-double and/or —C≡C-triple bonds. If there is more than one unsaturation, the unsaturations may be conjugated or isolated. Thus, for the purpose of the specification the term "alkyl" encompasses saturated hydrocarbons as well as alkenyl, alkynyl and alkenynyl residues. "Alkenyl" preferably refers to an alkyl group, as defined above, consisting of at least two carbon atoms and at least one carbon-carbon double bond e.g., ethenyl, propenyl, butenyl or pentenyl and their structural isomeric forms such as 1- or 2-propenyl, 1-, 2-, or 3-butenyl and the like. "Alkynyl" preferably refers to an alkyl group, as defined above, consisting of at least two carbon atoms and at least one carbon-carbon triple bond e.g., acetylene, ethynyl, propynyl, butynyl, or pentynyl and their structural isomeric forms as described above. Alkyl may be substituted or unsubstituted. When substituted, the substituent group(s) is one or more, for example one or two groups, individually selected from the group consisting of —$C_3$-$C_8$ cycloalkyl; —$C_6$-$C_{14}$ aryl; a 5-10 membered -heteroaryl wherein 1 to 4 ring atoms are independently selected from N, O or S; a 5-10 membered heterocycloalkyl wherein 1 to 3 ring atoms are independently selected from N, O or S; —OH; —O—$C_1$-$C_{10}$ alkyl (═$C_1$-$C_{10}$ alkoxy); —O—$C_8$-$C_8$cycloalkyl (═$C_3$-$C_8$ cycloalkoxy); —O—$C_6$-$C_{14}$ aryl (═$C_6$-$C_{14}$ aryloxy); —SH; —S—$C_1$-$C_{10}$ alkyl (=alkylthio); —S—$C_6$-$C_{14}$ aryl (═$C_6$-$C_{14}$ arylthio); —CN; -halo; -carbonyl; -thiocarbonyl; —O-carbamyl; —N-carbamyl; —O— thiocarbamyl; —N-thiocarbamyl; —C-amido; —N-amido; —C-carboxy; —O-carboxy; —$NO_2$; -silyl; -sulfinyl; -sulfonyl; and —$NR^bR^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or $R^b$ and $R^c$, together with the nitrogen atom to which they are attached, combine to form a five- or six-membered heterocyclo-alkyl ring. Preferably, the substituent(s) is/are independently selected from -chloro, -fluoro, -bromo, -hydroxy, -methoxy, -nitro, -carboxy, -methoxycarbonyl, -sulfonyl, or -amino.

Unless expressly stated otherwise, "cycloalkyl" preferably refers to cyclic hydrocarbon residue that contains no heteroatoms as ring members and that is not aromatic. "Cyclo-alkyl" may encompass a single cycle or more than one cycle. Preferably, cycloalkyl has 3 to 8 carbon atoms (—$C_3$-$C_8$ cycloalkyl).

Cycloalkyl may be saturated, e.g., cyclopropane, cyclobutane, cyclopentane, cyclohexane, cycloheptane, adamantane; or unsaturated (e.g., cycloalkenyl, cycloalkynyl), e.g., cyclobutenyl, cyclopentenyl, cyclohexenyl, cyclo-hexadiene, cycloheptatriene and the like. Cycloalkyl may be substituted or unsubstituted. When substituted, the substituent group(s) is one or more, for example one or two groups, individually selected from —$C_1$-$C_{10}$ alkyl; —$C_3$-$C_8$ cycloalkyl; —$C_6$-$C_{14}$ aryl; 5-10 membered-heteroaryl wherein 1 to 4 ring atoms are independently selected from N, O or S; 5-10 membered -heterocycloalkyl wherein 1 to 3 ring atoms are independently selected from N, O or S; —OH; —O—$C_1$-$C_{10}$ alkyl; —O—$C_3$-$C_8$ cycloalkyl; —O—$C_6$-$C_{14}$ aryl; —SH; —S—$C_1$-$C_{10}$ alkyl; —S—$C_6$-$C_{14}$ aryl; —CN; -halo; -carbonyl; thiocarbonyl; —O-carbamyl; —N-carbamyl; —O-thiocarbamyl; —N-thiocarbamyl; —C-amido; —N-amido; —C-carboxy; —O-carboxy; —$NO_2$; -silyl; -sulfinyl; -sulfonyl; and —$NR^bR^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or $R^b$ and $R^c$, together with the nitrogen atom to which they are attached, combine to form a five- or six-membered heterocycloalkyl ring. Preferably, the substituent(s) is/are independently selected from -chloro, -fluoro, -bromo, -methyl, -ethyl, -hydroxy, -methoxy, -nitro, -carboxy, -methoxycarbonyl, -sulfonyl, or -amino.

Unless expressly stated otherwise, "heterocycloalkyl" preferably refers to a monocyclic or fused ring of 5 to 10 ring atoms containing one, two, or three heteroatoms in the ring which are selected from the group consisting of N, O and —S(O)n where n is 0-2, the remaining ring atoms being carbon. The rings may be saturated or unsaturated, i.e. the rings may have one or more double bonds. However, the rings are not aromatic (heterocycloalkyl≠heteroaryl). Examples, without limitation, of heterocycloalkyl groups are pyrrolidine, piperidine, piperazine, morpholine, imidazolidine, tetrahydropyridazine, tetrahydrofuran, thiomorpholine, tetrahydropyridine, and the like. Heterocycloalkyl may be substituted or unsubstituted. When substituted, the substituted group(s) is one or more, for example one, two, or three substituents, independently selected from the group consisting of —$C_1$-$C_{10}$ alkyl; —$C_3$-$C_8$ cycloalkyl; —$C_6$-$C_{14}$ aryl; 5-10 membered -heteroaryl wherein 1 to 4 ring atoms are independently selected from N, O or S; 5-10 membered -heterocycloalkyl wherein 1 to 3 ring atoms are independently selected from N, O or S; —OH; —$C_1$-$C_{10}$ alkyl; —O—$C_3$-$C_8$ cycloalkyl; —O—$C_6$-$C_{14}$ aryl; —SH; —S—$C_1$-$C_{10}$ alkyl; —S—$C_6$-$C_{14}$ aryl; —CN; -halo; -carbonyl; -thiocarbonyl; —O-carbamyl; —N-carbamyl; —O-thiocarbamyl; —N-thiocarbamyl; —C-amido; —N-amido; —C-carboxy; —O-carboxy; —$NO_2$; -silyl; -sulfinyl; -sulfonyl; and —$NR^bR^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or R and R, together with the nitrogen atom to which they are attached, combine to form a five- or six-membered heterocycloalkyl ring. Preferably, the substituent(s) is/are independently selected from -chloro, -fluoro, -bromo, -methyl, -ethyl, -hydroxy, -methoxy, -nitro, -carboxy, -methoxycarbonyl, -sulfonyl, or -amino.

Unless expressly stated otherwise, "aryl" preferably refers to an aromatic all-carbon monocyclic or fused-ring polycyclic group (i.e., rings which share adjacent pairs of carbon atoms) of 6 to 14 ring atoms and having a completely conjugated pi-electron system. Examples, without limitation, of aryl groups are phenyl, naphthalenyl and anthracenyl. The aryl group may be substituted or unsubstituted. When substituted, the substituted group(s) is one or more, for example one, two, or three substituents, independently selected from the group consisting of —$C_1$-$C_{10}$ alkyl; —$C_3$-$C_8$ cycloalkyl; —$C_6$-$C_{14}$ aryl; 5-10 membered -heteroaryl wherein 1 to 4 ring atoms are independently selected from N, O or S; 5-10 membered -heterocycloalkyl wherein 1 to 3 ring atoms are independently selected from N, O or S; —OH; —O—$C_1$-$C_{10}$ alkyl; —O—$C_3$-$C_8$ cycloalkyl; —O—$C_6$-$C_{14}$ aryl; —SH; —S—$C_1$-$C_{10}$ alkyl; —S—$C_6$-$C_{14}$ aryl; —CN; -halo; carbonyl; -thiocarbonyl; —O-carbamyl; —N-carbamyl; —O-thiocarbamyl; —N-thiocarbamyl; —C-amido; —N-amido; —C-carboxy; —O-carboxy; —$NO_2$; -silyl; -sulfinyl; -sulfonyl; and —$NR^bR^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or $R^b$ and $R^c$, together with the nitrogen atom to which they are attached, combine to form a five- or six-membered heterocycloalkyl ring.

Preferably the substituent(s) is/are independently selected from -chloro, -fluoro, -bromo, -methyl, -ethyl, -hydroxy, -methoxy, -nitro, -carboxy, -methoxycarbonyl, -sulfonyl, or -amino.

Unless expressly stated otherwise, "heteroaryl" preferably refers to a monocyclic or fused aromatic ring (i.e., rings which share an adjacent pair of atoms) of 5 to 10 ring atoms in which one, two, three or four ring atoms are selected from the group consisting of N, O and S and the rest being carbon. Examples, without limitation, of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benz¬oxazolyl, quinolizinyl, quinazolinyl, pthalazinyl, quinoxalinyl, cinnnolinyl, napthyridinyl, quinolyl, isoquinolyl, tetrazolyl, 5,6,7,8-tetrahydroquinolyl, 5, 6, 7, 8-tetra-hydroisoquinolyl, purinyl, pteridinyl, pyridinyl, pyrimidinyl, carbazolyl, xanthenyl or benzoquinolyl. The heteroaryl group may be substituted or unsubstituted. When substituted, the substituted group(s) is one or more, for example one or two substituents, independently selected from the group consisting of —$C_1$-$C_{10}$ alkyl; —$C_3$-$C_8$ cycloalkyl; —$C_6$-$C_{14}$ aryl; 5-10 membered -heteroaryl wherein 1 to 4 ring atoms are independently selected from N, O or S; 5-10 membered -heterocycloalkyl wherein 1 to 3 ring atoms are independently selected from N, O or S; —OH; —O—$C_1$-$C_{10}$ alkyl; —O—$C_3$-$C_8$ cycloalkyl; —O—$C_6$-$C_{14}$ aryl; —SH; —S—$C_1$-$C_{10}$ alkyl; —S—$C_6$-$C_{14}$ aryl; —CN; -halo; -carbonyl; -thiocarbonyl; —O-carbamyl; —N-carbamyl; —O-thiocarbamyl; —N-thiocarbamyl; —C-amido; —N-amido; —C-carboxy; —O-carboxy; —$NO_2$; -silyl; -sulfinyl; -sulfonyl; and —$NR^bR^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or $R^b$ and $R^c$, together with the nitrogen atom to which they are attached, combine to form a five- or six-membered heterocycloalkyl ring. Preferably the substituent(s) is/are independently selected from -chloro, -fluoro, -bromo, -methyl, -ethyl, -hydroxy, -methoxy, -nitro, -carboxy, -methoxy-carbonyl, -sulfonyl, or -amino.

"Hydroxy" preferably refers to an —OH group.

"Alkoxy" preferably refers to an —O-unsubstituted alkyl and —O-substituted alkyl group, as defined herein. Examples include and are not limited to -methoxy, -ethoxy, -propoxy, -butoxy, and the like.

"Cycloalkoxy" preferably refers to an O cycloalkyl group, as defined herein. One example is -cyclopropyloxy.

"Aryloxy" preferably refers to both an —O-aryl and an —O-heteroaryl group, as defined herein. Examples include and are not limited to -phenoxy, -napthyloxy, -pyridyloxy, -furanyloxy, and the like.

"Mercapto" preferably refers to an —SH group.

"Alkylthio" preferably refers to both an —S-alkyl and an —S-cycloalkyl group, as defined herein. Examples include and are not limited to -methylthio, -ethylthio, and the like.

"Arylthio" preferably refers to both an —S-aryl and an —S-heteroaryl group, as defined herein.

Examples include and are not limited to -phenylthio, -napthylthio, -pyridylthio, -furanylthio, and the like.

"Sulfinyl" preferably refers to a —S(═O)—$R^a$ group, wherein, $R^a$ is selected from the group consisting of —H; —OH; -alkyl, -cycloalkyl, -aryl, -heteroaryl (bonded through a ring carbon) and -heterocycloalkyl (bonded through a ring carbon), as defined herein.

"Sulfonyl" preferably refers to a —S(═O)$_2$—$R^a$ group wherein, $R^a$ is selected from the group consisting of —H, —OH, -alkyl, -cycloalkyl, -aryl, -heteroaryl (bonded through a ring carbon) and -heterocycloalkyl (bonded through a ring carbon), as defined herein.

"Trihalomethyl" preferably refers to a —$CX_3$ group wherein X is a halo group as defined herein e.g., -trifluoromethyl, -trichloromethyl, -tribromomethyl, -dichlorofluoromethyl, and the like.

"Carbonyl" preferably refers to a —C(═O)—$R^a$ group, where $R^a$ is selected from the group consisting of —H, -alkyl, -cycloalkyl, -aryl, -heteroaryl (bonded through a ring carbon) and -heterocycloalkyl (bonded through a ring carbon), as defined herein. Representative examples include and the not limited to -acetyl, -propionyl, -benzoyl, -formyl, -cyclopropylcarbonyl, -pyridinylcarbonyl, -pyrrolidin-1-yl-carbonyl, and the like.

"Thiocarbonyl" preferably refers to a —C(═S)—$R^a$ group, with $R^a$ as defined herein.

"C-carboxy" and "carboxy" which are used interchangeably herein preferably refer to a —C(═O)O—$R^a$ group, with $R^a$ as defined herein, e.g. COOH, -methoxycarbonyl, -ethoxy-carbonyl, -benzyloxycarbonyl, and the like.

"O-carboxy" preferably refers to a —OC(═O)$R^a$ group, with $R^a$ as defined herein, e.g. -methylcarbonyloxy, -phenylcarbonyloxy, -benzylcarbonyloxy, and the like.

"Acetyl" preferably refers to a —C(═O)$CH_3$ group.

"Carboxylic acid" preferably refers to a —C(═O)O$R^a$ group in which $R^a$ is —H.

"Halo" or "halogen" preferably refers to -fluorine, -chlorine, -bromine or -iodine.

"Cyano" preferably refers to a —CN group.

"Nitro" preferably refers to a —$NO_2$ group.

"O-carbamyl" preferably refers to a —OC(═O)N$R^b$$R^c$ group, with $R^b$ and $R^c$ as defined herein.

"N-carbamyl" preferably refers to a $R^c$OC(═O)N$R^b$— group, with $R^b$ and $R^c$ as defined herein.

"O-thiocarbamyl" preferably refers to a —OC(═S)N$R^b$ $R^c$ group, with $R^b$ and $R^c$ as defined herein.

"N-thiocarbamyl" preferably refers to a $R^c$OC(═S)N$R^b$— group, with $R^b$ and $R^c$ as defined herein.

"Amino" preferably refers to an —N$R^b$$R^c$ group, wherein $R^b$ and $R^c$ are independently —H or unsubstituted $C_1$-$C_6$ alkyl, e.g, —$NH_2$, -dimethylamino, -diethylamino, -ethyl-amino, -methyl-amino, and the like.

"C-amido" preferably refers to a —C(═O)N$R^b$$R^c$ group, with $R^b$ and $R^c$ as defined herein. For example, $R^b$ is —H or unsubstituted —$C_1$-$C_4$ alkyl and R is —H, —$C_1$-$C_4$ alkyl optionally substituted with -heterocycloalkyl, -hydroxy, or -amino. For example, —C(═O)N$R^b$$R^c$ may be -aminocarbonyl, -dimethyl-aminocarbonyl, -diethylaminocarbonyl, -diethylamino-ethylaminocarbonyl, -ethylaminoethyl-amino-carbonyl, and the like.

"N-amido" preferably refers to a $R^c$C(═O)N$R^b$— group, with $R^b$ and $R^c$ as defined herein, e.g. -acetylamino, and the like.

If not expressly stated otherwise, any residue, group or moiety defined herein that can be substituted is preferably substituted with one or more substituents independently selected from the group consisting of —$C_1$-$C_{10}$ alkyl; —$C_3$-$C_8$ cycloalkyl; —$C_6$-$C_{14}$ aryl; 5-10 membered -heteroaryl wherein 1 to 4 ring atoms are independently selected from N, O or S; 5-10 membered -heterocycloalkyl wherein 1 to 3 ring atoms are independently selected from N, O or S; —OH; —O—$C_1$-$C_{10}$ alkyl; —O—$C_3$-$C_8$ cycloalkyl; —O—$C_6$-$C_{14}$ aryl; —SH; —S—$C_1$-$C_{10}$ alkyl; —S—$C_6$-$C_{14}$ aryl; —CN; -halo; -carbonyl; -thiocarbonyl; —O-carbamyl; —N-carbamyl; —O-thio-carbamyl; —N-thiocarbamyl; —C-amido; —N-amido; —C-carboxy; —O-carboxy; —$NO_2$; silyl; -sulfinyl; -sulfonyl; and —N$R^b$$R^c$ where $R^b$ and $R^c$ are independently selected from the group consisting of —H, —$C_1$-$C_4$ alkyl, —$C_3$-$C_8$ cycloalkyl, —$C_6$-$C_{14}$ aryl, -carbonyl, -acetyl, -sulfonyl, -amino, and trifluoromethanesulfonyl; or $R^b$ and $R^c$, together with the nitrogen atom to which they are attached, combine to form a five- or six-membered heterocyclo-alkyl ring. Preferably the substituent(s) is/are independently selected from -chloro, -fluoro, -bromo, -methyl, -ethyl, -hydroxy, -methoxy, -nitro, -carboxy, -methoxycarbonyl, -sulfonyl, or -amino.

The invention also relates to the stereoisomers of the compounds according to general formula (A), (B) and (C) e.g. the enantiomers or diastereomers in racemic, enriched or substantially pure form.

In another aspect, the present invention relates to a pharmaceutical composition comprising any of the compounds or salts of the present invention and, optionally, a pharmaceutically acceptable carrier or excipient. This composition may additionally comprise further compounds or medicaments, such as, for example, neuroprotective or antinociceptive agents besides the compounds according to general formula (A), (B) and (C).

"Pharmaceutical composition" preferably refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Physiologically or pharmaceutically acceptable carriers and excipients are known to the skilled person. In this regard it can be referred to, e.g., H. P. Fiedler, Lexikon der Hilfsstoffe für Pharmazie, Kosmetik und angrenzende technische Gebiete, Editio Cantor Aulendorf, 2001.

The pharmaceutical composition according to the invention can be, e.g., solid, liquid or pasty.

A further aspect of the invention relates to a pharmaceutical dosage form comprising the pharmaceutical composition according to the invention.

The pharmaceutical dosage form according to the invention may be adapted for various routes of administration (e.g. systemic, parenteral, topic, local), such as oral administration, infusion, injection and the like.

Pharmaceutical dosage forms that are adapted for oral administration include tablets, pellets, capsules, powders, granules and the like.

The pharmaceutical dosage form is preferably adapted for administration once daily, twice daily or thrice daily. The pharmaceutical dosage form may release the compound according to general formula (A), (B) and (C) immediately (immediate release formulation) or over an extended period of time (retarded release, delayed release, prolonged release, sustained release, and the like).

The compounds according to the invention show agonistic or antagonistic effects at the MrgX2 receptors. They may among other indications be used as antinociceptive and/or antipruritic drugs.

In another aspect, the invention relates to the use of the compounds according to general formula (A), (B) and (C) for activating or antagonizing MrgX2 receptor function. Thus, in one embodiment, the compounds of the invention may be used as antinociceptive drugs. In a further aspect, the compounds according to general formula (A), (B) and (C) may thus also be used for the prevention, alleviation and/or treatment of a disease or disorder related to MrgX2 receptor activity.

The terms "diseases and disorders related to MrgX2 receptor function", "diseases and disorders connected to MrgX2 receptor function" and "disease or disorder related to MrgX2 receptor activity" are used interchangeably herein to refer to a condition involving MrgX2 receptor activity. Examples for such diseases and disorders are neurodegenerative diseases, nociceptive pain, and neuropathic pain.

Since the adenine receptor is also expressed in brain, e.g. in the cortex, also included are CNS disorders, such as neuroinflammatory conditions and neurodegenerative disorders (e.g. Alzheimer's and Parkinson's disease).

"Treat", "treating" and "treatment" preferably refer to a method of alleviating or abrogating an MrgX2 receptor related disease or disorder and/or its attendant symptoms.

"Prevent", "preventing" and "prevention" preferably refer to a method of hindering an MrgX2 receptor related disease or disorder from occurring, i.e. a prophylactic method.

"Organism" preferably refers to any living entity comprised of at least one cell. A living organism can be as simple as, for example, a single eukaryotic cell or as complex as a mammal, including a human being.

"Therapeutically effective amount" preferably refers to that amount of the compound being administered which will relieve to some extent one or more of the symptoms of the disorder being treated.

Preferably, the subject afflicted by a disease treated, alleviated or prevented according to the invented use is a human.

A further aspect of the invention relates to the use of a compound according to general formula (A), (B) and (C) for the manufacture of a pharmaceutical composition according to the invention or of a pharmaceutical dosage form according to the invention for preventing, ameliorating or treating pain or a prutitus.

The inventions illustratively described herein may suitably be practiced in the absence of any element or elements, limitation or limitations, not specifically disclosed herein. Thus, for example, the term "includes" shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The present inventions will be explained in more detail in the following examples. However, the examples are only used for illustration and do not limit the scope of the present invention.

For all reactions, analytical grade solvents were used. $^{1}H$, $^{13}C$ and $^{19}F$ NMR spectra were recorded using spectrometers: Bruker Avance 300 ($^{1}H$ NMR: 300 MHz, $^{13}C$ NMR: 75 MHz), Bruker Avance 500 ($^{1}H$ NMR: 500 MHz, $^{13}C$ NMR: 125 MHz, $^{19}F$ NMR: 470 MHz) or Bruker Avance 600 (H NMR: 600 MHz, $^{13}C$ NMR: 150 MHz). Chemical shifts (6) are reported in ppm relative to tetramethylsilane (TMS) or residual solvent signal for $^{1}H$, residual solvent signal for $^{13}C$ and trifluoroacetic acid (−77.0 ppm) for $^{19}F$ NMR. Abbreviations used are: s=singlet, d=doublet, t=triplet, q=quartet, sept=septet, dt=doublet of triplets, dq=doublet of quartets, td=triplet of doublets, ddd=doublet of doublet of doublets, m=multiplet, br=broad. Coupling constants are expressed in Hz. High resolution mass spectra were acquired on a quadrupole orthogonal acceleration time-of-flight mass spectrometer (Synapt G2 HDMS, Waters, Milford, MA). Samples were infused at 3 µL-min- and spectra were obtained in positive (or negative) ionization mode with a resolution of 15000 (FWHM) using leucine enkephalin as lock mass. Precoated aluminum sheets (Fluka Silica gel/TLC-cards, 254 nm) were used for TLC. Flash column chromatography was performed on ICN silica gel 63-200 mesh, 60 Å.

Synthesis of 2-alkyl-3-oxoesters

Scheme. Synthesis of 2-alkyl-3-oxoesters.

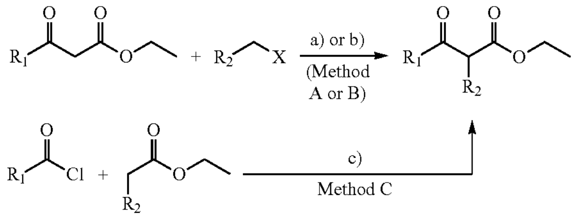

X = I or Br

Reagents and conditions: a) NaH, THF, rt; b) $K_2CO_3$, DMF, rt; c) BuLi, DIPEA, THF, -78° C. to rt.

TABLE

Overview of the synthesized 3-oxoesters.

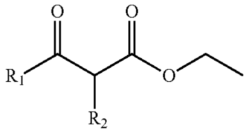

| Entry | $R_1$ | $R_2$ |
|---|---|---|
| 1 | isopropyl (methylethyl) | ethyl |
| 2 | tert-butyl (1,1-dimethylethyl) | ethyl |
| 3 | phenyl | ethyl |
| 4 | cyclopropyl | ethyl |
| 5 | isobutyl (2-methylpropyl) | ethyl |
| 6 | propyl | ethyl |
| 7 | isopropyl (methylethyl) | propyl |
| 8 | propyl | propyl |
| 9 | methyl | 2-methoxyethyl |
| 10 | p-methoxyphenyl | ethyl |

Method A:

Appropriate 3-oxoester (1.0 equiv.) was added to a suspension of NaH (60% in mineral oil, 1.0 mol. equiv.) in THF (1 ml/1 mmol of 3-oxoester) at room temperature and resulting mixture was stirred for 30 min at room temperature. Then alkyl halide (1 mol. equiv.) was added and mixture was refluxed for defined period of time (TLC control). After cooling to room temperature reaction was quenched with saturated aqueous $NH_4Cl$ (1.2 ml/1 mmol of NaH). The aqueous layer was separated and extracted with AcOEt (3×). Organic layers were combined, dried over $MgSO_4$, filtered and concentrated in vacuo (at 30° C.). The crude product was purified by flash column chromatography on silica gel giving colorless liquid which was pure enough to be used in the next step without additional purification and fraction contaminated with starting material which was not further purified.

Method B:

A mixture of 3-oxoester (1 mol. equiv.), alkyl halide (1.1 mol. equiv.) and $K_2CO_3$ (1.5 mol. equiv.) in DMF (2.5 ml/1 ml of 3-oxoester) was stirred at room temperature overnight. Next, $H_2O$ (10 vol of DMF) was added and mixture was extracted with AcOEt (3×). Organic layers were combined, dried over $MgSO_4$, filtered and concentrated in vacuo (at 30° C.). The crude product was purified by flash column chromatography on silica gel giving colorless liquid which was pure enough to be used in the next step without additional purification and fraction contaminated with starting material which was not further purified.

Method C:

To a solution of butyl lithium (2.3 mol equiv.) in THF at −78° C., was added diisopropylamine (DIPEA; 2.4 mol equiv.) dropwise. The mixture was stirred at −78° C. for half an hour. Ethyl ester (2 mol equiv.) was added dropwise via cannula over 30 minutes and the mixture was allowed to stir further at −78° C. Lastly acid chloride (1 mol equiv.) was added dropwise to the reaction mixture and after addition the reaction was heated to room temperature and allowed to stir for another 2 hours. After reaction completion the reaction was quenched using saturated $NH_4Cl$ solution and the mixture was extracted three times with AcOEt. The combined organic layers were dried using $Na_2SO_4$, filtered and concentrated in vacuo. The crude product was purified by flash column chromatography on silica gel yielding a colorless to light yellow oil.

Ethyl 2-ethyl-4-methyl-3-oxopentanoate

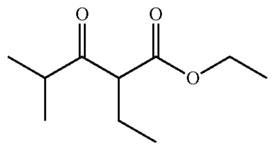

Chemical Formula: $C_{10}H_{18}O_3$

The title compound was obtained from ethyl isobutyrylacetate (2.50 g; 15.80 mmol) and ethyl iodide according to Method A in 90% yield (2.64 g, 14.17 mmol). $^1H$ NMR ($CDCl_3$, 300 MHz): δ (ppm) 0.92 (t, J=7.4 Hz, 3H), 1.10 (d, J=6.9 Hz, 3H), 1.12 (d, J=6.9 Hz, 3H), 1.26 (t, J=7.1 Hz, 3H), 1.87 (dq, J=7.4, 7.3 Hz, 2H), 2.80 (sept, J=6.9 Hz, 1H), 3.53 (t, J=7.3 Hz, 3H), 4.18 (q, J=7.1 Hz, 2H). $^{13}C$ NMR ($CDCl_3$, 75 MHz): δ (ppm) 12.18, 14.22, 18.16, 18.45, 21.84, 40.72, 58.77, 61.26, 169.90, 209.26.

Ethyl 2-ethyl-4,4-dimethyl-3-oxopentanoate

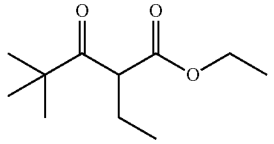

The title compound was obtained from trimethylacetyl chloride (0.50 g; 4.15 mmol) and ethyl butanoate according to Method C in 38% yield (320 mg, 1.60 mmol). $^1H$ NMR ($CDCl_3$, 300 MHz): δ (ppm) 0.91 (t, J=7.4 Hz, 3H), 1.17 (s, 9H), 1.24 (t, J=7.5 Hz, 3H), 1.80 (m, 2H), 3.80 (t, J=7.1 Hz, 1H), 4.13 (q, J=7.1 Hz, 2H).

Ethyl 2-benzoylbutanoate

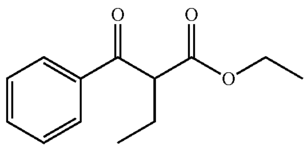 [SMILES: CCOC(=O)C(CC)C(=O)c1ccccc1]

The title compound was obtained from benzoyl chloride (0.50 g; 3.56 mmol) and ethyl butanoate according to Method C and the crude was used in the next reaction without further purification.

Ethyl 2-(cyclopropanecarbonyl)butanoate

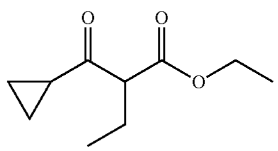

The title compound was obtained from cyclopropanecarbonyl chloride (0.50 g; 4.78 mmol) and ethyl butanoate according to Method C in 26% yield (320 mg, 1.25 mmol). $^1$H NMR ($CDCl_3$, 300 MHz): δ (ppm) 0.95 (t, J=7.4 Hz, 3H), 1.09 (m, 2H), 1.27 (t, J=7.1 Hz, 3H), 1.94 (q, J=7.4 Hz, 2H), 2.07 (m, 1H), 3.47 (t, J=7.4 Hz, 1H), 4.21 (q, J=7.1 Hz, 2H).

Ethyl 2-ethyl-5-methyl-3-oxohexanoate

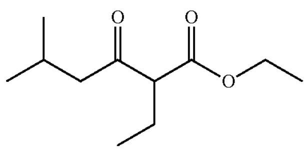

The title compound was obtained from 3-methylbytyryl chloride (0.50 g; 4.15 mmol) and ethyl butanoate according to Method C in 58% yield (490 mg, 2.45 mmol). $^1$H NMR ($CDCl_3$, 300 MHz): δ (ppm) 0.89 (m, 9H), 1.28 (t, J=7.2 Hz, 3H), 1.55 (m, 3H), 1.68-1.94 (m, 2H), 2.39-2.55 (m, 1H), 4.18 (dd, J=8.7, 5.7 Hz, 2H).

Ethyl 2-ethyl-3-oxohexanoate

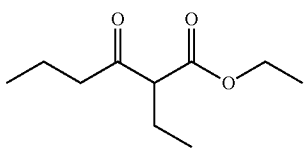

The title compound was obtained from ethyl butyrylacetate (1.496 ml; 1.48 g; 9.353 mmol) and ethyl iodide according to Method A in 76% yield (1.320 g, 7.087 mmol) as a colorless liquid. $^1$H NMR ($CDCl_3$, 300 MHz): δ (ppm) 0.91 (t, J=7.5 Hz, 3H), 0.92 (t, J=7.5 Hz, 3H), 1.27 (t, J=7.2 Hz, 3H), 1.62 (sext, J=7.5 Hz, 2H), 1.83-1.92 (m, 2H), 2.44 (m, 1H), 2.54 (m, 1H), 3.35 (t, J=7.2 Hz, 1H), 4.19 (q, J=7.2 Hz, 2H). $^{13}$C NMR ($CDCl_3$, 75 MHz): δ (ppm) 12.06, 13.68, 14.22, 17.02, 21.70, 43.87, 60.84, 61.28, 169.98, 205.50.

Ethyl 4-methyl-3-oxo-2-propylpentanoate

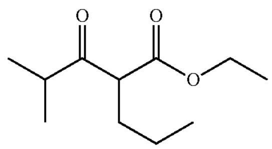

The title compound was obtained from ethyl isobutyrylacetate (2 mmol) and propyl iodide according to Method A in 68% (273 mg, 1.363 mmol) yield as a colorless liquid. $^1$H NMR ($CDCl_3$, 300 MHz): δ (ppm) 0.93 (t, J=7.3 Hz, 3H), 1.10 (d, J=6.9 Hz, 3H), 1.11 (d, J=6.9 Hz, 3H), 1.23-1.34 (m, 5H), 1.78-1.86 (m, 2H), 2.77 (sept, J=6.9 Hz, 1H), 3.61 (t, J=7.3 Hz, 1H), 4.17 (q, J=7.1 Hz, 2H). $^{13}$C NMR ($CDCl_3$, 75 MHz): δ (ppm) 12.98, 13.22, 17.22, 17.49, 29.52, 39.67, 56.05, 60.29, 169.02, 208.34.

Ethyl 3-oxo-2-propylhexanoate

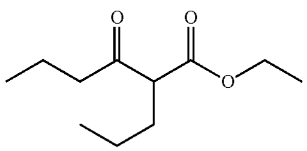

Chemical Formula: $C_{11}H_{20}O_3$
Exact Mass: 200.14

To a mixture of ethyl 3-oxohexanoate (1 mmol) in THF (5 ml) was added t-BuOK (1.1 mmol) and the mixture was stirred for 15 min at room temperature. Then alkyl halide (1 mmol) was added dropwise and mixture was stirred at room temperature overnight. After that time TLC control showed presence of mainly starting material. Mixture was brought to reflux and kept refluxing for 20 h. Then it was poured into saturated aqueous $NH_4Cl$ (50 ml) and extracted with AcOEt (3×). Organic layers were combined, dried over $MgSO_4$, filtered and concentrated in vacuo. The crude product was purified by flash column chromatography on silica gel ($CH_2Cl_2$) affording 99 mg of colorless liquid (0.494 mmol, 49%) which was pure enough to be used in the next step. $^1$H NMR ($CDCl_3$, 300 MHz): δ (ppm) 0.91 (t, J=7.5 Hz, 3H), 0.92 (t, J=7.2 Hz, 3H), 1.24-1.37 (m, 5H), 1.51-1.66 (m, 2H), 1.70-1.75 (m, 2H), 3.46 (t, J=7.5 Hz, 1H), 4.18 (q, J=7.2 Hz, 2H). $^{13}$C NMR ($CDCl_3$, 75 MHz): δ (ppm) 12.68, 12.93, 13.22, 16.04, 19.83, 29.35, 42.79, 58.11, 60.28, 169.10, 204.54.

Ethyl 2-acetyl-4-methoxybutanoate

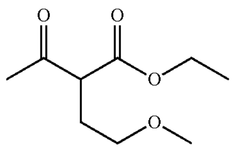

The title compound was obtained from ethyl acetoacetate (1.25 mmol) and 1-bromo-2-methoxyethane according to Method A in 74% yield (174 mg, 0.925 mmol) as a yellow liquid. $^{1}H$ NMR ($CDCl_3$, 300 MHz): δ (ppm) 1.28 (t, J=7.2 Hz, 3H), 2.08-2.16 (m, 2H), 2.26 (s, 3H), 3.29 (s, 3H), 3.37-3.41 (m, 2H), 3.64 (t, J=6.9 Hz, 1H), 4.20 (q, J=7.2 Hz, 2H). $^{13}C$ NMR ($CDCl_3$, 75 MHz): δ (ppm) 14.19, 28.21, 29.38, 56.34, 58.69, 61.49, 70.05, 169.79, 203.15.

Ethyl 2-(4-methoxybenzoyl)butanoate

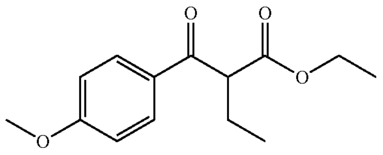 [SMILES: CCOC(=O)C(CC)C(=O)c1ccc(OC)cc1]

The title compound was obtained from 2.0 mmol of ethyl 3-(4-methoxyphenyl)-3-oxopropanoate and ethyl iodide according to Method A in 65% yield (325 mg, 1.298 mmol) as a colorless liquid. $^{1}H$ NMR ($CDCl_3$, 300 MHz): δ (ppm) 0.98 (t, J=7.5 Hz, 3H), 1.18 (t, J=7.2 Hz, 3H), 1.98-2.08 (m, 2H), 3.87 (s, 3H), 4.11-4.20 (m, 2H), 6.95 (d, J=8.7 Hz, 2H), 7.98 (d, J=9.0 Hz, 2H). $^{13}C$ NMR ($CDCl_3$, 75 MHz): δ (ppm) 12.25, 14.17, 22.58, 24.88, 55.62, 55.77, 114.01, 129.57, 131.06, 163.92, 170.32, 193.76.

Synthesis of 2-aminoimidazole derivatives

Scheme. Synthesis of 2-aminoimidazole derivatives.

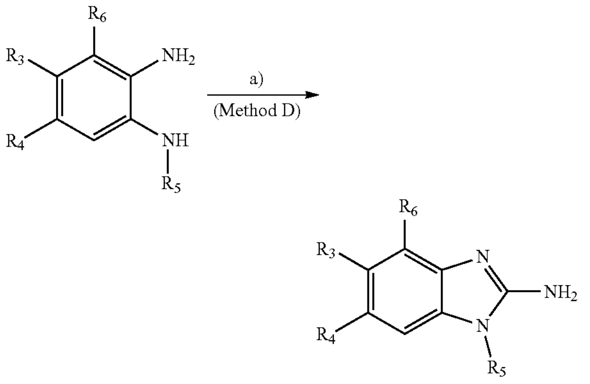

Reagents and conditions: a) BrCN, EtOH, 50° C.

TABLE

Overview of the synthesized 2-aminobenzimidazole derivatives

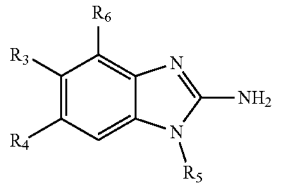

| Entry | $R_3$ | $R_4$ | $R_5$ | $R_6$ |
|---|---|---|---|---|
| 1 | F | F | H | H |
| 2 | Cl | Cl | H | H |
| 3 | Br | Br | H | H |
| 4* | Me | Me | H | H |
| 5 | H | H | H | Me |
| 6 | Me (H) | H (Me) | H | H |
| 7 | CN (H) | H (CN) | H | H |
| 8 | Cl (H) | H (Cl) | H | H |
| 9 | F (H) | H (F) | H | H |
| 10 | OMe (H) | H (OMe) | H | H |
| 11 | Me | H | Bn | H |
| 12 | H | Me | Bn | H |

*Product isolated as hydrobromide salt.

Method D:

To an appropriate aromatic diamino compound (1 mol. equiv.) in EtOH (4.5 ml/1 mmol starting material) was added cyanogen bromide (1.2 mol. equiv.) and resulting mixture was stirred at 50° C. till disappearance of starting material (TLC control). Then volatiles were removed in vacuo and the solid residue was re-dissolved (or suspended) in $H_2O$. Water mixture was extracted with EtOAc (3×). Organic layer was discarded and water layer was brought to pH 9-10 (according to universal indicator paper) using 25% $NH_4OH$ or 1 M aqueous NaOH and it was extracted with EtOAc (3×). Combined organic layers were dried over $MgSO_4$. Drying agent was removed, residue was concentrated to dryness and purified on silica gel column if needed.

5,6-Difluoro-1H-benzo[d]imidazol-2-amine

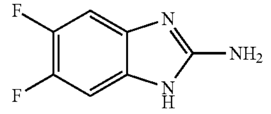

Chemical Formula: $C_7H_5F_2N_3$
Exact Mass: 169.05

The title compound was synthesized from 1,2-diamino-4,5-difluorobenzene (500 mg, 3.47 mmol) according to the Method D. Purification of crude product on silica gel column (4-6% of MeOH in $CH_2Cl_2$ with 2% (v/v) addition of 7 N ammonia in MeOH) afforded 459 mg (2.71 mmol; 78%) of product as a pale brown solid. $^{1}H$ NMR (DMSO-$d_6$, 600 MHz): δ (ppm) 6.31 (br, 2H), 7.05-7.08 (m, 2H). $^{13}C$ NMR (DMSO-$d_6$, 150 MHz): δ (ppm) 99.63, 134.3 (br), 144.6 (dd, J=232.4 Hz, J=15.1 Hz), 156.99. $^{19}F$ NMR (DMSO-$d_6$, 470 MHz): δ (ppm) −150.2 $^{1}H$ NMR ($CD_3OD$, 600 MHz): δ (ppm) 4.94 (br, 2H), 7.01 (t, J=9.0 Hz, 2H). $^{13}C$ NMR ($CD_3OD$, 150 MHz): δ (ppm) 100.1 (d, J=15.1 Hz), 134.6 (br), 147.3 (dd, J=236.9 Hz, J=16.6 Hz), 158.14. $^{19}F$ NMR ($CD_3OD$, 470 MHz): δ (ppm) −150.7 (t, J=8.7 Hz). HRMS (ESI): m/z $[M+H]^+$ calcd for $C_7H_6F_2N_3$: 170.0524, found 170.0531.

5,6-Dichloro-1H-benzo[d]imidazol-2-amine

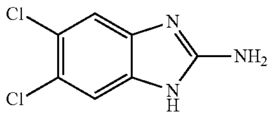

Chemical Formula: $C_7H_5Cl_2N_3$
Exact Mass: 200.99

The title compound was synthesized from 1,2-diamino-4,5-dichlorobenzene (500 mg, 2.82 mmol) according to the Method D affording 568 mg (quant.) of product as a pale yellow solid (without column purification). H NMR (DMSO-$d_6$, 300 MHz): δ (ppm) 6.58 (s, 2H), 7.27 (s, 2H). $^{13}C$ NMR (DMSO-$d_6$, 75 MHz): δ (ppm) 112.35, 120.76, 138.78, 157.12. HRMS (ESI): m/z $[M+H]^+$ calcd for $C_7H_6Cl_2N_3$: 201.9933, found 201.9934.

5,6-Dibromo-1H-benzo[d]imidazol-2-amine

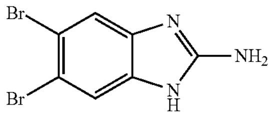

Chemical Formula: $C_7H_5Br_2N_3$
Exact Mass: 288.89

The title product was synthesized from 4,5-dibromo-1,2-diaminobenzene (100 mg, 0.376 mmol) according to the Method D. Purification by silica gel column chromatography (3-10% of MeOH in $CH_2Cl_2$) afforded 100 mg (0.343 mmol, 91%) of product as a white solid. $^1H$ NMR (DMSO-$d_6$, 300 MHz) δ (ppm) 6.93 (br, 2H), 7.46 (s, 2H).

5,6-Dimethyl-1H-benzo[d]imidazol-2-amine hydrobromide

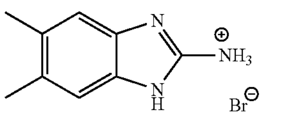

Chemical Formula: $C_9H_{12}BrN_3$
Exact Mass: 241.02

Product was synthesized from 1,2-diamino-4,5-dimethylbenzene based on the Method D. After addition of concentrated aqueous $NH_3$ product was still present in $H_2O$. Water layer was concentrated and solid residue was purified on silica gel column (20% of MeOH in $CH_2Cl_2$ with 2% vol. addition of 7 N ammonia in MeOH) affording 676 mg (2.792 mmol; 76%) of product as a pale yellow solid. $^1H$ NMR (DMSO-$d_6$, 300 MHz): δ (ppm) 2.26 (s, 6H), 7.11 (s, 2H), 7.97 (br, 2H). $^{13}C$ NMR (DMSO-$d_6$, 75 MHz): δ (ppm) 19.61, 111.90, 129.07, 130.57, 150.66. HRMS (ESI): m/z $[M+H]^+$ calcd for $C_9H_{12}N_3$: 162.1026. found 162.1033.

4-Methyl-1H-benzo[d]imidazol-2-amine

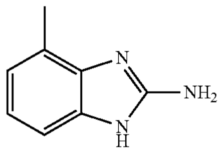

Chemical Formula: $C_8H_9N_3$
Exact Mass: 147.08

The title compound was synthesized from 1,2-diamino-3-methylbenzene (500 mg, 4.09 mmol) according to the Method D. Purification of crude product on silica gel column (4-5% of MeOH in $CH_2Cl_2$ with 2% vol. addition of 7 N ammonia in MeOH) afforded 327 mg (2.22 mmol; 54%) of product as a pale orange solid. $^1H$ NMR (DMSO-$d_6$, 300 MHz): δ (ppm) 2.34 (s, 3H), 6.08 (br, 2H), 6.67 (d, J=7.2 Hz, 1H), 6.75 (t, J=7.5 Hz, 1H), 6.93 (d, J=7.5 Hz, 1H). $^{13}C$ NMR (DMSO-$d_6$, 75 MHz): δ (ppm) 16.61, 108.77, 118.84, 120.07, 121.15, 137.17, 138.37, 154.76. HRMS (ESI): m/z $[M+H]^+$ calcd for $C_8H_{10}N_3$: 148.0869, found 148.0874.

5-Methyl-1H-benzo[d]imidazol-2-amine

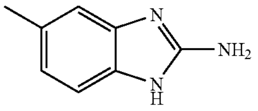

Chemical Formula: $C_8H_9N_3$
Exact Mass: 147.08

The title product was synthesized from 1,2-diamino-4-methylbenzene (500 mg, 4.093 mmol) according to the Method D affording 596 mg (4.049 mmol, 96%) of product as red-brown solid. $^1H$ NMR (DMSO-$d_6$, 300 MHz): δ (ppm) 2.30 (s, 3H), 6.08 (br, 2H), 6.67 (d, J=7.8 Hz, 1H), 6.91 (s, 1H), 6.96 (d, J=7.8 Hz, 1H). $^{13}C$ NMR (DMSO-$d_6$, 75 MHz): δ (ppm) 21.19, 111.03, 111.89, 119.92, 127.67, 136.34, 138.77, 155.01. HRMS (ESI): m/z $[M+H]^+$ calcd for $C_8H_{10}N_3$: 148.0869, found: 148.0861.

2-Amino-1H-benzo[d]imidazole-5-carbonitrile

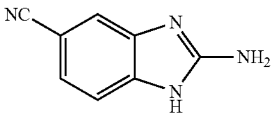

Chemical Formula: $C_8H_6N_4$
Exact Mass: 158.06

The title product was obtained from 3,4-diaminobenzonitrile (500 mg, 3.76 mmol) with slightly modified Method D. After removal of volatiles, solid residue was redissolved in $H_2O$ and pH was adjusted to 8-9 using 5 N aqueous NaOH. Precipitate that formed was filtered-off, washed with $H_2O$ and dried under vacuum. Filtrate and washings were combined and extracted with EtOAc (3×). Combined organic layers were dried over MgSO4. After removal of drying agent and solvent residue was put on silica gel column (8% of MeOH in $CH_2Cl_2$ with 2% vol. addition of 7 N ammonia MeOH) affording additional 77 mg of product. Total yield: 590 mg (3.73 mmol, 99%) of product as a grey solid. $^1H$ NMR (DMSO-$d_6$, 300 MHz): δ (ppm) 6.67 (bs, 2H), 7.20 (d, J=7.8 Hz, 1H), 7.27 (d, J=7.8 Hz, 1H). $^{13}C$ NMR (DMSO-$d_6$, 75 MHz): δ (ppm) 100.01, 112.43, 114.34, 120.88, 123.86, 138.16, 143.67, 157.67. HRMS (ESI): m/z $[M+H]^+$ calcd for $C_8H_7N_4$: 159.0665, found: 159.0669.

5-Chloro-1H-benzo[d]imidazol-2-amine

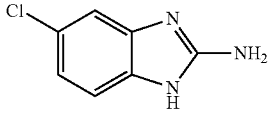

Chemical Formula: $C_7H_6ClN_3$
Exact Mass: 167.03

The title compound was synthesized from 4-chloro-1,2-diaminobenzene (500 mg, 3.51 mmol) according to the Method D. Purification of crude product by silica gel column chromatography (5-10% of MeOHOH in $CH_2Cl_2$ with 2% vol. addition of 7 N ammonia in MeOH) afforded 512 mg (3.05 mmol; 87%) of product as a brown solid. $^1H$ NMR (DMSO-$d_6$, 300 MHz): δ (ppm) 6.36 (bs, 2H), 6.85 (dd, 1H, J=8.1 Hz, J=1.8 Hz), 7.07 (t, J=8.4 Hz, 1H), 7.10 (d, J=1.8 Hz, 1H). $^{13}C$ NMR (DMSO-$d_6$, 75 MHz): δ (ppm) 111.63, 111.75, 118.46, 123.26, 136.80, 140.86, 156.37. HRMS (ESI): m/z $[M+H]^+$ calcd for $C_7H_7ClN_3$: 168.0323, found 168.0329.

5-Fluoro-1H-benzo[d]imidazol-2-amine

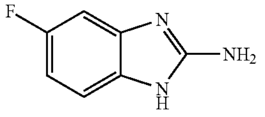

Chemical Formula: $C_7H_6FN_3$
Exact Mass: 151.05

The title compound was synthesized from 1,2-diamino-4-fluorobenzene (500 mg, 3.96 mmol) according to the Method D. Crude product was suspended in a mixture of $CH_2Cl_2$ and cyclohexane, precipitate was filtered-off, washed with cyclohexane and dried affording 502 mg (3.32 mmol; 84%) of product as a brown solid. $^1H$ NMR (DMSO-$d_6$, 600 MHz): δ (ppm) 6.26 (s, 2H), 6.62-6.66 (m, 1H), 6.88 (dd, dd, J=9.6, 1.6 Hz, 1H), 7.03 (dd, J=6.4, 5.4 Hz, 1H). $^{13}C$ NMR (DMSO-$d_6$, 150 MHz): δ (ppm) 99.3 (d, J=25.6 Hz), 105.4 (d, J=24.1 Hz), 110.57, 133.71 (br), 141.00 (br), 156.68, 157.6 (d, J=229.4 Hz). $^{19}F$ NMR (DMSO-$d_6$, 470 MHz): δ (ppm) −124.5 (br). $^1H$ NMR ($CD_3OD$, 600 MHz): δ (ppm) 4.92 (bs, 2H), 6.70 (ddd, J=10.2, 8.4, 2.4 Hz, 1H), 6.89 (dd, J=9.6, 2.4 Hz, 1H), 7.07 (dd, J=8.4, 4.2 Hz, 1H). $^{13}C$ NMR ($CD_3OD$, 150 MHz): δ (ppm) 100.2 (d, J=27.2 Hz), 107.8 (d, J=25.6 Hz), 112.1 (d, J=10.6 Hz), 134.26, 140.64, 158.4 (d, J=226.4 Hz), 160.7. $^{19}F$ NMR ($CD_3OD$, 470 MHz): δ (ppm) −(125.64-125.59) (td, J=9.6 Hz, J=4.6 Hz). HRMS (ESI): m/z $[M+H]^+$ calcd for $C_7H_7FN_3$: 152.0618, found 152.0621.

5-Methoxy-1H-benzo[d]imidazol-2-amine

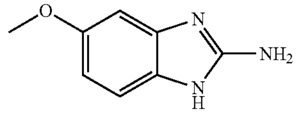

Chemical Formula: $C_8H_9N_3O$
Exact Mass: 163.07

The title compound was synthesized from 1,2-diamino-4-methoxybenzene (500 mg, 3.62 mmol) according to the general procedure. Purification of crude product on FC (6-10% of $CH_3OH$ in $CH_2Cl_2$ with 1% vol. addition of 7N $NH_3/CH_3OH$) afforded 451 mg (2.77 mmol; 76%) of product as a pale brown solid. $^1H$ NMR (DMSO-$d_6$, 300 MHz): δ (ppm) 3.70 (s, 3H), 6.10 (bs, 2H), 6.48 (dd, J=8.4, 2.4 Hz, 1H), 6.70 (d, J=2.4 Hz, 1H), 6.97 (d, J=8.4 Hz, 1H). $^{13}C$ NMR (DMSO-$d_6$, 75 MHz): δ (ppm) 55.38, 97.58, 106.07, 110.91, 131.81, 140.03, 153.91, 155.25. HRMS (ESI): m/z $[M+H]^+$ calcd for $C_8H_{10}N_3O$: 164.0818, found 164.0827.

Synthesis of Substituted imidazo[1,2-a]pyrimidin-5 (1H)-ones, benzo[4,5]imidazo[1,2-a]pyrimidin-4 (10H)-one derivatives and some 4(10H)-thio Analogues Scheme. Synthesis of imidazo[1,2-a]pyrimidin-5(1H)-one and benzo[4,5]imidazo[1,2-a]pyrimidin-4(10H)-one derivatives.

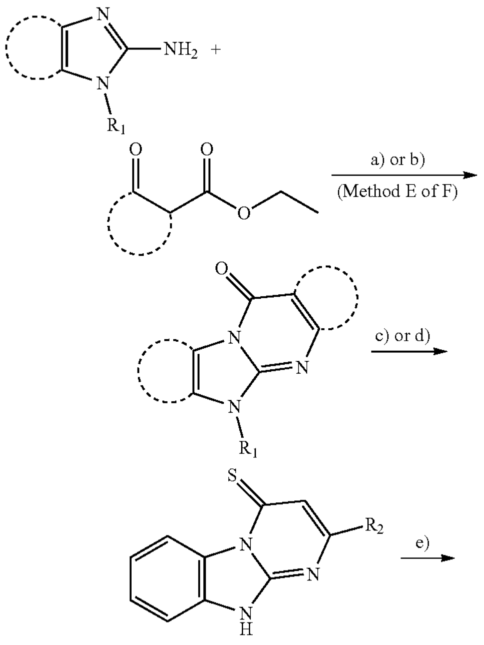

-continued

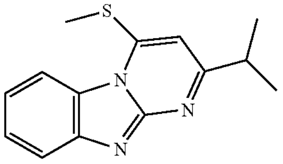

$R_1$ = H, Me, Bn
$R_2$ = Me, i-Pr
Reagents and conditions: a) NaOEt, EtOH, reflux; b) DMF, reflux; c) $P_2S_5$, pyridine, reflux; d) Lawesson's reagent, toluene, reflux; e) $Me_2SO_4$, $NaHCO_3$, acetone, reflux.

Scheme. Synthesis of substituted imidazo[1,2-a]pyrimidin-5(1H)-one and benzo[4,5]imidazo[1,2-a]pyrimidin-4(10H)-one derivatives.

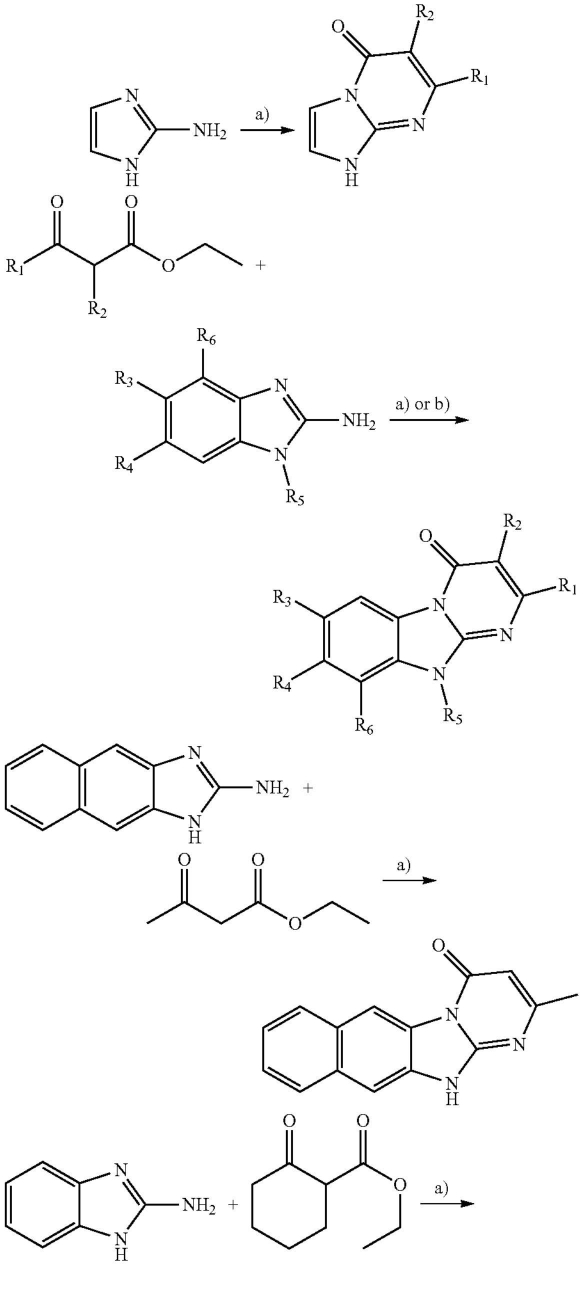

-continued

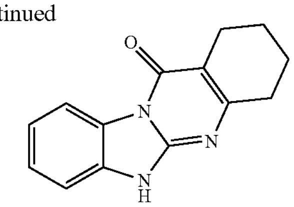

Reagents and conditions: a) NaOEt, EtOH, reflux; b) DMF, reflux;

Scheme. Synthesis of 2-substituted benzo[4,5]imidazo[1,2-a]pyrimidin-4(10H)-thione derivatives and 2-isopropyl-4-(methylthio)benzo[4,5]imidazo[1,2-a]pyrimidine.

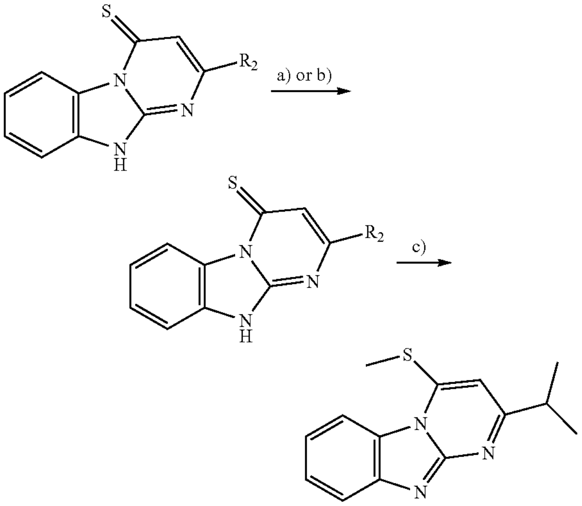

$R_1$ = H, Me
$R_2$ = Me, i-Pr
Reagents and conditions: a) $P_2S_5$, pyridine, reflux; b) Lawesson's reagent, toluene, reflux; c) $Me_2SO_4$, $NaHCO_3$, acetone, reflux.

General Procedures:

Method E:

To a mixture of 2-aminoimidazole derivative (1 mol. equiv.) and 3-oxoester (1.0-1.1 mol. equiv.) in absolute EtOH (3 ml/1 mmol of starting imidazole derivative) was added sodium ethoxide (21% in EtOH; 2 mol. equiv.). Resulting mixture was refluxed for several hours (TLC control). Upon disappearance of starting materials or no further progress of the reaction mixture was cooled to room temperature. Volatiles were removed under reduced and a crude product was purified using flash silica gel column chromatography or preparative TLC. In case of not sufficient purity of product after chromatographic purification, solid was suspended in MeOH, filtered and dried affording target compound.

Method F:

To an appropriate 2-aminoimidazole derivative (1 mol. equiv.) in DMF (1-1.5 ml/1 mmol of starting material) was added 3-oxoester (1-1.64 mol. equiv.) and the mixture was refluxed for several hours (TLC control). Upon disappearance of starting materials or no further progress of the reaction mixture was cooled to room temperature. If precipitation occurred MeOH or EtOH was added, solid was filtered off, washed with solvent indicated and dried under vacuum. In other case volatiles were removed and residue was purified on silica gel column chromatography.

Purity of all products was determined by HPLC analysis and was at least 95%.

7-Methylimidazo[1,2-a]pyrimidin-5(8H)-one

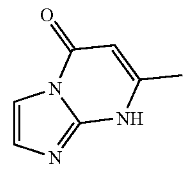

Chemical Formula: $C_7H_7N_3O$
Exact Mass: 149.06

The title compound was synthesized according to Method E starting from 2-aminoimidazole hemisulfate (100 mg, 0.758 mmol) and ethyl acetoacetate (1.1 mol. equiv). Purification by silica gel column chromatography (0-6% gradient of MeOH in $CH_2Cl_2$) afforded 90 mg (0.603 mmol, 80%) as a white solid. $^1H$ NMR (DMSO-$d_6$, 300 MHz): δ (ppm) 2.61 (s, 3H), 5.68 (s, 1H), 7.36 (d, J=2.2 Hz, 1H), 7.52 (d, J=2.2 Hz, 1H), 12.60 (br, 1H). $^{13}C$ NMR (DMSO-$d_6$, 75 MHz): δ (ppm) 22.08, 95.88, 107.00, 121.06, 145.80, 156.91, 159.27. HRMS (ESI): m/z $[M+H]^+$ calcd for $C_7HN_3O$: 150.0662, found: 150.0665.

2-(tert-Butyl)-3-ethylbenzo[4,5]imidazo[1,2-a]pyrimidin-4(10H)-one

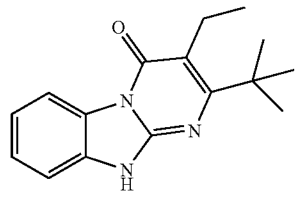

Chemical Formula: $C_{16}H_{19}N_3O$
Exact Mass: 269.15

The title compound was synthesized according to Method F starting from 2-aminobenzimidazole (200 mg, 1.50 mmol) and ethyl 2-ethyl-4,4-dimethyl-3-oxopentanoate (1.1 mol. equiv). Reaction time: 16 h. After removal of volatiles, crude product was purified on silica gel column (30% of EtOAc in heptane) affording 30.2 mg (0.112 mmol; 7%) of product as an off-white solid. $^1H$ NMR (DMSO, 300 MHz): δ 1.15 (t, J=7.2 Hz, 3H), 1.46 (s, 9H), 2.76 (q, J=7.1 Hz, 2H), 7.29 (ddd, J=8.4, 5.6, 3.1 Hz, 1H), 7.44 (m, 2H), 8.45 (d, J=8.0 Hz, 1H), 12.78 (s, 1H). $^{13}C$ NMR (DMSO, 75 MHz): δ 13.91, 19.89, 30.48, 69.91, 110.80, 113.15, 121.40, 125.50, 126.20, 145.85, 160.54 HRMS (ESI): m/z $[M+H]^+$ calcd for $C_6H_{20}N_3O$: 270.16007, found: 270.1595.

2-(4-Methoxyphenyl)benzo[4,5]imidazo[1,2-a]pyrimidin-4(10H)-one

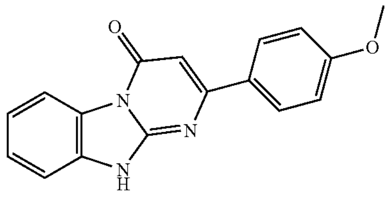

Chemical Formula: $C_{17}H_{13}N_3O_2$
Exact Mass: 291.10

The title compound was synthesized according to Method E starting from 2-aminobenzimidazole (100 mg, 0.751 mmol) and ethyl 3-(4-methoxyphenyl)-3-oxopropanoate (1 mol. equiv). Reaction time: 20 h. Column chromatography of crude product (16-20% AcOEt in $CH_2Cl_2$ as an eluent) afforded 63 mg (0.216 mmol; 29%) of product as an off-white solid. H NMR (DMSO-$d_6$, 300 MHz): δ (ppm) 3.83 (s, 3H), 6.56 (s, 1H), 7.05 (d, J=9.0 Hz, 1H), 7.29-7.38 (m, 1H), 7.48-7.49 (m, 2H), 8.09 (d, J=9.0 Hz, 1H), 8.46 (d, J=8.1 Hz, 1H), 13.01 (br, 1H). $^{13}C$ NMR (DMSO-$d_6$, 75 MHz): δ (ppm) 55.29, 95.73, 110.97, 114.01, 115.59, 121.77, 125.84, 126.04, 128.58, 129.16, 130.64, 149.46, 159.77, 160.32, 161.10. HRMS (ESI): m/z $[M+H]^+$ calcd for $C_7H_4N_3O$: 292.1080, found: 292.1081.

6-Ethyl-7-methylimidazo[1,2-a]pyrimidin-5(8H)-one

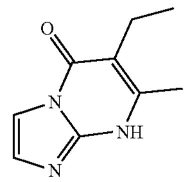

Chemical Formula: $C_9H_{11}N_3O$
Exact Mass: 177.09

The title compound was synthesized according to Method E starting from 2-aminoimidazole hemisulfate (50 mg, 0.379 mmol) and ethyl 2-ethyl-3-oxobutanoate (1 mol. equiv). Purification on preparative TLC (6% of MeOH in $CH_2Cl_2$) afforded 38 mg (0.214 mmol, 56%) as a white solid. $^1H$ NMR (DMSO-$d_6$, 300 MHz): δ (ppm) 1.02 (t, J=7.5 Hz, 3H), 2.32 (s, 3H), 2.48 (q, J=7.5 Hz, 2H; overlapped with residual solvent signal), 7.36 (d, J=2.1 Hz, 1H), 7.48 (d, J=2.1 Hz, 1H), 12.40 (br, 1H). $^{13}C$ NMR (DMSO-$d_6$, 75 MHz): δ (ppm) 13.50, 18.30, 19.56, 106.68, 108.15, 122.10, 143.98, 153.73, 156.92. $^1H$ NMR ($CD_3OD$, 300 MHz): δ (ppm) 1.11 (t, J=7.5 Hz, 3H), 2.41 (s, 3H), 2.61 (q, J=7.5 Hz, 2H), 4.87 (br, 2H), 7.25 (d, J=2.4 Hz, 1H), 7.52 (d, J=2.4 Hz, 1H). $^{13}C$ NMR ($CD_3OD$, 75 MHz): δ (ppm) 13.68, 19.68, 20.21, 108.12, 111.14, 122.10, 145.68, 157.67, 159.52. HRMS (ESI): m/z $[M+H]^+$ calcd for $C_9H_{12}N_3O$: 178.0975, found: 178.0975.

2-Methylbenzo[4,5]imidazo[1,2-a]pyrimidin-4 (10H)-one

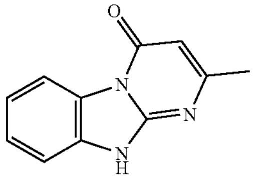

Chemical Formula: $C_{11}H_9N_3O$
Exact Mass: 199.07

The title compound was synthesized according to Method F starting from 2-aminobenzimidazole (100 mg, 0.751 mmol) and ethyl acetoacetate (1 mol. equiv). Reaction time: 1.5 h. Filtration, washing with $H_2O$ and drying afforded product as an off-white solid (98 mg, 0.492 mmol, 66%). $^1H$ NMR (DMSO-$d_6$, 300 MHz): δ (ppm) 2.31 (s, 3H), 5.84 (s, 1H), 7.29 (t, J=7.5 Hz, 1H), 7.43 (t, J=7.5 Hz, 1H), 7.53 (d, 1H, J=7.5 Hz), 8.37 (d, J=7.5 Hz, 1H), 12.73 (br, 1H). $^{13}C$ NMR (DMSO-$d_6$, 75 MHz): δ (ppm) 21.78, 98.53, 113.76, 115.21, 121.41, 125.56, 126.94, 135.42, 148.40, 159.28. HRMS (ESI): m/z $[M+H]^+$ calcd for $C_{11}H_{10}N_3O$: 200.0818, found: 200.0822.

2-Methylbenzo[4,5]imidazo[1,2-a]pyrimidine-4 (10H)-thione

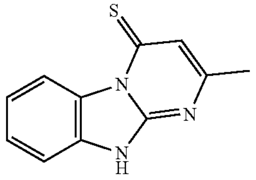

Chemical Formula: $C_{11}H_9N_3S$
Exact Mass: 215.05

Mixture of 2-methylbenzo[4,5]imidazo[1,2-a]pyrimidine-4(10H)-one; 460 mg, 2.309 mmol) and $P_2S_5$ (513 mg, 2.309 mg) in pyridine (2.5 ml) was refluxed for 20 h. Then it was cooled to room temperature, 8 ml of $H_2O$ was added and resulting mixture was extracted with $CH_2Cl_2$ (3×). Organic layers were combined, dried over $MgSO_4$, filtered and solvents were removed in vacuo. Residue was co-evaporated with toluene (3×). Solid residue was purified by flash column chromatography on silica gel (40% of heptane in AcOEt) affording 12 mg (0.056 mmol, 2.5%) of product as a pale brown solid. $^1H$ NMR (DMSO-$d_6$, 300 MHz): δ (ppm) 2.34 (s, 3H), 7.00 (s, 1H), 7.34-7.58 (m, 1H), 7.58-7.59 (m, 2H), 9.73 (d, J=8.4 Hz, 1H), 13.50 (br, 1H). HRMS (ESI): m/z $[M+H]^+$ calcd for $C_1H_{10}N_3S$: 216.0590, found: 216.059.

3-(2-Methoxyethyl)-2-methylbenzo[4,5]imidazo[1,2-a]pyrimidin-4(10H)-one

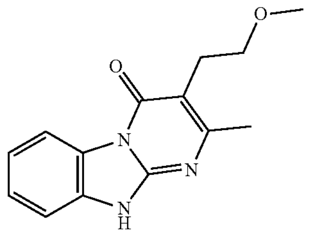

Chemical Formula: $C_{14}H_{15}N_3O_2$
Eact Mass: 257.12

The title compound was synthesized according to Method E starting from 2-aminobenzimidazole (123 mg, 0.924 mmol) and ethyl 2-acetyl-4-methoxybutanoate (1 mol. equiv). Reaction time: overnight. After column chromatography (2-3% gradient of MeOH in $CH_2Cl_2$ as an eluent) fractions containing product were combined and concentrated to dryness. Solid was suspended in EtOH, filtered-off and dried affording 58 mg of off-white solid. Filtrate containing small amount of product was concentrated and the residue was put on preparative TLC (3% of MeOH in $CH_2Cl_2$). Elution of appropriate band afforded additional 14 mg of product. Total yield: 82 mg (0.319 mmol, 35%). $^1H$ NMR (DMSO-$d_6$, 300 MHz): δ (ppm) 2.37 (s, 3H), 2.76 (t, J=7.2 Hz, 2H), 3.26 (s, 3H), 3.44 (t, J=7.2 Hz, 2H), 7.28 (td, J=7.8, 1.2 Hz, 1H), 7.42 (td, J=7.8, 1.2 Hz, 1H), 7.51 (d, J=7.8 Hz, 1H), 8.39 (d, J=7.8 Hz, 1H), 12.60 (br, 1H). $^{13}C$ NMR (DMSO-$d_6$, 75 MHz): δ (ppm) 19.87, 25.33, 57.85, 70.60, 105.77, 113.57, 115.05, 121.05, 125.47, 126.81, 135.51, 146.75, 155.27, 159.46. HRMS (ESI): m/z $[M+H]^+$ calcd for $C_{14}H_{16}N_3O_2$: 258.1237, found: 258.1235.

2-Isopropyl-10-methylbenzo[4,5]imidazo[1,2-a]pyrimidin-4(10H)-one

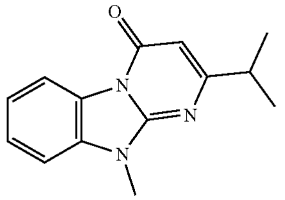

Chemical Formula: $C_{14}H_{15}N_3O$
Eact Mass: 241.12

The title compound was synthesized according to Method F starting from 1-methyl-1H-benzo[d]imidazol-2-amine (50 mg, 0.340 mmol) and ethyl 4-methyl-3-oxopentanoate (2.0 mol. equiv). Reaction time: overnight. DMF was removed under reduced pressure. Crude product was purified by column chromatography on silica gel using (0-4% gradient of MeOH in $CH_2Cl_2$) affording 10 mg (0.041 mmol, 12%) of product as an off-white solid. $^1H$ NMR ($CDCl_3$, 300 MHz): δ (ppm) 1.30 (d, J=6.9 Hz, 6H), 2.86 (sept, J=6.9 Hz, 1H), 3.80 (s, 3H), 7.29-7.36 (m, 2H), 7.46 (td, J=7.8, 0.9 Hz, 1H), 7.63 (d, J=7.8 Hz, 1H). $^{13}C$ NMR ($CDCl_3$, 75 MHz): δ (ppm) 21.82, 28.32, 36.29, 99.02, 108.28, 116.91, 122.53, 125.68, 126.07, 131.71, 149.03, 161.09, 173.73. HRMS (ESI): m/z $[M+H]^+$ calcd for $C_{14}H_{16}N_3O$: 242.1288, found: 242.1290.

3-Ethyl-2-isopropylbenzo[4,5]imidazo[1,2-a]pyrimidin-4(10H)-one

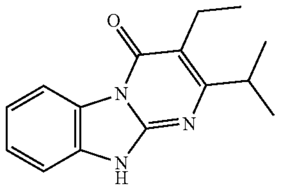

Chemical Formula: $C_{15}H_{17}N_3O$
Eact Mass: 255.14

The title compound was synthesized according to Method E starting from 2-aminobenzimidazole (117 mg, 0.875 mmol) and ethyl 2-ethyl-4-methyl-3-oxopentanoate (1 mol. equiv). Reaction time: 5.5 h. Crude product was purified on column chromatography (2% MeOH in $CH_2Cl_2$). Fractions containing product were combined and concentrated to dryness. The residue was suspended in EtOH, filtered-off and dried affording 39 mg (0.153 mmol; 17%) of product as an off-white solid.

The title compound was also synthesized according to Method F starting from 2-aminobenzimidazole (358 mg, 2.684 mmol) and ethyl 2-ethyl-4-methyl-3-oxopentanoate (1 mol. equiv). Reaction time: 22 h. Filtration of reaction mixture afforded 410 mg (1.688 mmol, 67%) product as an off-white solid.

$^1$H NMR (pyridine-$d_5$, 500 MHz): δ (ppm) 1.20 (t, J=7.5 Hz, 3H), 1.27 (d, J=6.5 Hz, 6H), 2.77 (q, J=7.5 Hz, 2H), 3.13 (sept, J=6.5 Hz, 1H), 7.21 (t, J=7.5 Hz, 1H), 7.34 (t, J=7.5 Hz, 1H), 7.47 (d, J=8.0 Hz, 1H), 8.85 (d, J=8.0 Hz, 1H). $^{13}$C NMR (pyridine-$d_5$, 125 MHz): δ (ppm) 15.17, 18.82, 21.96, 31.52, 111.76, 112.37, 116.67, 121.64, 126.21, 127.56, 148.83, 160.99, 166.61. $^1$H NMR (DMSO-$d_6$, 300 MHz): δ (ppm) 1.08 (t, J=7.2 Hz, 3H), 1.23 (d, J=6.6 Hz, 6H), 2.55 (q, J=7.2 Hz, 2H), 3.24 (sept, J=6.6 Hz, 1H), 7.29-7.31 (m, 1H), 7.42-7.44 (m, 2H), 8.44 (d, J=8.1 Hz, 1H), 12.71 (br, 1H). HRMS (ESI): m/z $[M+H]^+$ calcd for $C_{15}H_{18}N_3O$: 256.1444, found: 256.1442.

3-Ethyl-9-methyl-2-isopropylbenzo[4,5]imidazo[1,2-a]pyrimidin-4(10H)-one

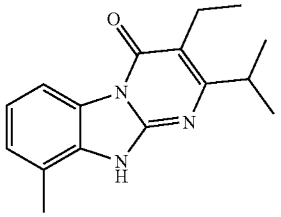

Chemical Formula: $C_{16}H_{19}N_3O$
Eact Mass: 269.15

The title compound was synthesized according to Method F starting from 4-methyl-1H-benzo[d]imidazol-2-amine (150 mg, 1.02 mmol) and ethyl 2-ethyl-4-methyl-3-oxopentanoate (1.0 mol. equiv). Reaction time: 40 h. Volatiles were removed under reduced pressure and the residue was suspended in MeOH. Solid was filtered-off and dried. Filtrate was concentrated to dryness and the procedure was repeated. Combined solids were subjected to silica gel column separation (25% of EtOAc in cyclohexane) affording 89 mg (0.330 mmol, 32%) of product (as a single isomer) as an off-white solid. $^1$H NMR (DMSO-$d_6$, 300 MHz): δ (ppm) 1.08 (t, J=7.5 Hz, 3H), 1.24 (d, J=6.6 Hz, 6H), 2.48 (s, 3H), 2.60 (q, J=7.5 Hz, 2H), 3.19-3.26 (m, 1H), 7.17 (t, J=7.8 Hz, 1H), 7.23 (br d, J=6.9 Hz, 1H), 8.26 (d, J=7.5 Hz, 1H), 12.78 (br, 1H). $^{13}$C NMR (DMSO-$d_6$, 75 MHz): δ (ppm) 14.54, 16.31, 17.74, 21.56, 30.60, 111.26 (br), 112.82, 120.73 (br), 121.18, 125.51, 126.46, 129.56, 147.64, 159.62, 167.05 (br). HRMS (ESI): m/z $[M+H]^+$ calcd for $C_6H_{20}N_3O$: 270.1601, found: 270.1594.

7,8-Dimethyl-3-ethyl-2-isopropylbenzo[4,5]imidazo[1,2-a]pyrimidin-4(10H)-one

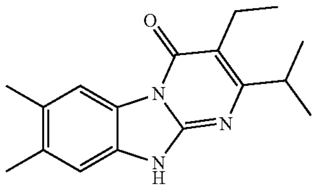

Chemical Formula: $C_{17}H_{21}N_3O$
Eact Mass: 283.17

The title compound was synthesized according to Method F starting from 5,6-dimethyl-1H-benzo[d]imidazol-2-amine hydrobromide (333 mg, 1.375 mmol) and ethyl 2-ethyl-4-methyl-3-oxopentanoate (1.64 mol. equiv). Reaction time: 24 h. MeOH was added and precipitate was filtered-off from reaction mixture, washed with MeOH and dried affording 141 mg (0.497 mmol, 36%) of product as a beige solid. $^1$H NMR (DMSO-$d_6$, 300 MHz): δ (ppm) 1.07 (t, J=7.5 Hz, 3H), 1.21 (d, J=6.6 Hz, 6H), 2.33 (s, 6H), 2.59 (q, J=7.5 Hz, 2H), 3.21 (sept, J=6.6 Hz, 1H), 7.18 (s, 1H), 8.22 (s, 1H), 12.52 (br, 1H). $^1$H NMR (pyridine-d, 300 MHz): δ (ppm) 1.33 (t, J=7.5 Hz, 3H; overlapped with 1.38 (d, J=6.9 Hz, 6H), 2.26 (s, 6H), 2.91 (q, J=7.5 Hz, 2H), 3.25 (sept, J=6.9 Hz, 1H), 7.35 (s, 1H), 8.81 (s, 1H). $^{13}$C NMR (pyridine-$d_5$, 75 MHz): δ (ppm) 15.44, 19.11, 20.29, 20.58, 22.32, 31.82, 112.23, 112.52, 117.49, 126.06, 130.33, 131.08 (br), 135.11, 149.24, 161.12, 166.89. HRMS (ESI): m/z $[M+H]^+$ calcd for $C_7H_{22}N_3O$: 284.1757, found: 284.1753.

7,8-Difluoro-3-ethyl-2-isopropylbenzo[4,5]imidazo[1,2-a]pyrimidin-4(10H)-one

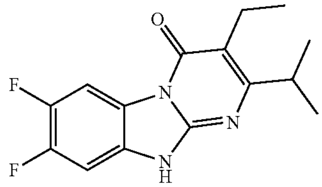

Chemical Formula: $C_{15}H_{15}F_2N_3O$
Eact Mass: 291.12

The title compound was synthesized according to Method F starting from 5,6-difluoro-1H-benzo[d]imidazol-2-amine (150 mg, 0.886 mmol) and ethyl 2-ethyl-4-methyl-3-oxo-pentanoate (1.1 mol. equiv). Reaction time: 22 h. MeOH was added, precipitate was filtered-off, washed with MeOH and dried affording 147 mg (0.505 mmol, 57%) of product as a pale yellow solid. $^{1}H$ NMR (DMSO-$d_6$, 500 MHz): δ (ppm) 1.05 (t, J=7.5 Hz, 3H), 1.25 (br, 6H), 2.56 (q, J=7.5 Hz, 2H), 3.23 (br, 1H), 7.54 (br, 1H), 8.26 (br, 1H), 12.93 and 14.36 (2×br, 1H). $^{19}F$ NMR (DMSO-$d_6$, 470 MHz): δ (ppm) −140.67, −145.54, −145.12, −138.93. HRMS (ESI): m/z $[M+H]^+$ calcd for $C_{15}H_{16}F_2N_3O$: 292.1256, found: 292.1253.

7,8-Dichloro-3-ethyl-2-isopropylbenzo[4,5]imidazo[1,2-a]pyrimidin-4(10H)-one

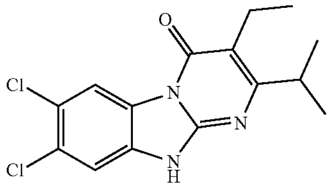

Chemical Formula: $C_{15}H_{15}Cl_2N_3O$
Eact Mass: 323.06

The title compound was synthesized according to Method F starting from 5,6-dichloro-1H-benzo[d]imidazol-2-amine (150 mg, 0.742 mmol) and ethyl 2-ethyl-4-methyl-3-oxo-pentanoate (1.0 mol. equiv). Reaction time: 24 h. Volatiles were removed under reduced pressure and crude product was purified on silica gel column (0-25% gradient of EtOAc in cyclohexane) affording 47 mg (0.145 mmol, 20%) of product as a beige solid. $^{1}H$ NMR (DMSO-$d_6$, 300 MHz): δ (ppm) 1.07 (t, J=7.2 Hz, 3H), 1.27 (d, J=6.6 Hz, 6H), 2.57 (q, J=7.2 Hz, 2H), 3.25 (sept, J=6.6 Hz, 1H), 7.70 (s, 1H), 8.45 (s, 1H), 12.71 (br, 1H). $^{13}C$ NMR (DMSO-$d_6$, 75 MHz): δ (ppm) 14.40, 17.59, 20.78, 29.79, 115.91, 122.57, 126.45, 127.71, 148.24, 159.31. HRMS (ESI): m/z $[M+H]^+$ calcd for $C_{15}H_6Cl_2N_3O$: 324.0665, found: 324.0668, 326.0638. 2-Isopropyl-3-propylbenzo[4,5]imidazo[1,2-a]pyrimidin-4(10H)-one

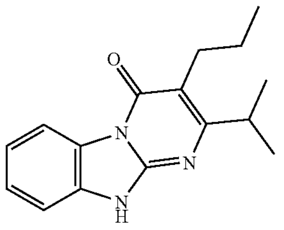

Chemical Formula: $C_{16}H_{19}N_3O$
Eact Mass: 269.15

The title compound was synthesized according to Method E starting from 2-aminobenzimidazole (168 mg, 1.258 mmol) and ethyl 4-methyl-3-oxo-2-propylpentanoate (1 mol. equiv). Reaction time: 20 h. After column chromatography (10-20% AcOEt in $CH_2Cl_2$ as an eluent) fractions containing product were combined and concentrated to dryness. Solid was suspended in MeOH, filtered-off and dried affording 86 mg (0.320 mmol; 25%) of product as an off-white solid. $^{1}H$ NMR (pyridine-$d_5$, 300 MHz): δ (ppm) 1.06 (t, J=7.5 Hz, 3H), 1.36 (d, J=6.6 Hz, 6H), 1.75 (sext, J=7.5 Hz, 2H), 2.81-2.86 (m, 2H), 3.27 (sept, J=6.6 Hz, 1H), 7.29 (td, J=8.1, 0.9 Hz, 1H), 7.42 (td, J=7.8, 0.9 Hz, 1H), 7.55 (d, J=8.1 Hz, 1H), 8.93 (d, J=7.8 Hz, 1H). $^{13}C$ NMR (pyridine-$d_5$, 75 MHz): δ (ppm) 14.70, 22.07, 24.03, 27.65, 31.73, 110.97, 111.88, 116.80, 121.76, 126.32, 127.69, 133.30, 149.00, 161.33, 166.87. HRMS (ESI): m/z $[M+H]^+$ calcd for $C_6H_{20}N_3O$: 270.1601, found: 270.1601.

Ethyl-2-propylbenzo[4,5]imidazo[1,2-a]pyrimidin-4(10H)-one

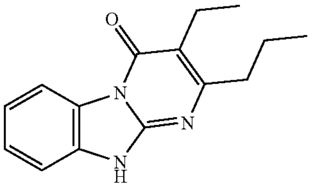

Chemical Formula: $C_{15}H_{17}N_3O$
Eact Mass: 255.14

The title compound was synthesized according to Method E starting from 2-aminobenzimidazole (46 mg, 0.342 mmol) and ethyl 3-oxo-2-ethylhexanoate (1.1 mol. equiv). Reaction time: overnight. Purification on column chromatography using 2-3% gradient of MeOH in $CH_2Cl_2$ as an eluent afforded 38 mg (0.149 mmol, 44%) of product as a white solid.

The title compound was also synthesized according to Method F starting from 2-aminobenzimidazole (358 mg, 2.684 mmol) and ethyl 3-oxo-2-propylhexanoate (1 mol. equiv). Reaction time: 24 h. Filtration of reaction mixture, washing precipitate with EtOH and drying afforded 320 mg (1.253 mmol, 47%) of product as an off-white solid.

$^{1}H$ NMR (DMSO-$d_6$, 600 MHz): δ (ppm) 0.96 (t, J=7.2 Hz, 3H), 1.08 (t, J=7.5 Hz, 3H), 1.69 (sext, J=7.8 Hz, 2H), 2.54 (q, J=7.2 Hz, 2H), 2.59-2.61 (m, 2H), 7.26 (td, J=8.4, 1.2 Hz, 1H), 7.41 (td, J=7.8, 1.2 Hz, 1H), 7.47 (d, J=8.4 Hz, 1H), 8.40 (d, J=7.8 Hz, 1H), 12.55 (br, 1H). $^{13}C$ NMR (DMSO-$d_6$, 150 MHz): δ (ppm) 13.87, 14.24, 18.14, 21.90, 34.58, 111.14 (br), 113.32, 115.20, 121.07, 125.63, 126.81, 147.01, 159.69. HRMS (ESI): m/z $[M+H]^+$ calcd for $C_{15}H_{18}N_3O$: 256.1444, found: 256.1445.

7,8-Dimethyl-3-ethyl-2-propylbenzo[4,5]imidazo[1,2-a]pyrimidin-4(10H)-one

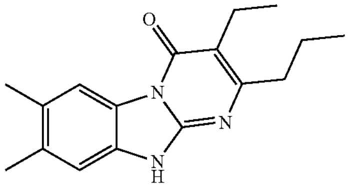

Chemical Formula: $C_{17}H_{21}N_3O$
Eact Mass: 283.17

The title compound was synthesized according to Method F starting from 5,6-dimethyl-1H-benzo[d]imidazol-2-amine hydrobromide (305 mg, 1.260 mmol) and ethyl 2-ethyl-3-oxohexanoate (1.5 mol. equiv). Reaction time: 24 h. Water was added and precipitate was filtered-off and dried.

Purification on silica gel column (2-3% gradient of MeOH in $CH_2Cl_2$) afforded 65 mg of pure product as a yellow-orange solid. Second fraction containing contaminated product was concentrated to dryness and put on preparative TLC (2% of MeOH in $CH_2Cl_2$ with 1% vol. of 7 N ammonia in MeOH) affording additional 60 mg of product. Total yield: 125 mg (0.441 mmol, 23%). $^1$H NMR (DMSO-$d_6$, 300 MHz): δ (ppm) 0.97 (t, J=7.5 Hz, 3H), 1.08 (t, J=7.5 Hz, 3H), 1.69 (sext, J=7.5 Hz, 2H), 2.33 (s, 6H), 2.51-2.61 (m, 4H; overlapped with residual solvent signal), 7.24 (s, 1H), 8.20 (s, 1H), 12.44 (br, 1H). $^1$H NMR (pyridine-$d_5$, 300 MHz): δ (ppm) 0.99 (t, J=7.2 Hz, 3H), 1.33 (t, J=7.2 Hz, 3H), 1.85 (sext, J=7.5 Hz, 2H), 2.27 and 2.28 (2×s, 6H), 2.71 (t, J=7.5 Hz, 2H), 2.84 (q, J=7.2 Hz, 2H), 7.44 (s, 1H), 8.79 (s, 1H). $^{13}$C NMR (pyridine-$d_5$, 75 MHz): δ (ppm) 14.55, 14.99, 19.46, 20.35, 20.63, 22.95, 36.18, 112.66, 113.83, 117.21, 126.65, 130.24, 133.88, 134.89, 148.54, 159.59, 161.01. HRMS (ESI): m/z [M+H]$^+$ calcd for $C_7H_{22}N_3O$: 284.1757, found: 284.1758.

2,3-Dipropylbenzo[4,5]imidazo[1,2-a]pyrimidin-4(10H)-one

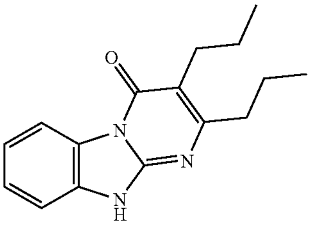

Chemical Formula: $C_{16}H_{19}N_3O$
Eact Mass: 269.15

The title compound was synthesized according to Method E starting from 2-aminobenzimidazole (66 mg, 0.494 mmol) and ethyl 3-oxo-2-propylhexanoate (1 mol. equiv). Reaction time: overnight. Purification by column chromatography using 2-3% gradient of MeOH in $CH_2Cl_2$ as an eluent afforded 40 mg (0.148 mmol, 30%) of product as an off-white solid. H NMR (DMSO-$d_6$, 300 MHz): δ (ppm) 0.93-1.00 (m, 6H), 1.50 (sext, J=7.5 Hz, 2H), 1.70 (sext, J=7.5 Hz, 2H), 2.48-2.52 (m, 2H; overlapped with residual solvent signal), 2.59-2.64 (m, 2H), 7.24-7.30 (m, 1H), 7.39-7.45 (m, 1H), 7.48 (d, J=7.8 Hz, 1H), 8.40 (d, J=8.1 Hz, 1H), 12.48 (br, 1H). $^{13}$C NMR (DMSO-$d_6$, 75 MHz): δ (ppm) 13.76, 13.96, 21.74, 22.43, 26.71, 34.53, 109.53, 113.09, 115.11, 120.97, 125.52, 126.70, 134.99, 146.90, 157.90, 159.75. HRMS (ESI): m/z [M+H]$^+$ calcd for $C_6H_{20}N_3O$: 270.1601, found: 270.1599.

3-Ethyl-2-(4-methoxyphenyl)benzo[4,5]imidazo[1,2-a]pyrimidin-4(10H)-one

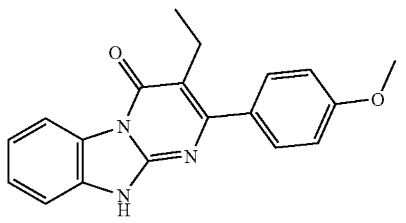

Chemical Formula: $C_{19}H_{17}N_3O_2$
Eact Mass: 319.13

The title compound was synthesized according to Method E starting from 2-aminobenzimidazole (140 mg, 1.051 mmol) and ethyl 2-(4-methoxybenzoyl)butanoate (1 mol. equiv). Reaction time: overnight. After column chromatography (2-3% gradient of MeOH in $CH_2Cl_2$ as an eluent) fractions containing product were combined and concentrated to dryness. Solid was suspended in MeOH, filtered-off and dried affording 50 mg (0.156 mmol; 15%) of product as an off-white solid. $^1$H NMR (pyridine-$d_5$, 300 MHz): δ (ppm) 1.37 (t, J=7.2 Hz, 3H), 2.80 (q, J=7.2 Hz, 2H), 3.76 (s, 3H), 7.14 (d, J=8.7 Hz, 2H), 7.36 (t, J=7.8 Hz, 1H), 7.49 (t, J=7.8 Hz, 1H), 7.68-7.74 (m, 3H), 8.97 (d, J=7.8 Hz, 1H). $^{13}$C NMR (pyridine-$d_5$, 75 MHz): δ (ppm) 14.86, 20.70, 55.67, 113.00, 113.74, 114.48, 116.67, 121.85, 122.35, 126.33, 128.22, 130.77, 131.12, 131.23, 148.28, 156.53, 160.88, 161.34. HRMS (ESI): m/z [M+H]$^+$ calcd for $C_{19}H_{18}N_3O$: 320.1393, found: 320.1388.

Mixture of 2-isopropyl-7-methylbenzo[4,5]imidazo[1,2-a]pyrimidin-4(10H)-one and 2-isopropyl-8-methylbenzo[4,5]imidazo[1,2-a]pyrimidin-4(10H)-one

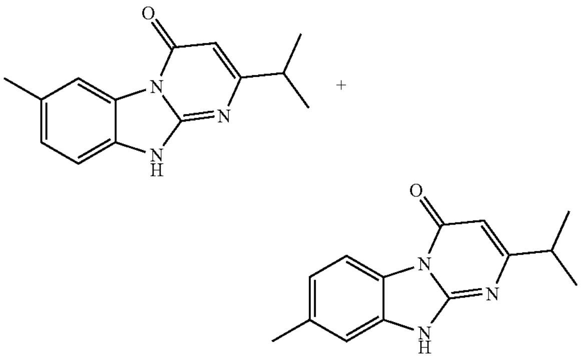

ca. 1.1:1
Chemical Formula: $C_{14}H_{15}N_3O$
Eact Mass: 241.12

The title mixture of compounds was obtained according to Method E starting from 2-amino-5-methyl-1H-benzo[d]imidazole (212 mg, 1.440 mmol) and ethyl 4-methyl-3-oxopentanoate (1.0 mol. equiv). Reaction time: overnight. Column chromatography (0-35% gradient of AcOEt in $CH_2Cl_2$ as an eluent) afforded 191 mg (0.792 mmol; 55%) of product as a mixture of 2 isomers (ca. 1.1:1; an off-white solid). Two isomers were not separable on chromatographic conditions tested. $^{1}$H NMR (DMSO-$d_6$, 300 MHz): δ (ppm) 1.23 (d, J=6.6 Hz, 6H), 2.44 (s, 3H), 2.81 (sept, J=6.6 Hz, 1H), 5.85 and 5.86 (2×s, 1H), 7.10 (d, J=8.1 Hz, 0.56H), 7.24-7.26 (m, 1H), 7.34 (d, J=8.4 Hz, 0.44H), 8.23-8.26 (m, 1H), 12.78 (br, 1H). $^{13}$C NMR (DMSO-$d_6$, 75 MHz): δ (ppm) 21.10, 21.27, 21.38, 21.41, 34.47, 34.58, 96.31, 96.64, 111.99 (br), 114.95, 115.39, 122.49, 124.09, 126.39, 126.65, 130.79, 135.46, 148.98, 149.09, 159.49, 159.67. HRMS (ESI): m/z [M+H]$^+$ calcd for $C_{14}H_{16}N_3O$: 242.1288, found: 242.1284.

Mixture of 3-ethyl-7-fluoro-2-isopropylbenzo[4,5]imidazo[1,2-a]pyrimidin-4(10H)-one and 3-ethyl-8-fluoro-2-isopropylbenzo[4,5]imidazo[1,2-a]pyrimidin-4(10H)-one

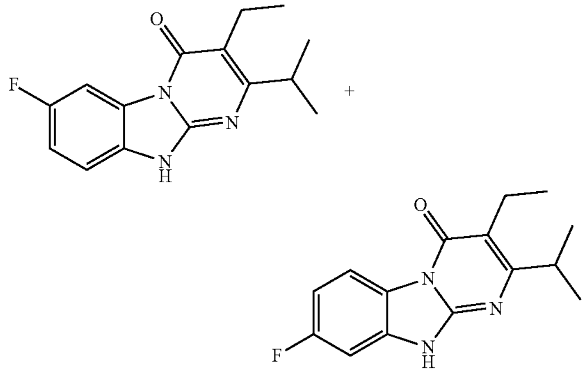

1:2
Chemical Formula: $C_{15}H_{16}FN_3O$
Eact Mass: 273.13

The title mixture of compounds was obtained according to Method F starting from 2-amino-5-fluoro-1H-benzo[d]imidazole (150 mg, 0.992 mmol) and ethyl 2-ethyl-4-methyl-3-oxopentanoate (1.0 mol. equiv). Reaction time: 24 h. MeOH was added and precipitate was filtered-off, washed with MeOH and dried affording 135 mg (0.494 mmol, 50%) of mixture of 2 isomers (in a ratio ca. 1:2) as a pale brown flakes. $^{1}$H NMR (pyridine-$d_5$, 500 MHz): δ (ppm) 1.29 and 1.30 (2×t, J=7.5 Hz and J=7.5 Hz, 3H), 1.37 (d, J=6.5 Hz, 6H), 2.82-2.88 (m, 2H), 3.25 (sept, J=6.5 Hz, 1H), 7.12-8.84 [3H; 7.12 (td, J=9.5 Hz, J=2.5 Hz), 7.28 (td, J=9.5 Hz, J=2.5 Hz), 7.41 (dd, J=9.0 Hz, J=2.0 Hz), 7.49 (dd, J=8.5 Hz, J=4.5 Hz), 8.84 (dd, J=9.0 Hz, J=5.0 Hz)]. 1F NMR (pyridine-$d_5$, 470 MHz): δ (ppm) −120.58, -115.31. HRMS (ESI): m/z [M+H]$^+$ calcd for $C_{15}H_{17}FN_3O$: 274.1350, found: 274.1351.

Mixture of 7-chloro-3-ethyl-2-isopropylbenzo[4,5]imidazo[1,2-a]pyrimidin-4(10H)-one and 8-chloro-3-ethyl-2-isopropylbenzo[4,5]imidazo[1,2-a]pyrimidin-4(10H)-one

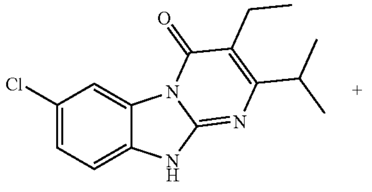

-continued

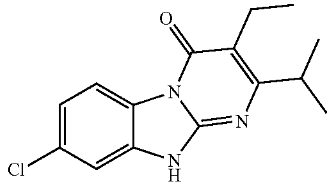

1:1
Chemical Formula: $C_{15}H_{16}ClN_3O$
Eact Mass: 289.10

The title mixture of compounds was obtained according to Method F starting from 2-amino-5-chloro-1H-benzo[d]imidazole (140 mg, 0.835 mmol) and ethyl 2-ethyl-4-methyl-3-oxopentanoate (1.0 mol. equiv). Reaction time: 24 h. EtOH was added and precipitate was filtered-off, washed with EtOH and dried affording 86 mg (0.297 mmol, 36%) of mixture of 2 isomers (in a ratio ca. 1:1) as a beige solid. $^{1}$H NMR (DMSO-$d_6$, 300 MHz): δ (ppm) 1.07 (t, J=7.2 Hz, 3H), 1.25 (d, J=6.6 Hz, 6H), 2.59 (q, J=7.2 Hz, 2H), 3.23 (sept, J=6.6 Hz, 1H; overlapped with $H_2O$ signal), 7.29-8.39 [3H; 7.29 (dd, J=8.7 Hz, J=1.8 Hz), 7.45-7.48 (m), 8.35-8.39 (m)]. $^{1}$H NMR (pyridine-$d_5$, 300 MHz): δ (ppm) 1.29 (m, 3H), 1.37 (d, J=6.6 Hz, 6H), 2.83 (q, J=7.5 Hz, 2H), 3.23 (sept, J=6.6 Hz, 1H), 7.35-8.98 [3H; 7.35 (dd, J=8.4 Hz, J=1.8 Hz); 7.46-7.53 (m); 7.68 (d, J=1.8 Hz); 8.81 (d, J=8.4 Hz); 8.98 (d, J=1.2 Hz)]. HRMS (ESI): m/z [M+H]$^+$ calcd for $C_5H_7ClN_3O$: 290.1054, found: 290.1061, 292.1031.

Mixture of 3-ethyl-2-isopropyl-7-methylbenzo[4,5]imidazo[1,2-a]pyrimidin-4(10H)-one and 3-ethyl-2-isopropyl-8-methylbenzo[4,5]imidazo[1,2-a]pyrimidin-4(10H)-one

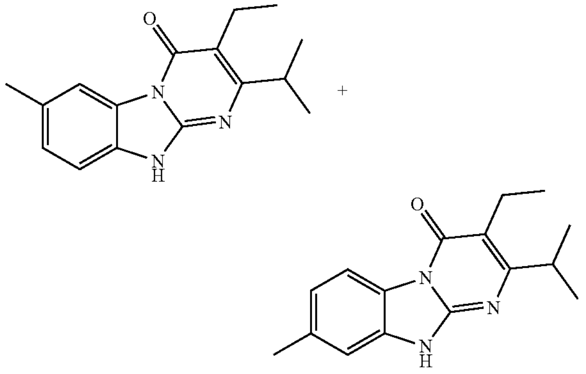

1:1.5
Chemical Formula: $C_{16}H_{19}N_3O$
Eact Mass: 269.15

The title mixture of compounds was obtained according to Method F starting from 2-amino-5-methyl-1H-benzo[d]imidazole (395 mg, 2.684 mmol) and ethyl 2-ethyl-4-methyl-3-oxopentanoate (1.0 mol. equiv). Reaction time: 22 h. Product was filtered-off from reaction mixture, washed with EtOH and dried affording 402 mg (1.492 mmol, 56%) mixture of 2 isomers (in a ratio ca. 1:1.5) as pale brown solid. Two isomers were not separable under chromatographic conditions tested. $^{1}$H NMR (DMSO-$d_6$, 600 MHz): δ (ppm) 1.06 (t, J=7.2 Hz, 3H), 1.21 (d, J=6.0 Hz, 6H), 2.43 and 2.44 (2×s, 3H), 2.58 (q, J=7.5 Hz, 2H), 3.18 (m, 1H), 7.08 (d, J=8.4 Hz, 0.6H), 7.20-7.29 (m, 1.4H), 8.27-8.29 (m, 1H), 12.63 (br, 1H). $^{13}C$ NMR (DMSO-$d_6$, 150 MHz): δ (ppm) 14.64, 17.82, 21.23, 21.38, 21.71, 30.74, 110.17 (br), 110.60 (br), 111.51 (br), 115.18, 115.70, 122.27, 123.73, 125.98, 126.80, 128.21, 128.49 (br), 130.56, 135.74, 147.70, 159.55, 159.71, 167.11 (br). HRMS (ESI): m/z $[M+H]^+$ calcd for $C_6H_{20}N_3O$: 270.1601, found: 270.1599.

Mixture of 3-ethyl-2-isopropyl-7-methoxybenzo[4,5]imidazo[1,2-a]pyrimidin-4(10H)-one and 3-ethyl-2-isopropyl-8-methoxybenzo[4,5]imidazo[1,2-a]pyrimidin-4(10H)-one

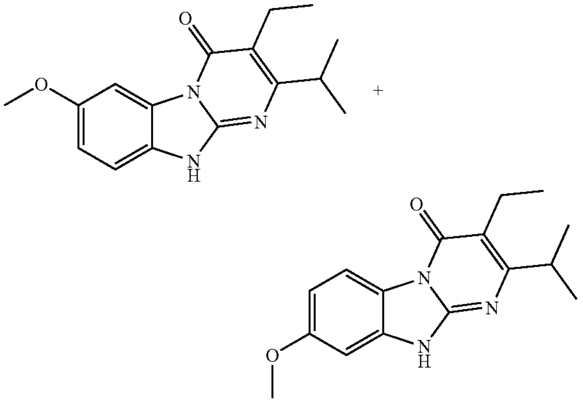

1:1.5
Chemical Formula: $C_{16}H_{19}N_3O_2$
Eact Mass: 285.15

The title mixture of compounds was obtained according to Method F starting from 2-amino-5-methoxy-1H-benzo[d]imidazole (150 mg, 0.919 mmol) and ethyl 2-ethyl-4-methyl-3-oxopentanoate (1.1 mol. equiv). Reaction time: 24 h. MeOH was added and precipitate was filtered-off, washed with MeOH and dried affording 138 mg (0.484 mmol, 53%) of product as a mixture of 2 isomers (in a ratio ca. 1:1.5) as a brown solid. $^1H$ NMR (pyridine-$d_5$, 300 MHz): δ (ppm) 1.32 (t, J=7.5 Hz, 3H), 1.36 and 1.38 (2×d, J=6.6 Hz, 6H), 2.85-2.93 (m, 2H), 3.24 (br sept, J=6.6 Hz, 1H), 6.99-8.87 [3H; 6.99 (dd, J=8.7 Hz, J=2.4 Hz), 7.18-7.22 (m), 7.47 (d, J=9.0 Hz), 8.66 (d, J=2.7 Hz), 8.87 (d, J=8.7 Hz)]. HRMS (ESI): m/z $[M+H]^+$ calcd for $C_6H_{20}N_3O_2$: 286.1550, found: 286.1549.

Mixture of 2-isopropyl-4-oxo-4,10-dihydrobenzo[4,5]imidazo[1,2-a]pyrimidine-7-carbonitrile and 2-isopropyl-4-oxo-4,10-dihydrobenzo[4,5]imidazo[1,2-a]pyrimidine-8-carbonitrile

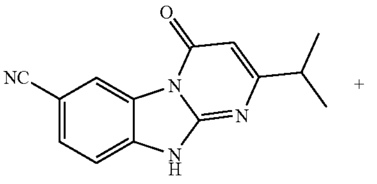

-continued

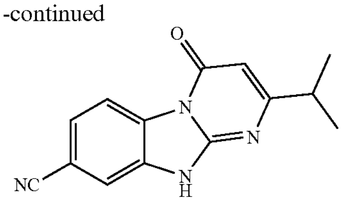

ca. 1.1:1
Chemical Formula: $C_{14}H_{12}N_4O$
Eact Mass: 252.10

The title mixture of compounds was obtained according to Method E starting from 2-amino-1H-benzo[d]imidazole-5-carbonitrile (100 mg, 0.632 mmol) and ethyl 4-methyl-3-oxopentanoate (1.0 mol. equiv). Reaction time: 8 h. Column chromatography of crude product (50% of AcOEt in cyclohexane as an eluent) afforded 34 mg (0.135 mmol; 21%) of product as a mixture of 2 isomers (in a ratio 1.1:1) as an off-white solid. Two isomers were not separable under chromatographic conditions tested. $^1H$ NMR (DMSO-$d_6$, 600 MHz): δ (ppm) 1.24-1.25 (2×d, J=7.2 Hz and J=6.6 Hz, 6H), 2.87 (sept, J=6.9 Hz, 1H), 5.84 and 5.89 (2×s, 1H), 7.65-7.66 (dd, J=8.4, 1.2 Hz and d, J=8.4 Hz; 1H), 7.80 (dd, J=8.4, 1.2 Hz, 0.45H), 8.01 (s, 0.4H), 8.41 (d, J=7.8 Hz, 0.4H), 8.58 (d, J=1.2 Hz, 0.45H). $^{13}C$ NMR (DMSO-$d_6$, 150 MHz): δ (ppm) 21.29, 21.34, 95.49, 96.31, 102.88, 107.65, 116.03, 118.83, 119.59, 119.76, 125.29, 127.37, 129.68, 130.83, 149.55, 150.05, 159.72, 159.88. HRMS (ESI): m/z $[M+H]^+$ calcd for $C_{14}H_{13}N_4O$: 253.1084, found: 253.1084.

Mixture of 3-ethyl-7-methyl-2-propylbenzo[4,5]imidazo[1,2-a]pyrimidin-4(10H)-one and 3-ethyl-8-methyl-2-propylbenzo[4,5]imidazo[1,2-a]pyrimidin-4(10H)-one

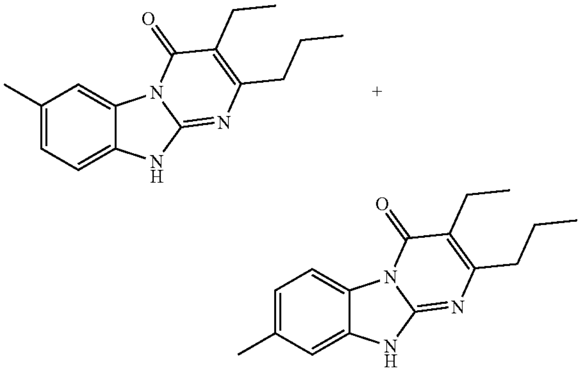

1:1.6
Chemical Formula: $C_{16}H_{19}N_3O$
Eact Mass: 269.15

The title mixture of compounds was obtained according to Method F starting from 2-amino-5-methyl-1H-benzo[d]imidazole (189 mg, 1.284 mmol) and ethyl 2-ethyl-3-oxohexanoate (1.2 mol. equiv). Reaction time: 20 h. Product was filtered-off from reaction mixture, washed with EtOH and dried affording 149 mg (0.553 mmol, 43%) of product (mixture of 2 isomers in a ratio 1:1.6) as grey solid. Two isomers were not separable on chromatographic column. $^1H$ NMR (DMSO-$d_6$, 600 MHz): δ (ppm) 0.96 (t, J=7.2 Hz, 3H), 1.07 (t, J=7.2 Hz, 3H), 1.69 (sext, J=7.2 Hz, 2H), 2.43 and 2.44 (2×s, 3H), 2.53 (q, J=7.2 Hz, 2H), 2.55-2.60 (m, 2H), 7.07 (d, J=8.4 Hz, 0.6H), 7.23 (d, J=7.8 Hz, 0.36H), 7.26 (s, 0.6H), 7.34 (d, J=7.8 Hz, 0.36H), 8.24-8.26 (m, 1H), 12.47 (br, 1H). $^{13}$C NMR (DMSO-$d_6$, 150 MHz): δ (ppm) 13.93, 14.26, 18.18, 21.28, 21.44, 21.87, 21.90, 34.88, (br), 111.05 (br), 111.41 (br), 114.90, 115.39, 122.18, 124.56, 126.62, 126.87, 130.38, 135.34, 147.01, 147.11, 159.53, 159.71.

HRMS (ESI): m/z $[M+H]^+$ calcd for $C_6H_{20}N_3O$: 270.1601, found: 270.1602.

Mixture of 7-cyano-3-ethyl-2-isopropylbenzo[4,5]imidazo[1,2-a]pyrimidin-4(10H)-one and 8-cyano-3-ethyl-2-isopropylbenzo[4,5]imidazo[1,2-a]pyrimidin-4(10H)-one

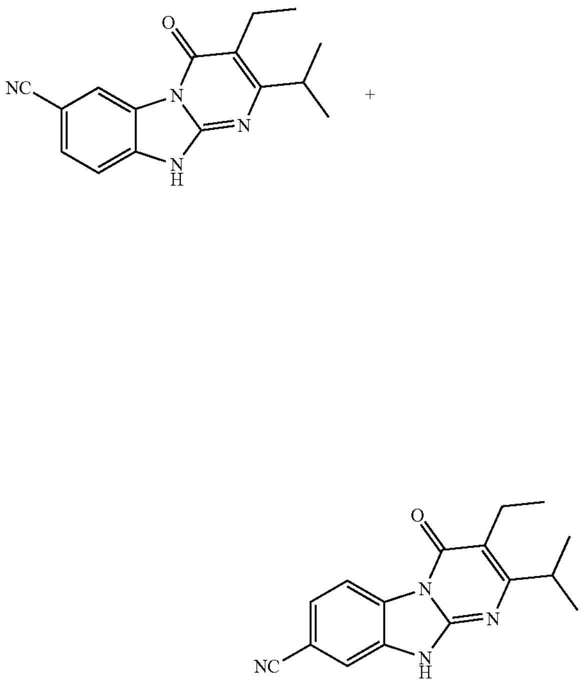

1.5:1

Chemical Formula: $C_{16}H_{16}N_4O$

Eact Mass: 280.13

The title mixture of compounds was obtained according to Method F starting from 2-amino-5-cyano-1H-benzo[d]imidazole (150 mg, 0.948 mmol) and ethyl 2-ethyl-4-methyl-3-oxopentanoate (1.0 mol. equiv). Reaction time: 24 h. Volatiles were removed under reduced pressure. Solid residue was suspended in EtOH, solid was filtered-off, washed with EtOH and dried affording 61 mg (0.218 mmol, 23%) of product (mixture of 2 isomers in a ratio ca. 1.5:1) as a pale yellow solid. $^1$H NMR (pyridine-$d_5$, 300 MHz): δ (ppm) 1.28 (t, J=7.5 Hz, 3H), 1.38 and 1.39 (2×d, J=6.9 Hz, 6H), 2.81 (br q, J=7.2 Hz, 2H), 3.26 (sept, J=6.9 Hz, 1H), 7.63-9.20 [3H; 7.63 (d, J=9.0 Hz), 7.76 (dd, J=8.1 Hz, J=1.5 Hz), 8.01 (d, J=1.5 Hz), 8.85 (d, J=8.1 Hz), 9.20 (d, J=1.5 Hz)]. HRMS (ESI): m/z $[M+H]^+$ calcd for $C_{1\text{-}6}H_7N_4O$: 281.1397, found: 281.1390.

2-Isopropylbenzo[4,5]imidazo[1,2-a]pyrimidine-4(10H)-thione

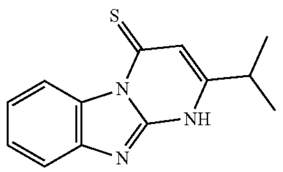

Chemical Formula: $C_{13}H_{13}N_3S$

Eact Mass: 243.08

Mixture of 2-isopropylbenzo[4,5]imidazo[1,2-a]pyrimidine-4(10H)-one; 300 mg, 1.320 mmol) and Lawesson's reagent (1.068 g, 2.640 mmol) in toluene (15 ml) was refluxed overnight. The mixture was cooled to room temperature, precipitate was filtered-off, washed with toluene and dried. Purification using flash column chromatography on silica gel (0-3% gradient of MeOH in $CH_2Cl_2$) afforded 226 mg of pale yellow solid. Additional amount of product (30 mg) was obtained from purification (column chromatography) of filtrate from the reaction mixture. Total yield: 256 mg (1.052 mmol, 80%). $^1$H NMR (DMSO-$d_6$, 600 MHz): δ (ppm) 1.25 (d, J=7.2 Hz, 6H), 2.88 (sept, J=7.2 Hz, 1H), 6.99 (s, 1H), 7.35 (ddd, J=8.4, 7.2, 1.8 Hz, 1H), 7.54-7.59 (m, 2H), 9.72 (d, J=8.4 Hz, 1H). $^{13}$C NMR (DMSO-$d_6$, 150 MHz): δ (ppm) 21.59, 34.73, 111.40, 115.78, 118.29, 121.02, 127.48, 128.10, 131.46, 148.39, 166.87, 177.86. HRMS (ESI): m/z $[M+H]^+$ calcd for $C_{13}H_{14}N_3S$: 244.0903, found: 244.0889.

2-Isopropyl-4-(methylthio)benzo[4,5]imidazo[1,2-a]pyrimidine

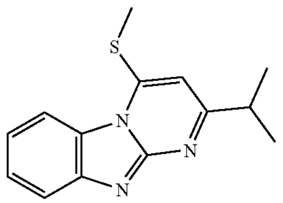

Chemical Formula: $C_{14}H_{15}N_3S$

Eact Mass: 257.10

To a mixture of 2-isopropylbenzo[4,5]imidazo[1,2-a]pyrimidine-4(10H)-thione (100 mg, 0.411 mmol) and $NaHCO_3$ (43 mg (0.512 mmol) in acetone (2 ml) was added $Me_2SO_4$ (78 μl, 0.822 mmol) and resulting mixture was refluxed for 20 h. Volatiles were removed in vacuo and crude product was purified first on silica gel column chromatography (0-10% gradient of MeOH in $CH_2Cl_2$) and second on preparative TLC (4% of MeOH in $CH_2Cl_2$) affording 17 mg (0.066 mmol, 16%) of product.

$^1$H NMR ($CDCl_3$, 300 MHz): δ (ppm) 1.39 (d, J=6.9 Hz, 6H), 2.74 (s, 3H), 3.11 (sept, J=6.9 Hz, 1H), 6.46 (s, 1H), 7.33 (t, J=7.5 Hz, 1H), 7.52 (t, J=7.5 Hz, 1H), 7.95 (d, J=8.1 Hz, 1H), 8.35 (d, J=8.4 Hz, 1H). $^{13}$C NMR ($CDCl_3$, 75 MHz): δ (ppm) 14.93, 21.77, 37.25, 100.53, 115.50, 119.88, 121.00, 125.77, 128.57, 144.82, 151.72, 152.88, 171.54. HRMS (ESI): m/z $[M+H]^+$ calcd for $C_{14}H_{16}N_3S$: 258.1059, found: 258.1064.

1,3,4,6-Tetrahydrobenzo[4,5]imidazo[2,1-b]quinazolin-12(2H)-one

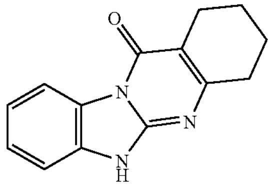

Chemical Formula: $C_{14}H_{13}N_3O$
Eact Mass: 239.11

The title compound was synthesized according to Method E starting from 2-aminobenzimidazole (100 mg, 0.751 mmol) and ethyl 2-oxocyclohexane-1-carboxylate (1 mol. equiv). Reaction time: 5 h. Volatiles were removed under reduced pressure. Column chromatography (2% MeOH in $CH_2Cl_2$ as an eluent) of crude reaction mixture afforded 151 mg (0.631 mmol; 84%) of product as an white solid. $^1H$ NMR (DMSO-$d_6$, 300 MHz): δ (ppm) 1.71-1.79 (m, 4H), 2.45-2.48 (m, 2H), 2.61-2.65 (m, 2H), 7.26 (td, J=8.1, 1.2 Hz, 1H), 7.40 (td, J=8.1, 0.9 Hz, 1H), 7.49 (d, J=7.8 Hz, 1H), 7.38 (d, J=7.8 Hz, 1H), 12.49 (br, 1H). $^{13}C$ NMR (DMSO-$d_6$, 75 MHz): δ (ppm) 21.41, 21.64, 21.71, 29.44, 106.25, 113.47, 114.95, 120.88, 125.34, 126.85, 135.65, 146.84, 154.80, 159.46. HRMS (ESI): m/z $[M+H]^+$ calcd for $C_{14}H_{14}N_3O$: 240.1132, found: 240.1132.

2-Methylnaphtho[2',3':4,5]imidazo[1,2-a]pyrimidin-4(12H)-one

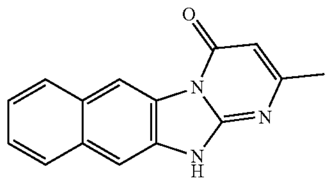

Chemical Formula: $C_{15}H_{11}N_3O$
Eact Mass: 249.09

The title compound was synthesized according to Method E starting from 2-amino-1H-naphtho[2,3-d]imidazole (100 mg, 0.546 mmol) and ethyl acetoacetate (1 mol. equiv). Reaction time: 6 h. Volatiles were removed under reduced pressure. After column chromatography (50-55% gradient of AcOEt in $CH_2Cl_2$ and next 2% of MeOH in $CH_2Cl_2$) fractions containing product were combined and concentrated to dryness. Solid was suspended in MeOH, filtered-off and dried affording 47 mg (0.188 mmol; 34%) of product as a pale brown solid. $^1H$ NMR (pyridine-$d_5$): δ (ppm) 2.40 (s, 3H), 6.18 (s, 1H), 7.52-7.65 (m, 2H), 8.06-8.15 (m, 3H), 9.44 (s, 1H). HRMS (ESI): m/z $[M+H]^+$ calcd for $C_5H_{12}N_3O$: 250.0975, found: 250.0974.

2-Isopropylnaphtho[2',3':4,5]imidazo[1,2-a]pyrimidin-4(12H)-one

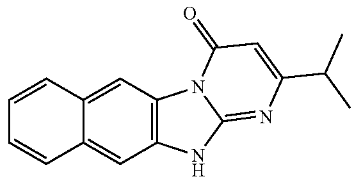

Chemical Formula: $C_{17}H_{15}N_3O$
Eact Mass: 277.12

The title compound was synthesized according to Method E starting from 2-amino-1H-naphtho[2,3-d]imidazole (100 mg, 0.546 mmol) and ethyl acetoacetate (1.3 mol. equiv). Reaction time: 22 h. Column chromatography of crude product (2% of MeOH in $CH_2Cl_2$) afforded 85 mg (0.306 mmol; 56%) of product as an off-white solid. $^1H$ NMR (DMSO-$d_6$, 300 MHz): δ (ppm) 1.27 (d, J=6.9 Hz, 6H), 2.84 (sept, J=6.9 Hz, 1H), 5.95 (s, 1H), 7.44-7.54 (m, 2H), 7.87 (s, 1H), 8.04 (d, J=8.1 Hz, 1H), 8.12 (d, J=7.8 Hz, 1H), 8.91 (s, 1H). $^{13}C$ NMR (DMSO-$d_6$, 75 MHz): δ (ppm) 21.32, 34.76, 97.81, 107.02, 112.66, 124.12, 125.55, 126.80, 127.11, 128.35, 128.67, 131.38, 150.93, 159.82, 171.58. HRMS (ESI): m/z $[M+H]^+$ calcd for $C_7H_6N_3O$: 278.1288, found: 278.1293.

7,8-Dibromo-3-ethyl-2-isopropylbenzo[4,5]imidazo[1,2-a]pyrimidin-4(10H)-one

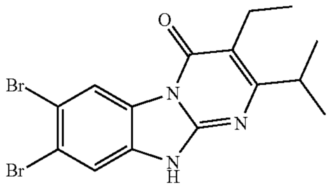

Chemical Formula: $C_{15}H_{15}Br_2N_3O$
Eact Mass: 410.96

To a solution of 5,6-dibromo-H-benzo[d]imidazol-2-amine (100 mg, 0.343 mmol) in pyridine was added ethyl 2-ethyl-4-methyl-3-oxopentanoate (1 mol. Equiv.). The reaction mixture was refluxed for 48 hours. The solvent was evaporated and the crude was purified using column chromatography (heptane:EtOAc—5:1) yielding 31.2 mg of the product as a beige solid (0.075 mmol, 22%). $^1H$ NMR ($CDCl_3$, 300 MHz): δ (ppm) 1.19 (t, J=7.4 Hz, 3H), 1.35 (d, J=6.9 Hz, 6H), 2.68 (q, J=7.4 Hz, 2H) 3.34 (m, 1H), 7.85 (s, 1H), 8.84 (s, 1H). $^{13}C$ NMR (pyridine-$d_5$, 75 MHz): δ (ppm) 14.73, 18.37, 21.18, 29.78, 54.90, 61.47, 111.23. 115.14, 118.21, 119.99, 120.59, 137.11, 160.10, 162.36. HRMS (ESI): m/z $[M+H]^+$ calcd for $C_5H_6N_3OBr_2$: 411.96556, found: 411.9651.

2-(tert-Butyl)-3-ethylbenzo[4,5]imidazo[1,2-a]pyrimidin-4(10H)-one

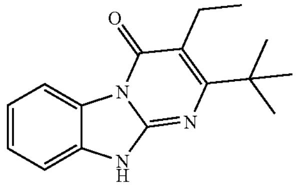

Chemical Formula: $C_{16}H_{19}N_3O$
Eact Mass: 269.15

The title compound was synthesized according to Method F starting from 2-Aminobenzimidazole (200 mg, 1.50 mmol) and ethyl 2-ethyl-4,4-dimethyl-3-oxopentanoate (1.1 mol. equiv). Reaction time: 16 h. After removal of volatiles crude product was purified by silica gel column chromatography (30% of EtOAc in heptane) affording 30.2 mg (0.112 mmol; 7%) of product as an off-white solid. $^1$H NMR (DMSO, 300 MHz): δ (ppm) 1.15 (t, J=7.2 Hz, 3H), 1.46 (s, 9H), 2.76 (q, J=7.1 Hz, 2H), 7.29 (ddd, J=8.4, 5.6, 3.1 Hz, 1H), 7.44 (m, 2H), 8.45 (d, J=8.0 Hz, 1H), 12.78 (s, 1H). $^{13}$C NMR (DMSO, 75 MHz): δ (ppm) 13.91, 19.89, 30.48, 69.91, 110.80, 113.15, 121.40, 125.50, 126.20, 145.85, 160.54. HRMS (ESI): m/z $[M+H]^+$ calcd for $C_6H_{20}N_3O$: 270.16007, found: 270.1595.

2-Cyclopropyl-3-ethylbenzo[4,5]imidazo[1,2-a]pyrimidin-4(10H)-one

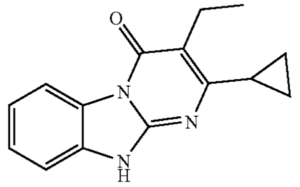

Chemical Formula: $C_{15}H_{15}N_3O$
Eact Mass: 253.12

The title compound was synthesized according to Method F starting from 2-aminobenzimidazole (146 mg, 1.10 mmol) and ethyl 2-(cyclopropanecarbonyl)butanoate (1.1 mol. equiv). Reaction time: 60 h. After removal of volatiles, crude product was purified by column chromatography (30% of EtOAc in heptane) affording 34 mg (0.134 mmol; 12%) of product as a white solid. $^1$H NMR (DMSO-$d_6$, 300 MHz): δ (ppm) 1.02 (m, 4H), 1.12 (t, J=7.4 Hz, 3H), 2.17 (m, 1H), 2.72 (q, J=7.4 Hz, 2H), 7.28 (m, 1H), 7.41 (m, 2H), 8.44 (d, J=7.9 Hz, 1H), 12.54 (br, 1H). $^{13}$C NMR (pyridine-$d_5$, 75 MHz): δ (ppm) 10.17, 14.78, 19.55, 30.92, 71.79, 111.73, 114.31, 117.46, 122.46, 126.85, 132.65, 149.85, 160.95, 164.22. HRMS (ESI): m/z $[M+H]^+$ calcd for $C_5H_6N_3O$: 254.12878, found: 254.1292.

3-Ethyl-2-isobutylbenzo[4,5]imidazo[1,2-a]pyrimidin-4(10H)-one

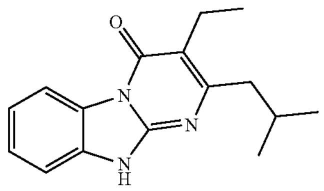

Chemical Formula: $C_{16}H_{19}N_3O$
Eact Mass: 269.15

The title compound was synthesized according to Method F starting from 2-aminobenzimidazole (300 mg, 2.25 mmol) and ethyl 2-ethyl-5-methyl-3-oxohexanoate (1.1 mol. equiv). Reaction time: 60 h. After removal of volatiles crude product was purified by column chromatography (50% of EtOAc in heptane). The fractions contained product were combined and concentrated to dryness. Resulting solid was suspended in a minimal amount of MeOH, the solid was collected by filtration and purified by column chromatography (heptane:EtOAc—7:3) yielding 79 mg (0.293 mmol; 13%) of product as a white solid. $^1$H NMR (pyridine-$d_5$, 300 MHz): δ (ppm) 0.98 (d, J=6.6 Hz, 6H), 1.31 (t, J=7.4 Hz, 3H), 2.29 (sept, J=6.9 Hz, 1H), 2.62 (d, J=7.3 Hz, 2H), 2.80 (q, J=7.3 Hz, 2H), 7.31 (t, J=7.7 Hz, 1H), 7.43 (t, J=7.7 Hz, 1H), 7.62 (d, J=8.0 Hz, 1H), 8.93 (d, 1H, J=7.9 Hz). $^{13}$C NMR (pyridine-$d_5$, 75 MHz): δ (ppm) 13.87, 18.68, 22.04, 28.06, 29.40, 41.53, 112.24, 113.06, 115.71, 120.76, 125.22, 136.01, 147.54, 156.38, 160.12. HRMS (ESI): m/z $[M+H]^+$ calcd for $C_{1\text{-}6}H_{20}N_3O$: 270.16007, found: 270.1606.

3-Ethyl-2-phenylbenzo[4,5]imidazo[1,2-a]pyrimidin-4(10H)-one

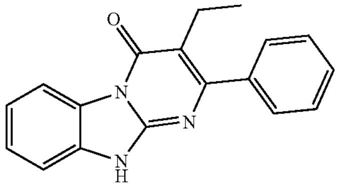

Chemical Formula: $C_{18}H_{15}N_3O$
Eact Mass: 289.12

The title compound was synthesized according to Method F starting from 2-aminobenzimidazole (232 mg, 1.75 mmol) and ethyl 2-benzoylbutanoate (1.1 mol. equiv). Reaction time: 60 h. After removal of volatiles crude product was purified on silica gel column (30% of EtOAc in heptane). Fractions containing product were combined and concentrated till dryness. The residue was suspended in a mixture heptane and EtOAc (7:3, v/v) and the precipitate was filtered off. Solid was suspended in 10 ml of MeOH, filtered and dried yielding 35 mg (0.121 mmol; 7%) of product as a white solid. $^1$H NMR (DMSO-$d_6$, 300 MHz): δ (ppm) 1.09 (t, J=7.1 Hz, 3H), 2.45 (q, J=6.9H, 2H), 7.34 (m, 1H), 7.51 (m, 7H), 8.51 (d, J=8.1 Hz, 1H). $^{13}$C NMR (pyridine-$d_5$, 75 MHz): δ (ppm) 14.12, 19.69, 99.66, 115.69, 121.52, 126.18, 128.27, 128.33, 128.69. HRMS (ESI): m/z $[M+H]^+$ calcd for $C_{18}H_{16}N_3O$: 290.1288, found: 290.1292.

Regioselective Synthesis of 3-ethyl-2-isopropyl-7-methyl- and 3-ethyl-2-isopropyl-8-methylbenzo[4,5]imidazo[1,2-a]pyrimidin-4(10H)-one Scheme. Regioselective synthesis of 3-ethyl-2-isopropyl-7-methyl- and 3-ethyl-2-isopropyl-8-methylbenzo[4,5]imidazo[1,2-a]pyrimidin-4(10H)-one.

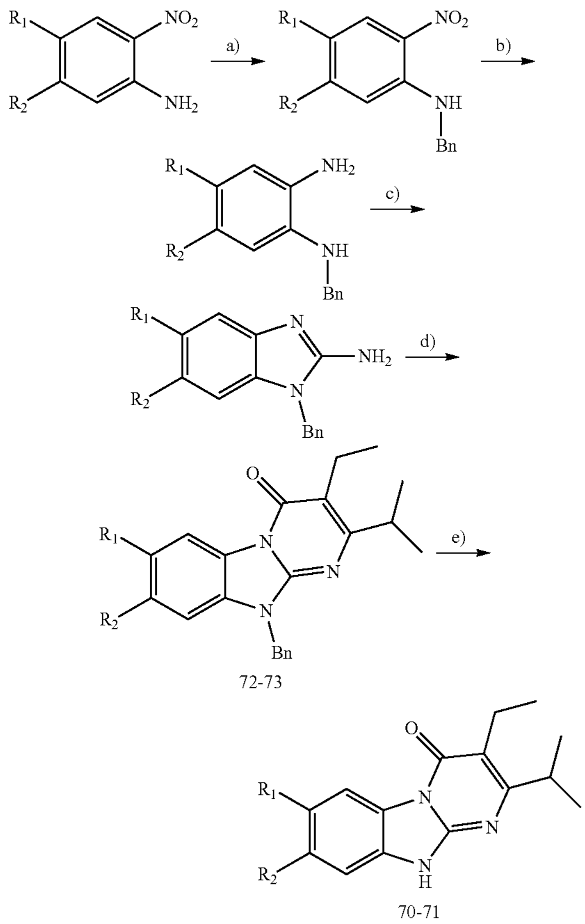

72-73

70-71

$R_1$ = Me, $R_2$ = H $R_1$ = H, $R_2$ = Me

Reagents and conditions: a) BnBr, $H_2O$, reflux; b) Raney nickel, $H_2$, MeOH, rt; c) BrCN, EtOH, 50° C.; d) DMF, reflux; e) $H_2$, Pd/C, $CH_2Cl_2$, MeOH, rt.

N-Benzyl-4-methyl-2-nitroaniline

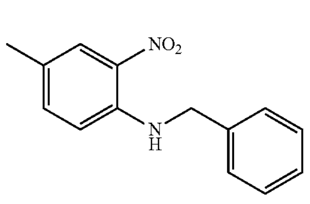

Chemical Formula: $C_{14}H_{14}N_2O_2$
Exact Mass: 242.11

Mixture of 4-methyl-2-nitroaniline (1 g, 6.57 mmol) and benzyl bromide (940 μl, 7.89 mmol, 1.2 mol. Equiv.) in $H_2O$ was stirred at reflux for 1.5 h. Then additional 0.6 mol. equiv. (3.95 mmol) of benzyl bromide was added and stirring was continued at reflux for 2 days. After cooling to room temperature, saturated $NaHCO_3$ was added and mixture was extracted with EtOAc (3×). Organic layers were combined, washed with $H_2O$ (1×) and dried over $Na_2SO_4$. After removal of drying agent and solvent, residue was subjected to silica gel column chromatography (heptane: EtOAc—9:1) affording 1.29 g (5.33 mmol; 81%) of product as an orange solid. $^1H$ NMR ($CDCl_3$, 300 MHz): δ (ppm) 2.25 (s, 3H), 4.53 (d, J=5.0 Hz, 2H), 6.73 (d, J=7.5 Hz, 1H), 7.20 (dd, J=7.5, 2.5 Hz, 1H), 7.25-7.38 (m, 5H), 7.99 (d, J=2.5 Hz, 1H), 8.33 (br, 1H). $^{13}C$ NMR ($CDCl_3$, 75 MHz): δ (ppm) 19.09, 46.25, 113.34, 124.42, 125.23, 126.13, 126.74, 128.01, 131.04, 136.75, 136.83, 142.63. HRMS (ESI): m/z $[M+Na]^+$ calcd for $C_{14}H_{14}N_2O_2Na$: 265.0948, found 265.0950.

$N^1$-Benzyl-4-methylbenzene-1,2-diamine

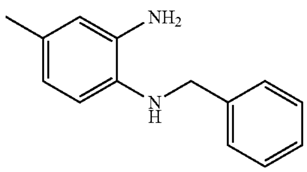

Chemical Formula: $C_{14}H_{16}N_2$
Exact Mass: 212.13

To a solution of N-benzyl-4-methyl-2-nitroaniline (420 mg, 1.71 mmol) in methanol was added a slurry of Raney nickel (30 mg) and the mixture was stirred vigorously. The flask was flushed with $H_2$ gas 3 times. The reaction mixture was allowed to stir for 3 h. The catalyst was removed by filtration through Celite and the reaction was concentrated in vacuo, yielding the title compound (1.68 mmol, 98%) as a colorless oil which was immediately used in the next reaction. $^1H$ NMR ($CDCl_3$, 300 MHz): δ (ppm) 2.19 (s, 3H), 3.36 (br, 3H), 4.23 (s, 2H), 6.50-6.58 (m, 3H), 7.22-7.34 (m, 5H).

1-Benzyl-5-methyl-1H-benzo[d]imidazol-2-amine

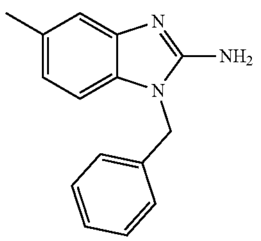

Chemical Formula: $C_{15}H_{15}N_3$
Exact Mass: 237.13

The title product was synthesized from $N^1$-benzyl-4-methylbenzene-1,2-diamine (500 mg, 2.36 mmol) according to the Method D affording 294 mg (1.24 mmol, 52%) of product as a white solid. $^1H$ NMR (DMSO, 300 MHz): δ

(ppm) 2.29 (s, 3H), 5.22 (s, 2H), 6.46 (s, 2H), 6.63 (d, J=7.8 Hz, 1H), 6.92 (m, 2H), 7.22 (m, 5H).

10-Benzyl-3-ethyl-2-isopropyl-7-methylbenzo[4,5]imidazo[1,2-a]pyrimidin-4(10H)-one

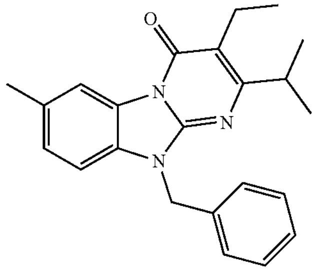

Chemical Formula: $C_{23}H_{25}N_3O$
Exact Mass: 359.20

The title compound was synthesized according to Method F starting from 1-benzyl-5-methyl-1H-benzo[d]imidazol-2-amine (200 mg, 0.842 mmol) and ethyl 2-ethyl-4-methyl-3-oxopentanoate (1.1 mol. equiv). Reaction time: 16 h. After removal of volatiles crude product was purified on silica gel column (heptane:EtOAc—9:1) affording 96 mg (0.267 mmol; 32%) of product as an off-white solid. $^1$H NMR (DMSO-$d_6$, 300 MHz): δ (ppm) 1.08 (t, J=7.4 Hz, 3H), 1.24 (d, J=6.6 Hz, 6H), 2.62 (m, 2H), 3.23 (m, 1H), 5.46 (s, 2H), 7.17 (t, J=9.1 Hz, 1H), 7.31 (m, 3H), 7.50 (m, 2H), 7.69 (d, J=9.3 Hz, 1H), 8.45 (m, 1H).

3-Ethyl-2-isopropyl-7-methylbenzo[4,5]imidazo[1,2-a]pyrimidin-4(10H)-one

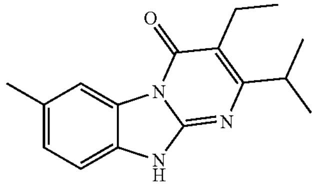

Chemical Formula: $C_{16}H_{19}N_3O$
Exact Mass: 269.15

To a solution of 10-benzyl-3-ethyl-2-isopropyl-7-methylbenzo[4,5]imidazo[1,2-a]pyrimidin-4(10H)-one (50 mg, 0.139 mmol) in a mixture of $CH_2Cl_2$ and MeOH (1:1, v/v) was added Pd/C catalyst (10 mol %). The reaction was flushed with $H_2$ gas and stirred for 5 hours. The mixture was filtered through Celite and the solvent was evaporated. The crude product was purified on silica gel column (heptane:EtOAc—7:3) yielding 22 mg of the title compound (0.082 mmol, 58%) as a white solid. $^1$H NMR (DMSO-$d_6$, 300 MHz): δ (ppm) 1.07 (t, J=7.4 Hz, 3H), 1.22 (d, J=6.7 Hz, 6H), 2.45 (s, 3H), 2.60 (m, 2H), 3.21 (m, 1H), 7.28 (m, 2H), 8.28 (s, 1H), 12.57 (br, 1H). $^{13}$C NMR (DMSO-$d_6$, 75 MHz): δ (ppm) 14.68, 17.89, 21.28, 21.65, 30.68, 110.95, 115.72, 126.25, 126.85, 130.61, 147.77, 159.78. HRMS (ESI): m/z $[M+H]^+$ calcd for $C_6H_{20}N_3O$: 270.1601, found: 270.1606.

N-Benzyl-5-methyl-2-nitroaniline

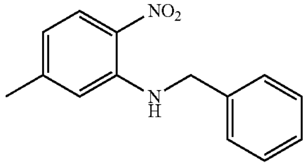 [SMILES: Cc1ccc([N+](=O)[O-])c(NCc2ccccc2)c1]

Mixture of 5-methyl-2-nitroaniline (1.0 g, 6.57 mmol) and benzyl bromide (940 μl, 7.89 mmol, 1.2 mol. equiv) in $H_2O$ was stirred at reflux for 1.5 h. Then additional 0.6 eq (3.95 mmol) of benzyl bromide was added and stirring was continued at reflux for 2 days. After cooling to room temperature, saturated $NaHCO_3$ was added and mixture was extracted with EtOAc (3×). Organic layers were combined, washed with $H_2O$ (1×) and dried over $Na_2SO_4$. After removal of drying agent and solvent, residue subjected to silica gel column separation (heptane:EtOAc—9:1) affording 1.08 g (4.46 mmol; 68%) of product as an orange solid. $^1$H NMR (DMSO-$d_6$, 300 MHz): δ (ppm) 2.23 (s, 3H), 4.63 (s, 2H), 6.54 (d, J=10.3 Hz, 1H), 7.32 (m, 5H), 6.78 (s, 1H), 7.98 (d, J=8.7 Hz, 1H), 8.64 (br, 1H).

$N^1$-Benzyl-5-methylbenzene-1,2-diamine

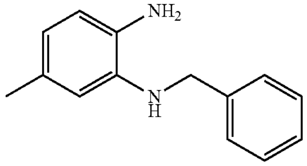 [SMILES: Cc1ccc(N)c(NCc2ccccc2)c1]

To a solution of N-benzyl-5-methyl-2-nitroaniline (420 mg, 1.71 mmol) in MeOH was added a slurry of Raney nickel (30 mg) and the mixture was stirred vigorously. The flask was flushed with $H_2$ gas 3 times. The reaction was allowed to stir for 3 hours. The catalyst was removed by filtration through Celite and the reaction was concentrated in vacuo, yielding the title compound as a colorless oil (1.68 mmol, 98%). $^1$H NMR (DMSO-$d_6$, 300 MHz): δ (ppm) 2.04 (s, 3H), 4.26 (s, 4H), 4.99 (s, 1H), 6.21 (d, J=7.2 Hz, 2H), 6.45 (d, J=7.6 Hz, 1H), 7.32 (m, 6H).

1-Benzyl-6-methyl-1H-benzo[d]imidazol-2-amine

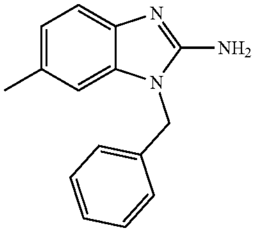 [SMILES: Cc1ccc2nc(N)n(Cc3ccccc3)c2c1]

The title compound was synthesized from N-benzyl-5-methylbenzene-1,2-diamine (400 mg, 1.88 mmol) according to the Method D affording 220 mg (0.927 mmol, 49%) of product as a white solid. $^{1}$H NMR (DMSO-$d_6$, 300 MHz): δ (ppm) 2.27 (s, 3H), 5.22 (s, 2H), 6.40 (s, 2H), 6.74 (d, J=7.9 Hz, 1H), 6.85 (s, 1H), 7.02 (d, J=8.3 Hz, 1H), 7.26 (m, 5H).

10-Benzyl-3-ethyl-2-isopropyl-8-methylbenzo[4,5]imidazo[1,2-a]pyrimidin-4(10H)-one

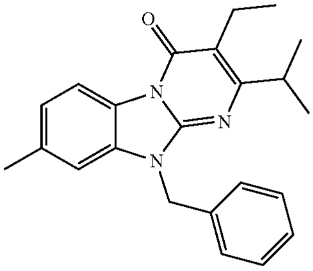 [SMILES: CCc1c(C(C)C)nc2n(Cc3ccccc3)c3cc(C)ccc3n2c1=O]

The title compound was synthesized according to Method F starting from compound 1-benzyl-6-methyl-1H-benzo[d]imidazol-2-amine (260 mg, 1.10 mmol) and ethyl 2-ethyl-4-methyl-3-oxopentanoate (1.1 mol. equiv). Reaction time: 16 h. After removal of volatiles crude product was purified on silica gel column (heptane:EtOAc—9:1) affording 183 mg (0.509 mmol; 46%) of product as an off-white solid. $^{1}$H NMR ($CDCl_3$, 300 MHz): δ (ppm) 1.19 (t, J=7.5 Hz, 3H), 1.29 (d, J=6.6 Hz, 6H), 2.45 (s, 3H), 2.73 (q, J=7.5 Hz, 2H), 3.25 (sept, J=6.6 Hz, 1H), 5.39 (s, 2H), 7.02-7.44 (m, 7H), 8.49 (d, J=8.1 Hz, 1H).

3-Ethyl-2-isopropyl-8-methylbenzo[4,5]imidazo[1,2-a]pyrimidin-4(10)-one

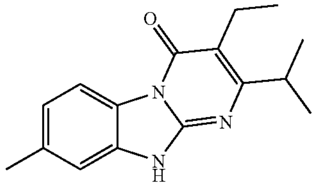

Chemical Formula: $C_{16}H_{19}N_3O$
Exact Mass: 269.15

To a solution of 10-benzyl-3-ethyl-2-isopropyl-7-methylbenzo[4,5]imidazo[1,2-a]pyrimidin-4(10H)-one (183 mg, 0.509 mmol) in a mixture of $CH_2Cl_2$ and MeOH (1:1) was added Pd/C catalyst (10 mol %). The reaction was flushed with $H_2$ gas and stirred for 5 hours. The mixture was filtered through Celite and the solvent was evaporated. The crude product was purified on silica gel column (heptane:EtOAc—7:3) yielding 74 mg of the title compound (0.274 mmol, 54%) as a white solid. $^{1}$H NMR (DMSO-$d_6$, 300 MHz): δ (ppm) 1.07 (t, J=7.0 Hz, 3H), 1.21 (d, J=6.2 Hz, 6H), 2.44 (s, 3H), 2.57 (q, J=6.9 Hz, 2H), 3.19 (m, 1H), 7.09 (d, J=8.2 Hz, 1H) 7.21 (s, 1H), 8.29 (d, J=8.1 Hz, 1H), 12.53 (br, 1H). $^{13}$C NMR (DMSO-$d_6$, 75 MHz): δ (ppm) 14.68, 17.87, 21.44, 21.69, 30.70, 111.26, 115.20, 122.31, 135.71, 147.75, 159.61. HRMS (ESI): m/z $[M+H]^+$ calcd for $C_6H_{20}N_3O$: 270.1601, found: 270.1592.

Synthesis of 3-Substituted 2-methylbenzo[4,5]imidazo[1,2-a]pyrimidin-4(10H)-ones Scheme Synthesis of 3-substituted 2-methylbenzo[4,5]imidazo[1,2-a]pyrimidin-4(10H)-ones.

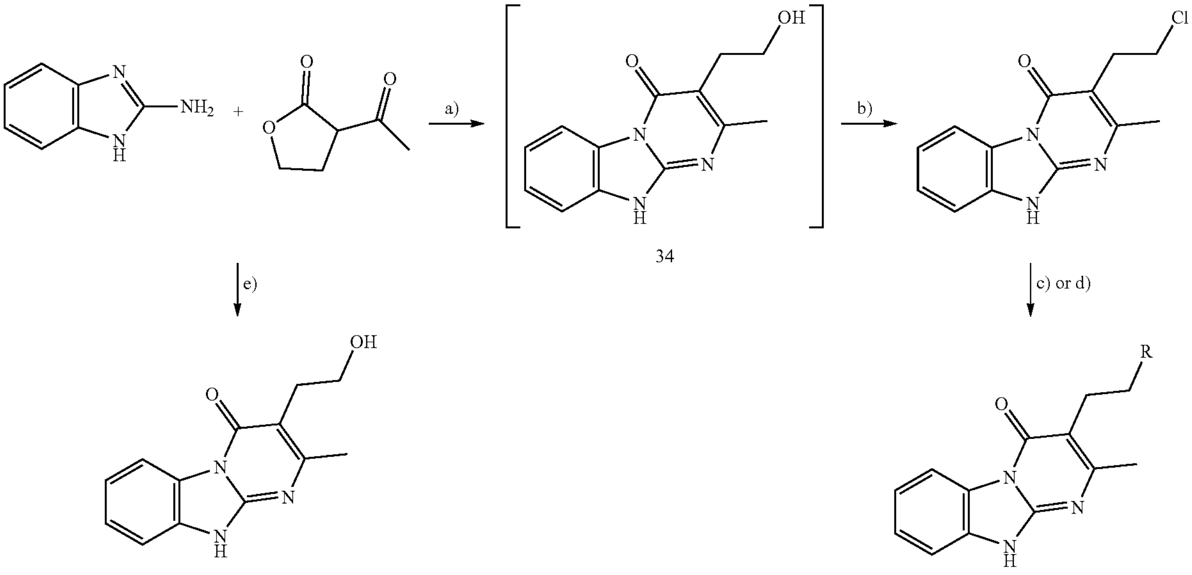

34

34

68: R = $NCH_3$
69: R = $N_3$

Reagents and conditions: a) p-TsOH monohydrate, toluene, reflux; b) $POCl_3$, reflux; c) 40% aqueous $MeNH_2$, 90° C.; d) $NaN_3$, 90° C.; e) DMF, reflux.

3-(2-Hydroxyethyl)-2-methylbenzo[4,5]imidazo[1,2-a]pyrimidin-4(10H)-one

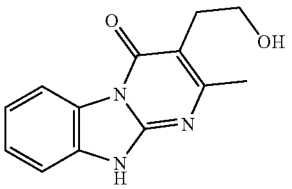

Chemical Formula: $C_{13}H_{13}N_3O_2$
Exact Mass: 243.10

The title compound was synthesized according to Method F starting from 2-aminobenzimidazole (100 mg, 0.751 mmol) and 2-acetyl-γ-butyrolactone (1 mol. equiv). Reaction time: overnight. DMF was removed under reduced pressure and crude product was purified using flash column chromatography on silica gel (2-5% of MeOH in $CH_2Cl_2$) affording 49 mg (0.201 mmol, 27%) of product as brown solid. $^1$H NMR (DMSO-$d_6$, 600 MHz): δ (ppm) 2.38 (s, 3H), 2.69 (t, 2H, J=7.2 Hz), 3.51-3.54 (m, 2H), 4.61 (br, 1H), 7.27 (td, 1H, J=8.4 Hz, J=1.2 Hz), 7.41 (td, 1H, J=7.8 Hz, J=1.2 Hz), 7.51 (d, 1H, J=7.8 Hz), 8.39 (d, 1H, J=7.8 Hz), 12.56 (br, 1H). $^{13}$C NMR (DMSO-$d_6$, 150 MHz): δ (ppm) 19.74, 28.85, 59.73, 106.08, 113.90, 115.02, 120.97, 125.41, 126.99, 136.28, 146.75, 154.69, 159.65. HRMS (ESI): m/z $[M+H]^+$ calcd for $C_{13}H_4N_3O_2$: 244.1080, found: 244.1081.

3-(2-Chloroethyl)-2-methylbenzo[4,5]imidazo[1,2-a]pyrimidin-4(10H)-one 0

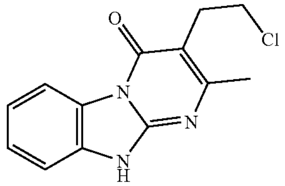

Chemical Formula: $C_{13}H_{12}ClN_3O$
Exact Mass: 261.07

Mixture of 2-aminobenzimidazole (666 mg; 5 mmol), 2-acetyl-γ-butyrolactone (539 μl; 5 mmol) and p-toluenesulfonic acid monohydrate (15 mg) in 10 ml of toluene was refluxed for 20 h. Solid was filtered-off and dried in vacuo at 80° C. for 15 h. Crude product was refluxed in $POCl_3$ (15 ml) for 3 h. Excess of $POCl_3$ was removed in vacuo. Ice-cold water was added to the residue, mixture was brought to pH 8-9 using solid $Na_2CO_3$ and stirred for further 2 h. Solid was filtered-off, washed with water and dried. Crude product was purified on silica gel column ($CH_2Cl_2$:MeOH—100:3). Fractions containing product were combined and concentrated. Solid was suspended in MeOH, filtered-off and dried affording 516 mg (1.971 mmol; 39% after 2 steps) of product as a pale yellow solid. $^1$H NMR (DMSO-$d_6$, 300 MHz): δ (ppm) 2.40 (s, 3H), 2.99 (t, J=7.5 Hz, 2H), 3.76 (t, J=7.5 Hz, 2H), 7.27-7.32 (m, 1H), 7.44 (td, J=7.5, 1.2 Hz, 1H), 7.52 (d, J=7.5 Hz, 1H), 8.39 (d, J=8.1 Hz, 1H), 12.75 (s, 1H). $^{13}$C NMR (DMSO-$d_6$, 75 MHz): δ (ppm) 20.25, 28.82, 43.09, 105.58, 113.33, 115.12, 121.29, 125.66, 126.60, 134.88, 146.87, 156.75, 159.28. HRMS (ESI): m/z $[M+H]^+$ calcd for $C_{13}H_{13}N_3ClO$: 262.0742, found: 262.0741, 264.0719.

2-Methyl-3-(2-(methylamino)ethyl)benzo[4,5]imidazo[1,2-a]pyrimidin-4(10H)-one

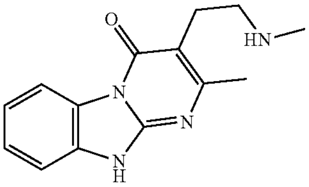

Chemical Formula: $C_{14}H_{16}N_4O$
Exact Mass: 256.13

Mixture of 3-(2-chloroethyl)-2-methylbenzo[4,5]imidazo[1,2-a]pyrimidin-4(10H)-one (50 mg; 0.191 mmol) and 40% aqueous $MeNH_2$ (2 ml) was stirred at 90° C. for 2.5 h. Volatiles were removed under reduced pressure and crude product was purified using column chromatography on silica gel (16-20% MeOH in $CH_2Cl_2$ with 1.5% (vol.) addition of 7 N ammonia in MeOH) afforded 30 mg (0.117 mmol; 61%) of product as an off-white solid. $^1$H NMR (DMSO-$d_6$, 300 MHz): δ (ppm) 2.29 (s, 3H), 2.54 (s, 3H), 2.79 (br t, J=6.9 Hz), 2H, 2.93 (br t, J=6.9 Hz, 2H), 6.50 (br, 2H), 7.05 (td, J=8.1, 0.9 Hz, 1H), 7.26 (td, J=8.1, 1.2 Hz, 1H), 7.45 (d, J=7.8 Hz, 1H), 8.35 (d, J=7.8 Hz, 1H). $^{13}$C NMR (DMSO-$d_6$, 75 MHz): δ (ppm) 21.47, 23.68, 33.85, 49.25, 101.77, 114.42, 114.77, 118.39, 124.01, 127.68, 140.38, 151.62, 158.30, 160.73. HRMS (ESI): m/z $[M+H]^+$ calcd for $C_{14}H_7N_4O$: 257.1397, found: 257.1398.

3-(2-Azidoethyl)-2-methylbenzo[4,5]imidazo[1,2-a]pyrimidin-4(10H)-one

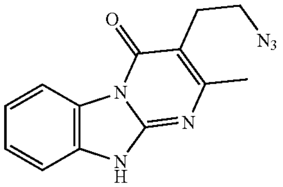

Chemical Formula: $C_{13}H_{12}N_6O$
Exact Mass: 268.11

Mixture of 3-(2-chloroethyl)-2-methylbenzo[4,5]imidazo[1,2-a]pyrimidin-4(10H)-one (50 mg; 0.191 mmol) and $NaN_3$ (25 mg; 0.382 mol) in DMF (2 ml) was stirred at 90° C. for 18 h (product and starting material has the same $R_f$ value in various solvent system). Volatiles were removed in vacuo and crude product was purified on silica gel column (1-2% of MeOH in $CH_2Cl_2$) afforded 27 mg (0.101 mmol; 53%) of product as an off-white solid. $^1$H NMR (DMSO-$d_6$, 300 MHz): δ (ppm) 2.38 (s, 3H), 2.79 (t, J=7.2 Hz, 2H), 3.46 (t, J=7.2 Hz, 2H), 7.22 (m, 1H), 7.42 (td, J=7.8, 0.9 Hz, 1H), 7.49 (bd, J=7.8 Hz, 1H), 8.38 (d, J=7.8 Hz, 1H). $^{13}$C NMR (DMSO-$d_6$, 75 MHz): δ (ppm) 20.04, 24.98, 49.39, 105.44, 113.36, 115.11, 121.20, 125.60, 126.64, 135.04, 146.89, 156.26, 159.36. HRMS (ESI): m/z $[M+H]^+$ calcd for $C_{13}H_{13}N_6O$: 269.1145, found: 269.1144.

Synthesis of benzo[4,5]imidazo[1,2-a][1,3,5]triazin-4-amine

Scheme. Synthesis of benzo[4,5]imidazo[1,2-a][1,3,5]triazin-4-amine.

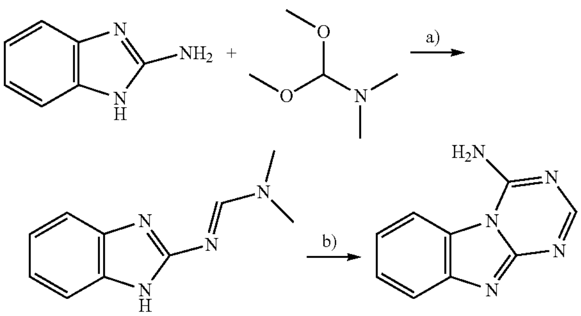

Reagents and conditions: a) $CHCl_3$, reflux; b) NaOMe, MeOH, $H_2NCN$, reflux.

$N^1$,$N^1$-Dimethyl-$N^2$-benzimidazolyl-2-formamidine

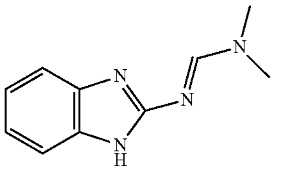

Chemical Formula: $C_{10}H_{12}N_4$
Exact Mass: 188.11

Mixture of 2-aminobenzimidazole (1.5 g, 11.26 mmol) and N,N-dimethylformamide dimethyl acetal (1.1 mol. equiv.) in $CHCl_3$ (10 ml) was heated at reflux for 24 h. Volatiles were removed under reduced pressure and solid residue was chromatographed on silica gel (10% of MeOH in $CH_2Cl_2$) affording 2.03 g (10.78 mmol, 96%). $^1$H NMR (DMSO-$d_6$, 300 MHz): δ (ppm) 3.01 (s, 3H), 3.13 (s, 3H), 6.94-6.96 (m, 2H), 7.20-7.24 (m, 2H), 8.65 (s, 1H), 11.53 (br, 1H). $^{13}$C NMR (DMSO-$d_6$, 75 MHz): δ (ppm) 34.24, 40.18, 112.63 (br), 119.79, 157.56, 158.52. $^1$H NMR ($CDCl_3$, 300 MHz): δ (ppm) 3.09 (s, 3H), 3.12 (s, 3H), 7.07-7.13 (m, 2H), 7.38-7.40 (m, 2H), 8.78 (s, 1H), 11.53 (br, 1H. $^{13}$C NMR ($CDCl_3$, 75 MHz): δ (ppm) 34.96, 41.10, 112.05 (br), 121.13, 157.94, 158.29. HRMS (ESI): m/z $[M+H]^+$ calcd for $C_{10}H_{13}N_4$: 189.1135, found: 189.1139.

Benzo[4,5]imidazo[1,2-a][1,3,5]triazin-4-amine

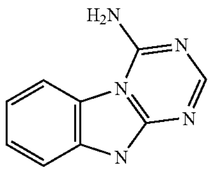

Chemical Formula: $C_9H_7N_5$
Exact Mass: 185.07

$N^1$,$N^1$-Dimethyl-$N^2$-benzimidazolyl-2-formamidine (200 mg, 1.062 mmol) and cyanamide (2 mol. equiv.) were added to the solution of metallic sodium (2 mol. equiv.) dissolved in anhydrous MeOH (3.5 ml). Resulting mixture was heated at reflux for 24 h. Then volatiles were removed in vacuo. Solid residue was dissolved in $H_2O$ and acidified (to pH 3) using concentrated HCl. After 30 min of stirring at 0° C., solid was filtered-off, washed with $H_2O$ and recrystallized from DMF affording 108 mg (0.583 mmol, 55%) of title compound as a white solid. $^1$H NMR (DMSO-$d_6$, 300 MHz): δ (ppm) 7.37 (t, J=7.5 Hz, 1H), 7.51 (t, J=7.5 Hz, 1H), 7.74 (d, J=8.1 Hz, 1H), 8.26 (s, 1H), 8.41 (d, J=7.8 Hz, 1H), 8.61 (br, 2H). $^{13}$C NMR (DMSO-$d_6$, 75 MHz): δ (ppm) 114.16, 118.45, 121.36, 125.08, 125.85, 143.34, 154.08, 153.49, 159.09. HRMS (ESI): m/z $[M+H]^+$ calcd for $C_9H_8N$: 186.0774, found: 186.0777.

Synthesis of Examples A-2, A-3 and B-32

Scheme. The synthesis of 4-oxo-4,10-dihydrobenzo[4,5]imidazo [1,2-a]pyrimidine.

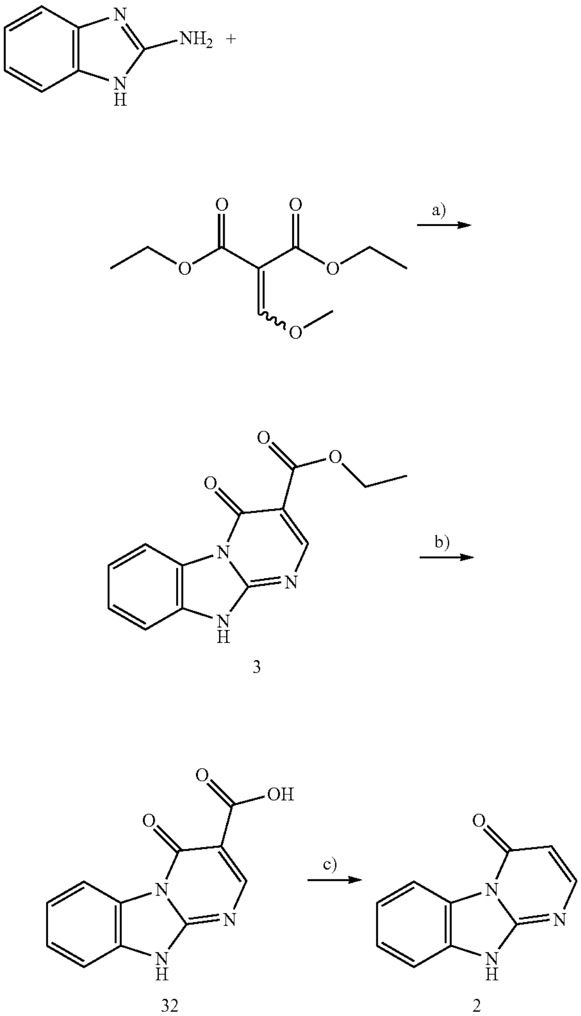

3

32

2

Reagents and conditions: a) MeOH, reflux; b) NaOH, $H_2O$, 85° C.; c) Cu powder, quinoline, 200° C.

Ethyl 4-oxo-4,10-dihydrobenzo[4,5]imidazo[1,2-a]pyrimidine-3-carboxylate

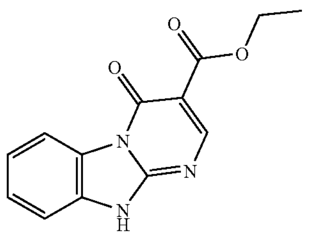

Chemical Formula: $C_{13}H_{11}N_3O_3$
Exact Mass: 257.08

Mixture of 2-aminobenzimidazole (500 mg, 3.756 mmol) and diethyl ethoxymethylenemalonate (829 mg, 3.831 mmol) in dry MeOH was heated at reflux for 5 h. The mixture was cooled down in an ice-water bath. Precipitate was collected by filtration. The crude product was purified by column chromatography on silica gel (2-20% gradient of MeOH in $CH_2Cl_2$ with 5% vol. addition of 7 N ammonia in MeOH). $^1$H NMR (DMSO-$d_6$, 300 MHz): δ (ppm) 1.30 (t, J=7.2 Hz, 3H), 4.25 (q, J=7.2 Hz, 2H), 7.39-7.45 (m, 1H), 7.53 (td, J=7.2, 0.9 Hz, 1H), 7.58 (br d, J=8.1 Hz, 1H), 8.51 (d, J=8.1 Hz, 1H), 8.68 (s, 1H). $^{13}$C NMR (DMSO-$d_6$, 75 MHz): δ (ppm) 14.32, 59.66, 103.41, 112.49, 116.05, 122.76, 126.34, 126.69, 131.58, 150.61, 156.28, 158.63, 164.27. HRMS (ESI): m/z $[M+H]^+$ calcd for $C_{13}H_{12}N_3O_3$: 258.0873, found: 258.0879.

4-Oxo-4,10-dihydrobenzo[4,5]imidazo[1,2-a]pyrimidine-3-carboxylic Acid

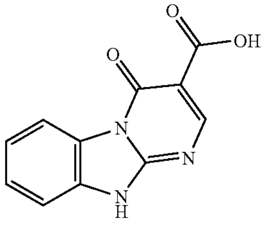

Chemical Formula: $C_{11}H_7N_3O_3$
Exact Mass: 229.05

Mixture of ethyl 4-oxo-4,10-dihydrobenzo[4,5]imidazo[1,2-a]pyrimidine-3-carboxylate (99 mg, 0.385 mmol) and 0.2 M aqueous NaOH (5.4 ml) was heated at 85° C. for 2.5 h. Next, the mixture was cooled in an ice-water bath and acidified using concentrated HCl. Precipitate was filtered-off, washed with $H_2O$ and dried affording 54 mg (0.236 mmol, 61%) of title compound as pale yellow solid.

$^1$H NMR (DMSO-$d_6$, 300 MHz): δ (ppm) 7.48 (br t, J=7.2 Hz, 1H), 7.53 (m, 1H), 7.57-7.66 (m, 2H), 8.48 (d, J=7.8 Hz, 1H), 8.77 (s, 1H), 13.19 (br, 1H). $^{13}$C NMR (DMSO-$d_6$, 75 MHz): δ (ppm) 102.48, 112.58, 116.17, 123.26, 126.00, 126.98, 131.14, 150.29, 159.14, 160.35, 165.04. HRMS (ESI): m/z $[M-H]^-$ calcd for $C_1H_6N_3O_3$: 228.0414, found: 228.0417.

Benzo[4,5]imidazo[1,2-a]pyrimidin-4(10H)-one

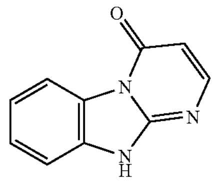

Chemical Formula: $C_{10}H_7N_3O$
Exact Mass: 185.06

Mixture of 4-oxo-4,10-dihydrobenzo[4,5]imidazo[1,2-a]pyrimidine-3-carboxylic acid (47 mg, 0.205 mmol) and Cu powder (8 mg) in quinoline (0.8 ml) was heated at 200° C. for 1 h. The hot mixture was filtered through paper filter and quinoline was removed by vacuum distillation. The residue was purified on silica gel column (2-4% gradient of MeOH in $CH_2Cl_2$). Fractions containing product were combined, concentrated and repurified using preparative TLC (3% of MeOH in $CH_2Cl_2$) affording 6 mg (0.032 mmol, 16%) of product as an off-white solid. $^1$H NMR (DMSO-$d_6$, 300 MHz): δ (ppm) 5.96 (d, J=6.9 Hz, 1H), 7.32 (td, J=8.1, 1.2 Hz, 1H), 7.47 (td, J=7.8, 1.2 Hz, 1H), 7.55 (br d, J=7.8 Hz, 1H), 7.96 (d, J=6.9 Hz, 1H), 8.43 (d, J=8.1 Hz, 1H), 12.96 (br, 1H). $^{13}$C NMR (DMSO-$d_6$, 75 MHz): δ (ppm) 100.07, 113.39, 115.40, 121.49, 125.77, 126.73, 134.67, 148.74, 149.03, 159.46. HRMS (ESI): m/z $[M+H]^+$ calcd for $C_{10}HN_3O$: 186.0662, found: 186.0662.

Synthesis of Example B-58

Scheme. The synthesis of 4H-benzo[4,5]imidazo[2,1-b][1,3]thiazin-4-one.

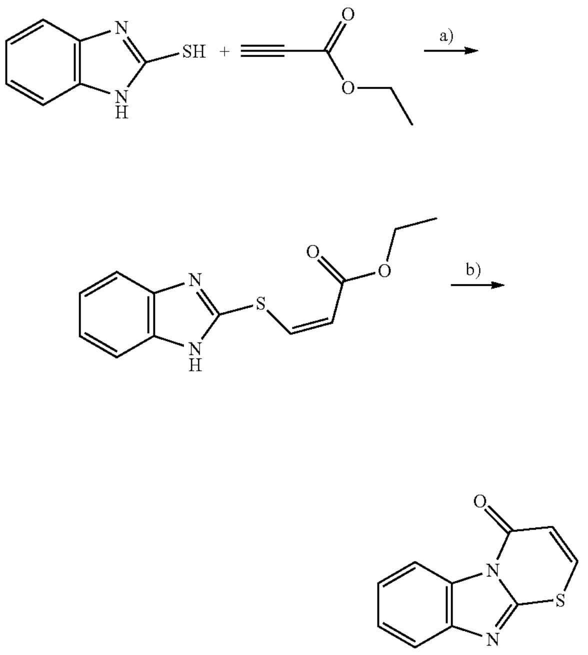

Reagents and conditions: a) EtOH, rt to 60° C.; b) $Ph_2O$, 220° C.

Ethyl (Z)-3-((1H-benzo[d]imidazol-2-yl)thio)acrylate

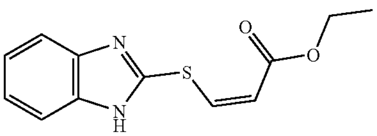

Chemical Formula: $C_{12}H_{12}N_2O_2S$
Exact Mass: 248.06

Mixture of 2-mercaptobenzimidazole (200 mg, 1,332 mmol) and ethyl propiolate (1.1 mol equiv.) in EtOH (3.3 ml) was stirred overnight at room temperature and next at 60° C. for 5 h. The mixture was concentrated in vacuo affording 312 mg (1.256 mmol, 94%) of crude product that was pure enough to be used in the next step without further purification. $^1H$ NMR (DMSO-$d_6$, 300 MHz): δ (ppm) 1.26 (t, J=7.2 Hz, 3H), 4.20 (q, J=7.2 Hz, 2H), 6.29 (d, J=9.9 Hz, 1H), 7.16-7.22 (m, 2H), 7.51-7.54 (m, 2H), 8.37 (d, J=9.9 Hz, 1H), 12.96 (br, 1H). $^{13}C$ NMR (DMSO-$d_6$, 75 MHz): δ (ppm) 14.12, 60.34, 115.18, 122.05, 141.89, 147.73, 165.93. HRMS (ESI): m/z $[M+H]^+$ calcd for $C_{12}H_{13}N_2O_2S$: 249.0692, found: 249.0680.

4H-benzo[4,5]imidazo[2,1-b][1,3]thiazin-4-one

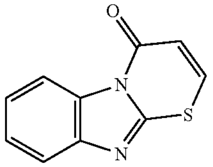

Chemical Formula: $C_{10}H_6N_2OS$
Exact Mass: 202.02

Ethyl (Z)-3-((1H-benzo[d]imidazol-2-yl)thio)acrylate (294 mg, 1.184 mmol) was heated in diphenyl ether (5 ml) at 220° C. for 4 h. After cooling to room temperature mixture was diluted with heptane (20 ml). The resulting solid was filtered-off, washed with heptane and dried under vacuum overnight affording crude product. Filtrate, heptane and ethereal washing were combined and kept at 4° C. for 48 h. Resulted precipitate was collected by filtration and dried affording additional amount of crude product. Combined precipitates were purified on silica gel column (0-50% AcOEt in heptane) affording 71 mg (0.351 mmol, 30%) of target compound as an off-white solid. H NMR ($CDCl_3$, 300 MHz): δ (ppm) 6.76 (d, J=10.4 Hz, 1H), 7.45 (td, J=7.7, 1.2 Hz, 1H), 7.51 (td, J=7.2, 1.2 Hz, 1H), 7.68 (d, J=10.4 Hz, 1H), 7.79 (d, J=7.5 Hz, 1H), 8.58 (d, J=8.0 Hz, 1H). $^{13}C$ NMR ($CDCl_3$, 75 MHz): δ (ppm) 116.29, 117.15, 118.62, 124.40, 126.03, 130.98, 134.88, 141.96, 146.21, 159.61. HRMS (ESI): m/z $[M+H]^+$ calcd for $C_{10}H_7N_2OS$: 203.0274, found: 203.0280.

Synthesis of Examples B-59-60

Scheme. Synthesis of 4H-benzo[4,5]oxazolo- and 4H-benzo[4,5]thiazolo[3,2-a]pyrimidin-4-one.

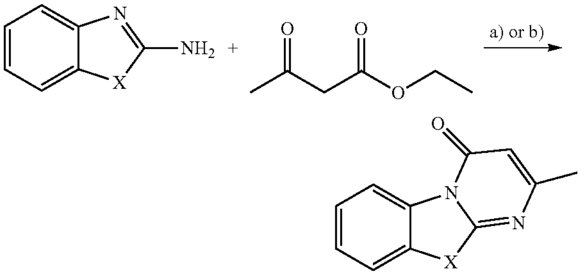

X = O or S

Reagents and conditions: a) Polyphosphoric acid (PPA), 120° C. (for both analogues); b) AcOH, reflux (only for thiazolo analogue).

2-Methyl-4H-benzo[4,5]oxazolo[3,2-a]pyrimidin-4-one

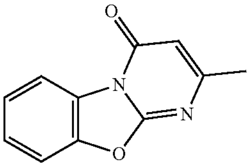

Chemical Formula: $C_{11}H_8N_2O_2$
Exact Mass: 200.06

A mixture of 2-aminobenzoxazole (200 mg, 1.491 mmol) and ethyl acetoacetate (1.1 mol. equiv.) in polyphosphoric acid (1.7 g) was heated at 120° C. overnight. After cooling the mixture in an ice-water bath, ice cold $H_2O$ was added to the flask and mixture was neutralized using 10 M aq. NaOH. Precipitate that formed was filtered-off, washed with $H_2O$ and dried. Crude product was suspended in MeOH, solid was filtered-off and dried affording 41 mg (0.205 mmol, 14%) of pale yellow solid.

Method Using AcOH:

A mixture of 2-aminobenzoxazole (200 mg, 1.491 mmol) and ethyl acetoacetate (1.5 mol. equiv.) in AcOH (1.7 ml) was heated at reflux for 15 h. Volatiles were removed under reduced pressure and the residue was brought pH ca. 8 using saturated aqueous $NaHCO_3$, and extracted with AcOEt. Organic layers were combined, washed with brine, dried over MgSO4, filtered and concentrated to dryness. The crude product was purified by silica gel column chromatography (0-10% gradient of AcOEt in $CH_2Cl_2$) affording 31 mg (0.155 mmol, 10%) of pale yellow solid.

$^1H$ NMR ($CDCl_3$, 300 MHz): δ (ppm) 2.42 (s, 3H), 6.24 (s, 1H), 7.42-7.55 (m, 3H), 8.38-8.41 (m, 1H). $^{13}C$ NMR ($CDCl_3$, 75 MHz): δ (ppm) 24.46, 106.44, 111.08, 116.66, 125.44, 126.31, 127.14, 144.71, 155.29, 159.47, 164.94. HRMS (ESI): m/z $[M+H]^+$ calcd for $C_{11}H_9N_2O_2$: 201.0658, found: 201.0662.

2-Methyl-4H-benzo[4,5]thiazolo[3,2-a]pyrimidin-4-one

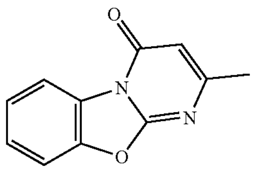

Chemical Formula: $C_{11}H_8N_2OS$
Exact Mass: 216.04

Mixture of 2-aminobenzothiazole (200 mg, 1.332 mmol) and ethyl acetoacetate (1.1 mol. equiv.) in polyphosphoric acid (PPA; 1.5 g) was heated at 120° C. overnight. After cooling the mixture in an ice-water bath, ice cold $H_2O$ was added to the flask and mixture was neutralized using 10 M aq. NaOH. Precipitate that formed was filtered-off, washed with $H_2O$ and dried. Crude product was suspended in MeOH, solid was filtered-off and dried affording 90 mg (0.416 mmol, 31%) of product as a pale yellow solid.

Method Using AcOH:

To a solution of 2-aminobenzothiazole (200 mg, 1.332 mmol) in AcOH (1.5 ml) was added ethyl acetoacetate (1.5 mol. equiv.) and resulting mixture was heated at reflux for 15 h. Volatiles were removed under reduced pressure and the residue was brought pH ca. 8 using saturated aqueous $NaHC_3$, and extracted with AcOEt. Organic layers were combined, washed with brine, dried over MgSO4, filtered and concentrated to dryness. The crude product was purified by silica gel column chromatography (0-10% gradient of AcOEt in $CH_2Cl_2$) affording 112 mg (0.518 mmol, 39%) of product as a pale yellow solid.

$^1H$ NMR ($CDCl_3$, 300 MHz): δ (ppm) 2.39 (s, 3H), 6.26 (s, 1H), 7.45-7.54 (m, 2H), 7.65-7.68 (m, 1H), 9.05-9.08 (m, 1H). $^{13}C$ NMR ($CDCl_3$, 75 MHz): δ (ppm) 23.84, 107.31, 120.19, 121.87, 124.22, 127.05, 127.14, 136.25, 161.30, 161.56, 163.02. HRMS (ESI): m/z $[M+H]^+$ calcd for $C_{11}H_9N_2OS$: 217.0430, found: 217.0436.

Synthesis of Example B-64

Scheme. Benzo[4,5]imidazo[1,2-a]pyrimidin-2(10H)-one.

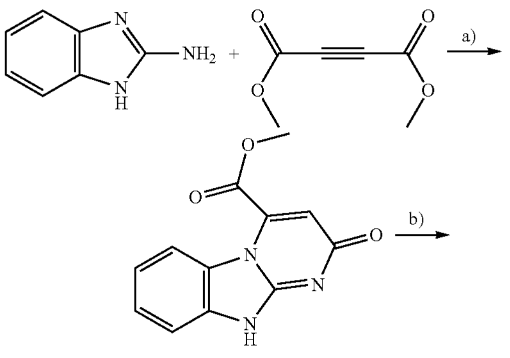

65

-continued

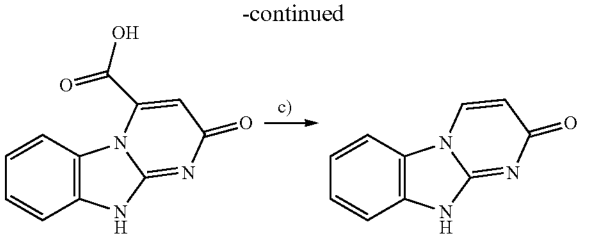

64

Reagents and conditions: a) MeOH, reflux; b) NaOH, $H_2O$, 85° C.; c) Cu powder, quinoline, 200° C.

Methyl 2-oxo-2,10-dihydrobenzo[4,5]imidazo[1,2-a]pyrimidine-4-carboxylate

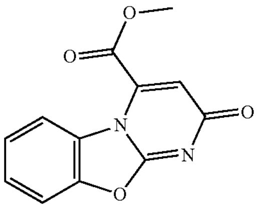

Chemical Formula: $C_{12}H_9N_3O_3$
Exact Mass: 243.06

Mixture of 2-aminobenzimidazole (200 mg, 1.502 mmol) and dimethyl acetylenedicarboxylate (271 mg, 1.903 mmol) in 4.5 ml of anhydrous MeOH was heated at reflux overnight. The mixture in an ice-water bath, precipitate was filtered-off and dried affording 245 mg (1.007 mmol, 67%) of the title compound as a yellow solid. $^1H$ NMR (DMSO-$d_6$, 300 MHz): δ (ppm) 4.06 (s, 3H), 6.52 (s, 1H), 7.22 (t, J=7.8 Hz, 1H), 7.35 (t, J=7.8 Hz, 1H), 7.53-7.58 (m, 2H). $^{13}C$ NMR (DMSO-$d_6$, 75 MHz): δ (ppm) 53.94, 109.56, 113.36, 116.53, 121.17, 124.64, 127.47, 137.52, 139.93, 148.02, 161.17, 161.76. HRMS (ESI): m/z $[M+H]^+$ calcd for $C_{12}H_{10}N_3O_3$: 244.0717, found: 244.0714.

2-Oxo-2,10-dihydrobenzo[4,5]imidazo[1,2-a]pyrimidine-4-carboxylic Acid

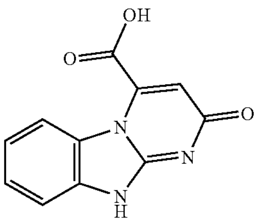

Chemical Formula: $C_{11}H_7N_3O_3$
Exact Mass: 229.05

Mixture of methyl 2-oxo-2,10-dihydrobenzo[4,5]imidazo[1,2-a]pyrimidine-4-carboxylate (206 mg, 0.799 mmol) and 0.2 M aqueous NaOH (3.8 ml) was heated at 85° C. for 2.5 h. Next, the mixture was cooled in an ice-water bath and acidified using concentrated HCl. Precipitate was filtered-off, washed with $H_2O$ and dried affording 153 mg (0.668 mmol, 84%) of an off-white solid. $^1$H NMR (DMSO-$d_6$, 300 MHz): δ (ppm) 6.44 (s, 1H), 7.23 (t, J=7.8 Hz, 1H), 7.36 (t, J=7.5 Hz, 1H), 7.55 (d, J=7.8 Hz, 1H), 7.69 (d, J=8.4 Hz, 1H). $^{13}$C NMR (DMSO-$d_6$, 75 MHz): δ (ppm) 107.58, 113.45, 116.50, 121.24, 124.71, 127.52, 139.84, 147.96, 162.22, 162.26. HRMS (ESI): m/z [M+H]$^+$ calcd for $C_{11}H_8N_3O_3$: 230.0560, found: 230.0552.

Benzo[4,5]imidazo[1,2-a]pyrimidin-2(10H)-one

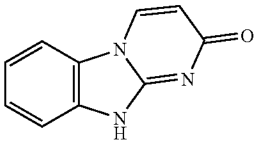

Chemical Formula: $C_{10}H_7N_3O$
Exact Mass: 185.06

A mixture of 2-oxo-2,10-dihydrobenzo[4,5]imidazo[1,2-a]pyrimidine-4-carboxylic acid (133 mg, 0.580 mmol) and Cu powder (22 mg) in quinoline (1.1 ml) was heated at 170° C. for 25 min. Then, the hot mixture was filtered through filter paper. After cooling to room temperature, filtrate was diluted with $Et_2O$. Solid was filtered-off, washed with ether and dried. The crude product was purified on silica gel column (2-5% gradient of MeOH in $CH_2Cl_2$) affording 38 mg (0.205 mmol, 35%) of title compound as an off-white solid. $^1$H NMR (DMSO-$d_6$, 300 MHz): δ (ppm) 6.11 (d, J=7.8 Hz, 1H), 7.22-7.34 (m, 2H), 7.52 (d, J=7.5 Hz, 1H), 7.90 (d, J=7.2 Hz, 1H), 8.79 (d, J=7.8 Hz, 1H), 12.59 (br, 1H). $^{13}$C NMR (DMSO-$d_6$, 75 MHz): δ (ppm) 105.80, 110.13, 117.01, 120.95, 124.15, 128.46, 134.75, 140.98, 147.28, 162.04. HRMS (ESI): m/z [M+H]$^+$ calcd for $C_{10}H_8N_3O$: 186.0662, found: 186.0664.

Inhibitory potency data of the compounds according to the invention are compiled in the following table:

| | β-arrestin assay (CHO β-arrestin human MrgX4 L83S) $IC_{50}$ ± [μM][a] (% inhibition ± SEM)[c] | calcium assay (LN229 cells recombinantly expressing human wildtype MrgX2 $IC_{50}$ ± SEM [μM][a] (% inhibition ± SEM)[d] |
|---|---|---|
| A-1 | >100 (4%) | |
| A-2 | >100 (18%) | |
| A-3 | >100 (25%) | |
| A-4 | >100 (35%) | |
| A-5 | >10 (−5%) | |
| A-6 | >10 (14%) | |
| A-7 | >100 (43%) | |
| A-8 | 11.6 ± 3.7 | 2.89 ± 0.24 |
| A-9 | 3.23 ± 0.36 | 0.662 ± 0.102 |
| A-10 | 2.42 ± 0.22 | 0.683 ± 0.174 |
| A-11 | >100 (37%) | |
| A-12 | >10 (−25%) | |
| A-13 | >100 (24%) | |
| A-14 | >10 (19%) | |
| A-15 | 1.40 ± 0.88 | >100 (3%) |
| A-16 | >100 (26%) | |
| A-17 | 3.22 ± 0.82 | >100 (70%) |
| A-18 | >100 (48%) | |
| A-19 | 14.7 ± 1.3 | >100 (27%) |
| A-20 | >100 (−2%) | |
| A-21 | 0.583 ± 0.049 | 0.0121 ± 0.0015 |
| A-22 | >100 (2%) | |
| A-23 | >10 (4%) | |

-continued

| | β-arrestin assay (CHO β-arrestin human MrgX4 L83S) $IC_{50}$ ± [μM][a] (% inhibition ± SEM)[c] | calcium assay (LN229 cells recombinantly expressing human wildtype MrgX2 $IC_{50}$ ± SEM [μM][a] (% inhibition ± SEM)[d] |
|---|---|---|
| A-24 | >100 (16%) | >100 (2%) |
| A-25 | >100 (22%) | |
| A-26 | >100 (−13%) | |
| A-27 | >100 (−18%) | |
| A-28 | >100 (4%) | |
| A-29 | >100 (−33%) | |
| A-30 | >10 (2%) | >100 (31%) |
| B-31 | >100 (40%) | |
| B-32 | >100 (45%) | |
| B-33 | >100 (24%) | |
| B-34 | >100 (22%) | >100 (−2%) |
| B-35 | >10 (20%) | |
| B-36 | >100 (48%) | >100 (10%) |
| B-37 | 0.290 ± 0.098 | 0.00248 ± 0.00075 |
| B-38 | >100 (15%) | 0.0540 ± 0.0192 |
| B-39 | 0.0877 ± 0.0368 | 0.0184 ± 0.0054 |
| B-40 | 0.0225 ± 0.0024 | 0.000420 ± 0.000054 |
| B-41 | 0.477 ± 0.087 | 0.00827 ± 0.00082 |
| B-42 | 0.512 ± 0.107 | >100 (68%) |
| B-43 | 0.278 ± 0.042 | |
| B-44 | 1.40 ± 0.36 | 0.199 ± 0.025 |
| B-45 | 0.214 ± 0.032 | >100 (89%) |
| B-46 | 0.250 ± 0.061 | |
| B-47 | 1.05 ± 0.11 | |
| B-48 | 0.0926 ± 0.0426 | |
| B-49 | 0.169 ± 0.017 | 0.0132 ± 0.0074 |
| B-50 | 0.129 ± 0.007 | |
| B-51 | 0.213 ± 0.079 | 0.0132 ± 0.0020 |
| B-52 | >100 | |
| B-53 | 0.0711 ± 0.0152 | |
| B-54 | 1.26 ± 0.31 | |
| B-55 | 5.66 ± 1.15 | >100 (20%) |
| B-56 | 0.148 ± 0.042 | 0.00394 ± 0.00167 |
| B-57 | >100 (−4%) | |
| B-58 | >100 (−44%) | |
| B-59 | >100 (13%) | |
| B-60 | >100 (14%) | |
| B-61 | >10 (2%) | |
| B-62 | >100 (18%) | |
| B-63 | >100 (6%) | |
| B-64 | >100 (0%) | |
| B-65 | >100 (48%) | |
| B-66 | >100 (4%) | |
| C-67 | 8.04 ± 1.63 | |
| C-68 | >100 (8%) | |
| C-69 | >100 (9%) | |
| C-70 | 0.147 ± 0.015 | 0.000352 ± 0.000070 |
| C-71 | 0.0910 ± 0.0292 | 0.000446 ± 0.000142 |
| C-72 | >10 (39%) | |
| C-73 | >10 (40%) | |
| C-74 | 0.0180 ± 0.0044 | 0.00126 ± 0.00029 |
| C-75 | 0.890 ± 0.184 | 0.0368 ± 0.0084 |
| C-76 | 0.349 ± 0.065 | |
| C-77 | 1.18 ± 0.33 | |
| C-78 | 0.468 ± 0.052 | 0.0513 ± 0.0191 |
| C-79 | 0.540 ± 0.076 | >10 (105%) |
| C-80 | >10 (34%) | |
| C-84 | 0.0582 ± 0.0189 | |
| C-85 | 0.223 ± 0.019 | |
| C-86 | 0.130 ± 0.029 | |
| C-87 | 0.246 ± 0.068 | |
| C-88 | 5.54 ± 1.74 | >10 (86%) |

The invention claimed is:

1. A method for treating a disease or disorder that is associated with the MrgX2 receptor, comprising administering to a subject in need thereof a therapeutically effective amount of an MrgX2 antagonist according to general formulas (II), (III), and (VII):

(II)

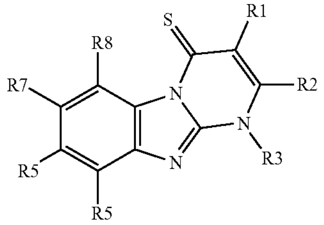

(III)

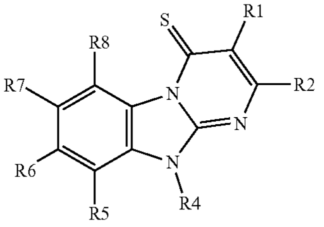

(III)

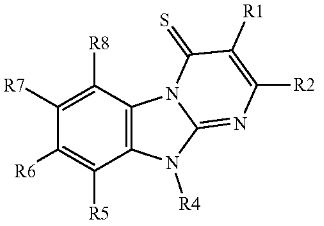

(VII)

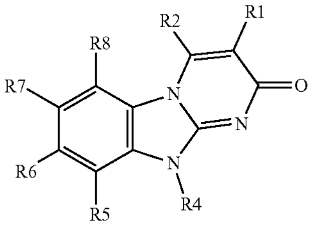

(VIII)

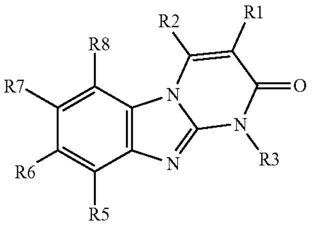

wherein

R1 means C1-3 alkyl, linear or branched, saturated or unsaturated, either unsubstituted or monosubstituted with —OH;

R2 means $CH(CH_3)_2$, $—CH_2CH(CH_3)_2$, $—C(CH_3)_3$, -cyclopropyl, -para-methoxyphenyl, -2-thienyl, $—CH_2C(=O)OH$, $—C(=O)OCH_3$, $—CH_2C(=O)OCH_3$, $—CH_2C(=O)OCH_2CH_3$, $—C(CH_3)_2(OH)$, $—CH_2OCH_3$, $—SCH_3$, or $—NH_2$; or R1 and R2 together with the atoms to which they are attached form a six membered saturated unsubstituted alicyclic ring;

R3, and R4 means —H; $—C_{1-6}$-alkyl; $—C_{1-6}$-cycloalkyl; -phenyl; $—C_{1-6}$-alkyl-phenyl; -heteroaryl selected from the group consisting of thienyl, furanyl and pyrrolyl; —C(=O)OH; $—C(=O)O—C_{1-6}$-alkyl; —CN; —OH; $—O—C_{1-6}$-alkyl, $—NH_2$, $—S—C_{1-6}$-alkyl, —F, —Cl, —Br, or —I;

R5, R6, R7 and R8 independently of one another mean, $—C_{1-6}$-alkyl, —CN, —OH, $—O—C_{1-6}$-alkyl, —F, —Cl, —Br, or —I; or R6 and R7 together with the carbon atoms to which they are attached form an unsubstituted phenyl ring;

wherein in each case the "$C_{1-6}$-alkyl" may be linear or branched, saturated or unsaturated, unsubstituted or monosubstituted with a substituent selected from —CN, —C(=O)OH, $—C(=O)O—C_{1-6}$-alkyl, —OH, $—O—C_{1-6}$-alkyl, $—NH_2$, $—NH—C_{1-6}$-alkyl, $—N(C_{1-6}$-alkyl) 2, $—N_3$, —F, —Cl, —Br, or —I;

wherein in each case the "$C_{1-6}$-cycloalkyl" may be linear or branched, saturated or unsaturated, unsubstituted or monosubstituted with a substituent selected from —CN, —C(=O)OH, $—C(=O)O—C_{1-6}$-alkyl, —OH, $—O—C_{1-6}$-alkyl, $—NH_2$, $—NH—C_{1-6}$-alkyl, $—N(C_{1-6}$-alkyl) 2, $—N_3$, —F, —Cl, —Br, or —I;

wherein in each case the "phenyl" may be unsubstituted, mono- or disubstituted with a substituent independently selected from —CN, —C(=O)OH, $—C(=O)O—C_{1-6}$-alkyl, —OH, $—O—C_{1-6}$-alkyl, $—NH_2$, $—NH—C_{1-6}$-alkyl, $—N(C_{1-6}$-alkyl) 2, $—N_3$, —F, —Cl, —Br, or —I;

wherein in each case the "heteroaryl" may be linear or branched, saturated or unsaturated, unsubstituted or monosubstituted with a substituent selected from —CN, —C(=O)OH, $—C(=O)O—C_{1-6}$-alkyl, —OH, $—O—C_{1-6}$-alkyl, $—NH_2$, $—NH—C_{1-6}$-alkyl, $—N(C_{1-6}$-alkyl) 2, $—N_3$, —F, —Cl, —Br, or —I; or a physiologically acceptable salt thereof.

2. The method according to claim 1, wherein

R1 and R2 together with the atoms to which they are attached form a cyclohexyl ring and mean-$CH_2CH_2CH_2CH_2$—;

R3 means —H, $—CH_3$, $—CH_2CH_2CH_3$, $—CH_2$-phenyl, $—CH_2$-p-chlorophenyl or $—CH_2—CN$;

R4 means-$CH_3$ or $—CH_2$-phenyl or

R5, R6, R7 and R8 independently of one another mean-$CH_3$, —OH, $—OCH_3$, —F, —Cl, —Br or —CN.

3. The method according to claim 1, wherein the MrgX2 antagonist is administered orally.

4. The method according to claim 1, wherein the MrgX2 antagonist is administered once daily, twice daily or thrice daily.

5. The method according to claim 2, wherein

R5 means $—CH_3$; or

R6 means $—CH_3$, —OH, $—OCH_3$, —F, —Cl, —Br or —CN;

R7 means $—CH_3$, —F, —Cl, —Br, —CN, $—OCH_3$ or —OH; or

R6 and R7 together with the carbon atoms to which they are attached form an unsubstituted phenyl ring.

6. The method according to claim 1, wherein the disease or disorder that is associated to the MrgX2 receptor is selected from the groups consisting of:

pain, anxiety, stress and stress-associated syndromes, depression, epilepsy, senile dementia, general cognitive dysfunctions, learning and memory disorders, withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence muscle-related disorders, convulsions, neurotransmitter and neurodegenerative diseases, withdrawal symptoms asthma, skin inflammation, dry skin, atopic eczema, psoriasis, urticaria, scabies, non-allergic hypersensitivity reactions, fibrosis, itch, or any combination thereof.

7. The method according to claim 6, wherein the pain consists of acute, nociceptive, neuropathic and/or chronic pain, inflammatory pain and/or itch.

* * * * *